(12) United States Patent
Foucher et al.

(10) Patent No.: US 10,939,684 B2
(45) Date of Patent: Mar. 9, 2021

(54) PREPARATION OF SULFONAMIDE-CONTAINING ANTIMICROBIALS AND SUBSTRATE TREATING COMPOSITIONS OF SULFONAMIDE-CONTAINING ANTIMICROBIALS

(71) Applicant: NANO SAFE COATINGS INCORPORATED, Jupiter, FL (US)

(72) Inventors: Daniel Foucher, Toronto (CA); Gideon Wolfaardt, Mississauga (CA); Alexander Gabriel Caschera, Amaranth (CA); Aman Ullah Khan, Toronto (CA); Kamlesh Mistry, Etobicoke (CA); Evan Lindsay Gilmore Ronan, Toronto (CA); Lukasz Porosa, Scarborough (CA)

(73) Assignee: NANO SAFE COATINGS INCORPORATED, Jupiter, FL (US)

( * ) Notice: Subject to any disclaimer, the term of this patent is extended or adjusted under 35 U.S.C. 154(b) by 204 days.

(21) Appl. No.: 15/755,231

(22) PCT Filed: Aug. 26, 2016

(86) PCT No.: PCT/CA2016/051014
§ 371 (c)(1),
(2) Date: Feb. 26, 2018

(87) PCT Pub. No.: WO2017/031599
PCT Pub. Date: Mar. 2, 2017

(65) Prior Publication Data
US 2018/0343870 A1 Dec. 6, 2018

Related U.S. Application Data

(60) Provisional application No. 62/210,593, filed on Aug. 27, 2015.

(51) Int. Cl.
*A01N 41/06* (2006.01)
*A01N 57/22* (2006.01)
(Continued)

(52) U.S. Cl.
CPC ............. *A01N 57/22* (2013.01); *A01N 41/06* (2013.01); *A01N 55/00* (2013.01); *B05D 3/065* (2013.01);
(Continued)

(58) Field of Classification Search
CPC ............................. C07C 307/06; C07F 7/1804
See application file for complete search history.

(56) References Cited

U.S. PATENT DOCUMENTS 2,774,786 A   12/1956 Erickson
3,697,402 A   10/1972 Kehr et al.
(Continued)

FOREIGN PATENT DOCUMENTS

NL           79189        4/1952
WO   WO 2010/096444 A2   8/2010
(Continued)

OTHER PUBLICATIONS

Porosa et al. Synthesis structures and properties of self-assembling quaternary ammonium dansyl fluorescent tags fro porous and non-porous surfaces. Journal of Materials Chemistry B. 2014. 1509-1520 (Year: 2014).*
(Continued)

*Primary Examiner* — Cachet I Proctor
(74) *Attorney, Agent, or Firm* — Eric L. Lane; Green Patent Law

(57) ABSTRACT

A quaternary ammonium sulfonamide compound of formula (I): wherein R=(II), $C_1$-$C_3$ linear or branched alkyl, $R_1$ and $R_2$ are the same or different and selected from $C_1$ to $C_{18}$
(Continued)

A = Polystyrene, B = Polyethylene, C = Polyvinyl Chloride (PVC), D = Polyether ether ketone (PEEK)

linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl groups of R may be substituted or unsubstituted, X=halogen, and Y=(III) wherein $R_6$, $R_7$, $R_8$, $R_9$ and $R_{10}$ are the same or different and selected from $C_1$ to $C_6$ linear or branched alkyl and the benzophenone is selected from the group consisting of substituted benzophenone and unsubstituted benzophenone, process for preparing the compound and antimicrobial surface coating compositions of the compound.

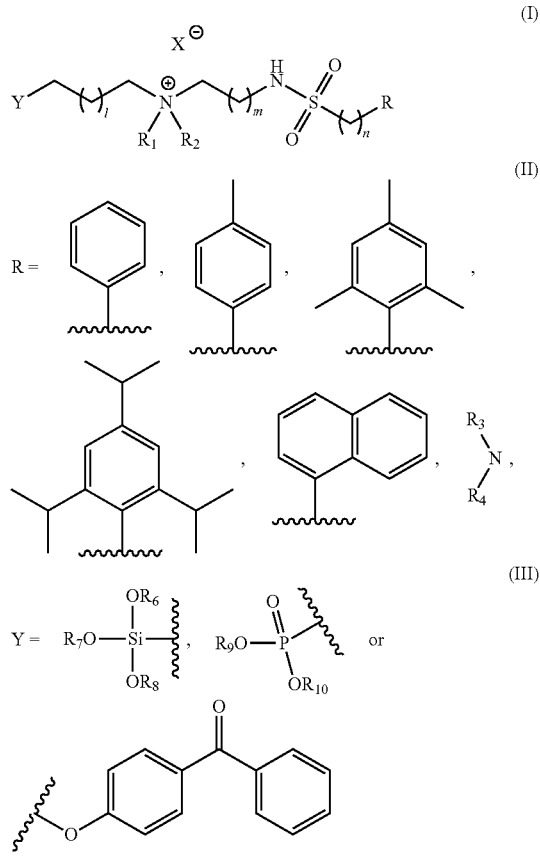

31 Claims, 5 Drawing Sheets

(51) Int. Cl.
| | |
|---|---|
| *C07C 307/06* | (2006.01) |
| *C07C 311/05* | (2006.01) |
| *C07C 311/18* | (2006.01) |
| *C07F 9/40* | (2006.01) |
| *A01N 55/00* | (2006.01) |
| *C07F 7/18* | (2006.01) |
| *B05D 3/06* | (2006.01) |

(52) U.S. Cl.
CPC .......... *C07C 307/06* (2013.01); *C07C 311/05* (2013.01); *C07C 311/18* (2013.01); *C07F 7/1804* (2013.01); *C07F 9/4006* (2013.01); *C07C 2602/42* (2017.05)

(56) References Cited

U.S. PATENT DOCUMENTS

| | | | |
|---|---|---|---|
| 4,948,819 | A | 8/1990 | Green et al. |
| 5,104,649 | A * | 4/1992 | Jansson .................. A01N 25/10 |
| | | | 424/78.31 |
| 5,714,360 | A | 2/1998 | Swan et al. |
| 2006/0147413 | A1 | 7/2006 | Alferiev et al. |
| 2007/0231291 | A1 | 10/2007 | Huang et al. |
| 2007/0287750 | A1 | 12/2007 | Burns et al. |
| 2013/0255061 | A1 | 10/2013 | Burkholz et al. |
| 2015/0175812 | A1 | 6/2015 | Ali et al. |
| 2015/0299475 | A1 * | 10/2015 | Porosa ...................... C09D 7/63 |
| | | | 427/553 |
| 2015/0322097 | A1 * | 11/2015 | Ferritto ................. C07F 7/1876 |
| | | | 536/56 |

FOREIGN PATENT DOCUMENTS

| | | |
|---|---|---|
| WO | WO 2011/139817 A2 | 11/2011 |
| WO | WO 2013/019918 A2 | 2/2013 |
| WO | WO 2014/089680 A1 | 6/2014 |
| WO | WO 2014/127451 A1 | 8/2014 |

OTHER PUBLICATIONS

Porosa et al., Synthesis, structures and properties of self-assembling quaternary ammonium dansyl fluorescent tags . . . , J. Mat. Chem., 1509-1520, 2014.
International Search Report dated Nov. 30, 2016 in related International Application No. PCT/CA2016/051014.
Germanaud et al., Syntheses de phosphobetaines amphiphiles neutres a distances intercharge variable, Bulletin de la Societe Chimique de France, 1988, 4, 699-704.
Nilsson et al., Variability in biofilm production by Listeria monocytogenes correlated to strain origin an growth conditions, Int'l J. Food Microbiology 150, 14-24 (2011).
Yang et al., Efficacy of Santizing Agents against Listeria monocytogenes Biofilms on High-Density Polyethylene Cutting Board Surfaces, J. Food Protection vol. 72, No. 5 (2009).
Feliciano et al, Efficacies of Sodium Hypochlorite and Quaternary Ammonium Santizers for Reduction of Norovirus . . . PLOS One vol. 7 Issue 12 (2012).
Tiller et al., Designing surfaces that kill bacteria on contact, Proc. National Academy of Sciences, 2001, 98, 5981.
Dhende et al. One-Step Photochemical Syntheses of Permanent, Nonleaching Ultrathin Antimicrobial Coatings for Textiles and Plastics, Appl Material Interfaces, 2011, 3, 2830.
Yagci et al., Self-stratifying antimicrobial polyurethane coatings, Prgress in Organic Coatings 72 (2011) 305-314.
Lawrence et al., The Antibacterial Actions of Quaternary Ammonium Sulfonamides, J. American Pharmaceutical Assocation, 1948, 37, 424-428.
Song et al. New synthetic aliphatic sulfonamido-quaternary ammonium salts as anticancer chemotherapeutic agents, European J. Medicinal Chem, 2013, 69.

* cited by examiner

A = Polystyrene, B = Polyethylene, C = Polyvinyl Chloride (PVC), D = Polyether ether ketone (PEEK)

PREPARATION OF SULFONAMIDE-CONTAINING ANTIMICROBIALS AND SUBSTRATE TREATING COMPOSITIONS OF SULFONAMIDE-CONTAINING ANTIMICROBIALS

FIELD OF THE DISCLOSURE

This disclosure relates to dual-action antimicrobial compounds and compositions for treating substrates, preferably surfaces, to reduce, preferably inhibit microbe growth and biofouling on treated substrates.

BACKGROUND

One of the main challenges faced by the medical industry is infection control and reducing the spread of microorganisms such as fungi, bacteria and viruses. Several microorganisms have the ability to attach to surfaces, for example porous surfaces and to proliferate forming colonies called biofilms. The use of antibiotics to treat infectious diseases caused by biofilms has become one of the biggest milestones in the history of medicine. However, after widespread use of these antibiotics, and other chemicals used for the purpose of disinfection, several strains of microorganisms (e.g. bacteria), have developed resistance to them. For the growing number of microorganisms with clinical importance (one example is pathogens), there is either no effective therapy or only one or two antibiotics that are hard to administer, expensive and/or have increasingly toxic side effects. Furthermore, when growing on surfaces as biofilms, microorganisms are generally more persistent, and it is now acknowledged that the majority of infections involve biofilms. Biofilms also pose a notable threat of contamination in food processing facilities and spoilage of other products susceptible to microbial attack.

Bacterial infections in hospital environments are spread by two different ways: external contamination or in vivo contamination from implants. Patients can develop external infections through contact with surfaces such as door handles, pens, telephones, health care workers uniforms ("HCWU"), stethoscopes, or sterile packaging that have been colonized by microorganisms. Hospital-acquired infections ("HAI") from contact with pathogenic microorganisms affect approximately 2 million people and result in more than 100,000 deaths in the U.S.A. each year. Such infections require 10-20 days of additional patient hospitalization, costing the already strained U.S. health-care systems approximately $25,000-30,000 per infection totaling billions of dollars per year.

The second route for bacteria to infect patients is through hospital invasive support equipment such as intravascular lines and implanted medical devices such as artificial prosthetics, cardiovascular implants and urinary catheters. Implant associated infections ("IAI") occur in more than one million patients and cost an estimated $3 billion in the U.S. per year. For example, approximately 10-50% of patients with implanted catheters run the risk of developing urinary tract infections ("UTI") resulting in additional healthcare costs. The rise in the frequency and severity of HAI's and IAI's can be attributed to decreased antibiotic efficacy against drug-resistant strains of pathogens found in surface biofilms.

Biofilm formation involves three phases beginning with the initial reversible adhesion of bacteria on a surface through polysaccharides and adhesion proteins on the bacterial membrane (phase I). Under appropriate conditions, bacteria subsequently firmly attach to a surface (phase II), followed by the secretion of a protective polymeric matrix (biofilm, phase III) in which the bacteria typically show a marked increase in resistance to antibiotics, compared to none-adherent bacteria. As a result, once the infection occurs, it becomes difficult to treat. Thus, strategies that prevent bacterial contamination or destroy adsorbed microorganisms that lead to biofilm formation are actively sought.

One approach in preventing biofilm formation, and thus the potential to cause spoilage or infection is the use of antimicrobial coatings on surfaces that are not susceptible to the development of resistance by the target microorganisms. These coatings have bacteriostatic (inhibiting) or bactericidal (killing) properties and thus afford a preventative strategy compared to disinfection, which is reactive, often after some damage or infection has occurred. In contrast to conventional antibiotics, bacteria do not readily develop resistance to antimicrobial coatings that inhibit microorganisms in a mechanical, as opposed to a chemical fashion. This important distinction, and the related alarming rate at which the number of effective antibiotics decline, is a primary reason for the rapidly growing interest in these antimicrobial coatings in recent years.

Quaternary ammonium compounds ("QACs") have gained recognition as surfactants with antimicrobial activity. QAC's consist of an irreversibly positively charged quaternary nitrogen atom where often at least one substituent is a long aliphatic chain. The synthesis of these compounds involves the quaternization of a tertiary amine following the Menshutkin reaction (i.e. a reaction of a tertiary amine with an alkyl halide).

Without being bound by any particular theory, the mode of action of QAC's in killing bacteria is multi-stepped. First, the QAC is adsorbed into the bacterial cell wall. Second, the long hydrophobic alkyl chain of the QAC interacts with the phospholipid bilayer making up the bacteria cell membrane and alters its fluidity and structure which adds stress to the cell wall. Finally, this added stress on the cell wall upsets the bilayer, expelling cytoplasmic material and ultimately caused cell death.

Polymeric antimicrobial coatings have the advantage of being chemically stable, non-toxic and non-volatile making them more efficient, selective and environmentally safe compared to traditional antimicrobial coatings which depend on leaching of the chemical from the substrate. It has become common practice over the past 35 years to incorporate antimicrobial coatings in thermoplastic polymer solutions. Furthermore, solvents commonly used to incorporate the antimicrobials in the thermoplastic polymers include tetrahydrofuran ("THF") and dimethyl formamide ("DMF"). These solvents have the ability of attacking polymeric surfaces including those of polyurethane, polyisoprene, butyl rubber, polycarbonate, etc. This often distorts the surface, altering the integrity of the material at the surface, which in turn may ultimately enhance attachment by microbial cells resistant to the antimicrobial ingredient, and other microbes later when the concentration of the antimicrobial ingredient drops below the threshold required for inhibition. Also, once the prior art coatings are applied to the surfaces, drying times on the order of almost 24 hours are required to completely evaporate the solvent from the surface.

Development of antimicrobial coatings is limited by the availability of suitable antimicrobials that may be incorporated into thermoplastic polymers. Silver is one common agent used both in elemental and salt form. However, the technology to incorporate silver into polymeric materials is tedious, expensive and not environmentally friendly. Moreover, the performance of silver is weak taking up to eight hours to reach efficacious levels against microbes and discolouration is common in silver treated materials. Thus there exists a long-felt need for a composition to eradicate microbes and prevent biofilm formation that is low-cost, durable and efficacious without these deleterious side effects. In an effort to increase the stability of antimicrobial films on polymer surfaces, irreversible covalent attachment of the antimicrobial to the surface desirable. Methods for grafting antimicrobials to polymer surfaces have been developed usually using functionalized surfaces and/or antimicrobial molecules. However, some of these functionalizing techniques are expensive and require extensive synthetic methodologies. Recently, light-activated systems involving photoreactive groups have been reported. Benzophenone is a popular photoreactive group and is commonly used in fragrances and cosmetics.

The first quaternary ammonium phosphonate compounds (phosphonate quats) were disclosed in the early 1950's in U.S. Pat. No. 2,774,786 and Dutch patent NL 79189 for use as synthetic detergents. In the patents syntheses, the final product could only be isolated as a sodium salt of the phosphobetaine after hydrolysis of the phosphonate ester with HCl followed by treatment with $NaHCO_3$. In a similar synthesis Germanaud et al., (*Bulletin de la Societe Chimique de France*, 1988, 4, 699-704) published the isolation of the phosphonate quats as betaines by purification on an anion exchange resin. The products disclosed in the patents were not spectrally characterized and were used as is, while Germanaud's purification was costly and the product wasn't isolated as a phosphonic acid.

Phosphonate monolayers for the antimicrobial treatment of surfaces have been shown to be advantageous over self-assembled monolayers (SAMs) of thiols in terms of durability, long-term stability and surface coverage, especially on titanium and stainless steel. Thiol-based SAM's lack substrate specificity (mainly reserved for gold surfaces) and long-term stability needed for biomedical applications, (i.e. implants). Over time, the thiol-based SAM's become oxidized to sulfonates, which lack affinity for gold and become displaced from the surface.

*Listeria* has been observed to increase biofilm production when conditions become more unstable or non-ideal for active growth (Nilsson, R., Ross, T. and Bowman, J. (2011) Variability in biofilm production by *Listeria monocytogenes* correlated to strain origin and growth conditions. *International Journal of Food Microbiology* 150. Pages 14-24). It appears that *Listeria* use biofilm production as a form of defense, and the strength of their survival seems linked to the maturity of the biofilm as does their resistance to antimicrobials.

Biofilms allows for essential cell to cell interactions as well as providing protection to harmful conditions. *Listeria* biofilms are structurally simple and a mature community can be formed after 24 hours, which is the incubation period of the large droplet tests.

In general, actively growing *Listeria* cells are susceptible to quaternary ammonium compounds (QACs), even at relative short exposure times over broad temperature and pH ranges. In contrast, it appears that mature biofilms are more resistant against QACs, which suggests that a component of the mature biofilm, potentially an extra-cellular polymeric substance (EPS), could provide protection against QACs. This behavior could be unique to *Listeria* strains, but there are likely other microorganisms that that possess similar mechanisms for surviving exposure to antimicrobials.

In addition to biofilm maturity, it appears that other factors such as high pH and smooth attachment surfaces may impact on antimicrobial efficacy of QACs against *Listeria* (Yang, H., Kendall, P., Medeiros and L, Sofos, J. (2009) Efficacy of sanitizing agents against *Listeria monocytogenes* biofilms on high-density polyethylene cutting board surfaces. Journal of Food Protection, Vol. 72, No. 5, Pages 990-998). Lastly the possibility of non-lethal doses of disinfectants being exposed to the community over time results in resistance by the microbial community (Feliciano, L, Li, J., Lee, J., Pascall, M. (2012) Efficacies of sodium hypochlorite and quaternary ammonium sanitizers for reduction of norovirus and selected bacteria during ware-washing operations. PLOS ONE, Vol 7, Issue 12. E50273). The *Listeria* strains isolated could be of a stock that has built up these resistances.

In order to prevent the formation of biofilm, strategies have been employed in the past to make surfaces inhospitable to bacteria. For example, small molecule monolayers or polymer thin films either "grafted to" or "grown from" a surface have been widely used to prepare antimicrobial surfaces and clothing. These prior art monolayers or polymer coatings include, for example, non-biofouling coatings which are passive strategies that rely on preventing bacterial adhesion with hydrophobic or zwitterionic thin films, but do not kill the approaching bacteria. A second class of antibacterial thin films kills microbes on contact either by releasing a biocidal agent or immobilizing a biocidal agent. A third class of antibacterial thin films utilize a combination strategy of including a non-biofouling and biocidal component into the coating. Currently, there are no known environmentally-safe sulfonamide quaternary ammonium coatings used to protect surfaces from bio-fouling.

U.S. Pat. No. 3,697,402 teaches photocurable thiol-capped polyalkene polymers which when applied to a surface and exposed to ultra-violet ("UV") light forms a solid product for use, among other things, as a sealant, coating, and adhesive.

U.S. Pat. No. 4,948,819 teaches water-soluble, quaternary ammonium methacrylate coatings having a photo-active linking molecule, with uses as an UV-cured lacquer coating. U.S. Pat. No. 5,714,360 teaches a chemical cross-linking agent X—Y—X where X is a photoreactive radical and Y is a nitrogen containing group used to attach chemical compounds to other compounds or to substrates.

J. C. Tiller et al., (Proceedings of the National Academy of Sciences, 2001, 98, 5981) teaches a surface coating composition of polyvinylpyrrolidone ("PVP")-QAC in which the surface is a pre-functionalized glass surface and PVP-QAC is bonded to the functional groups. The surface needs to be pre-functionalized with an acyl-chloride compound in order for the coating to bond to the glass surface.

U.S. Patent Application Publication No. 2006/0147413 teaches a water-soluble, photo-activatable polymer bonded through a reactive group biomaterial used to deploy molecular therapeutics such as proteins, genes, vectors and cells.

U.S. Patent Application Publication No. 2007/0231291 teaches a polymeric QAC-polyethyleneimine used to protect surfaces against bacteria and fungi attack. International Patent Application Publication WO2010/065421 teaches UV-curable coatings containing rheology modifiers or antimicrobial agents wherein the antimicrobial agents are not covalently linked to the coating polymer.

International Patent Application Publication WO2010/096444 teaches a UV-curable polyethyleneimine polymer that can be attached to pre-functionalized surfaces giving the surface antimicrobial activity. The surfaces are functionalized by reacting the surfaces with 7-octenyl trichlorosilane.

V. P. Dhende et al (Application of Material Interfaces, 2001, 3, 2830) teaches a UV-curable polyethyleneimine co-polymer that can be attached to pre-functionalized surfaces giving the surface antimicrobial activity. The surfaces are functionalized by reacting the surfaces with octyltrichlorosilane.

International Patent Application Publication WO2011/139817 teaches a UV-curable vinyl-substituted polyethyleneimine that can be attached to pre-functionalized surfaces and imparting antimicrobial activity to the surfaces. The surfaces are functionalized by reacting the surface with 7-octenyl trichlorosilane.

Mustafa Baris Yagci ("Self-Stratifying Antimicrobial Coatings", Ph.D. dissertation, Jan. 16, 2012) teaches inter alia a QAC-bonded polyurethane surface coating.

Lawrence C. A. et al., Journal of the American Pharmaceutical Association, 1948, 37, 424-428 teaches quaternary ammonium compounds modified with sulfonamide functionalities and their antibacterial activity. Specifically, the compounds comprise a para-substituted benzene ring wherein one end contains the sulfonamide functionality and the other constitutes the quaternary ammonium site. The absence of a linker group in the compounds precludes covalent attachment of the compounds to substrates.

Song D. et al., European Journal of Medicinal Chemistry, 2013, 69, 670-677 teaches quaternary ammonium sulfonamides and their use as anti-cancer agents.

International Patent Application Publication WO2014/089680 teaches UV cured, benzophenone-capped quaternary ammonium compounds and their use as antimicrobial surface treatments.

International Patent Application Publication WO2014/127451 teaches quaternary ammonium multi-dentate phosphonate compounds and their use as durable, antimicrobial surface treatments.

U.S. Pat. No. 5,104,649 teaches biocide-treated polymers and surfaces in which the biocide is linked to the surface through a multi-step process.

U.S. Patent Application Publication No. 2007/0287750 teaches polycationic sulfonamide compounds used for treating diseases.

U.S. Patent Application Publication No. 2013/0255061 teaches systems and methods for coating a polymeric surface, specifically medical devices, with a biocide compound.

U.S. Patent Application Publication No. 2015/0175812 teaches an antimicrobial polymer used for touch sensitive surfaces in which the polymer contains pendant antimicrobial groups.

International Patent Application Publication WO2013/019918 teaches covalent attachment of sulfonyl-quaternary ammonium compounds to fabric surfaces having OH groups via a sulfur-oxygen linkage.

Thus, there has been a long-felt need for a durable and environmentally safe antimicrobial quaternary ammonium sulfonamide for use in surface treatment and a process to manufacture the same.

SUMMARY

In one aspect of the present disclosure there is provided a quaternary ammonium sulfonamide compound of formula (I):

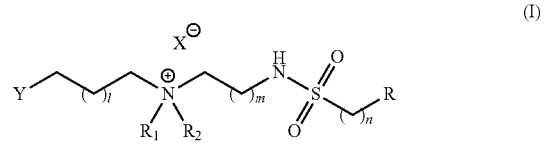

wherein

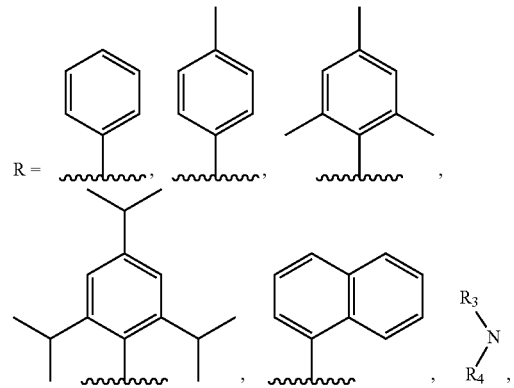

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl rings of R may be substituted or unsubstituted, X=halogen, and

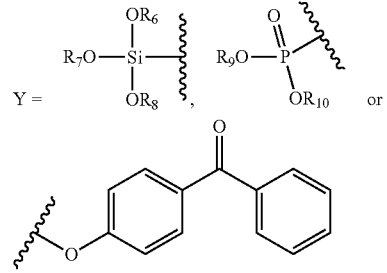

wherein $R_6$, $R_7$, $R_8$, $R_9$ and $R_{10}$ are the same or different and selected from $C_1$ to $C_6$ linear or branched alkyl, and the phenyl rings of the benzophenone may be substituted or unsubstituted.

In a preferred embodiment, the halogen is selected from the group consisting of Cl, Br and I. In a preferred embodiment, $R_1$ and $R_2$ are the same and selected from methyl, ethyl, n-propyl or isopropyl groups, more preferably methyl groups. In a preferred embodiment, $R_3$ and $R_4$ are the same and selected from methyl, ethyl, n-propyl or isopropyl groups, more preferably methyl groups. In a preferred embodiment, l is selected from 1, 2 or 3, more preferably 1.

In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, $R_6$, $R_7$ and $R_8$ are the same and selected from methyl, ethyl, n-propyl or isopropyl groups, more preferably methyl groups. In a preferred embodiment, $R_9$ and $R_{10}$ are the same and selected from methyl, ethyl, n-propyl or isopropyl groups, more preferably isopropyl groups.

In another aspect of the present disclosure there is provided a process for preparing a quaternary ammonium sulfonamide of formula (I):

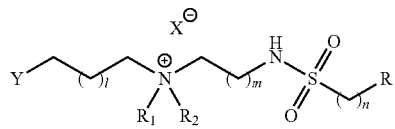

(I)

comprising reacting a compound of formula (II)

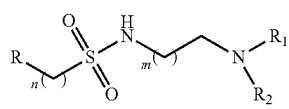

(II)

with an alkyl halide of formula (III)

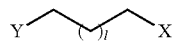

(III)

wherein

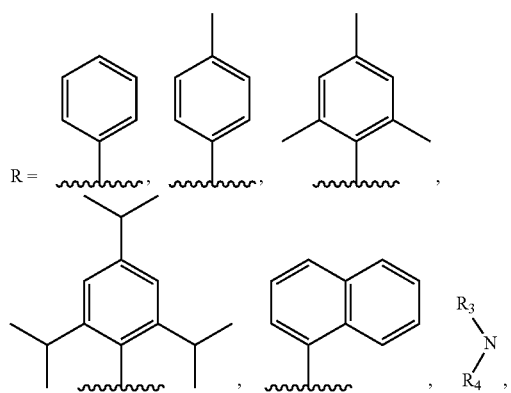

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl rings of R may be substituted or unsubstituted, X=halogen, and

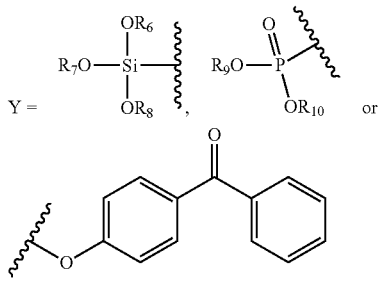

wherein $R_6$, $R_7$, $R_8$, $R_9$ and $R_{10}$ are the same or different and selected from $C_1$ to $C_6$ linear or branched alkyl, and wherein the phenyl rings of the benzophenone may be substituted or unsubstituted.

In a preferred embodiment, halogen is selected from the group consisting of Cl, Br and I. In a preferred embodiment, $R_1$ and $R_2$ are the same and selected from methyl, ethyl, n-propyl or isopropyl groups, more preferably methyl groups. In a preferred embodiment, $R_3$ and $R_4$ are the same and selected from methyl, ethyl, n-propyl or isopropyl groups, more preferably methyl groups. In a preferred embodiment, l is selected from 1, 2 or 3, more preferably 1. In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, $R_6$, $R_7$ and $R_8$ are the same and selected from methyl, ethyl, n-propyl or isopropyl groups, more preferably methyl groups. In a preferred embodiment, $R_9$ and $R_{10}$ are the same and selected from methyl, ethyl, n-propyl or isopropyl groups, more preferably isopropyl groups.

In a preferred embodiment the process may take place in at least one polar, aprotic solvent, preferably selected from the group consisting of dichloromethane (DCM), dimethylformamide (DMF), tetrahydrofuran (THF), acetonitrile (ACN) and combinations thereof, more preferably ACN. The process may be carried out at an elevated temperature up to proximate the refluxing temperature of the at least one polar, aprotic solvent. The reaction duration may be from formation of some product to complete reaction, preferably about 2 hours to about 48 hours, more preferably from about 3 hours to about 12 hours. The final product may be purified, preferably by washing, more preferably by washing with a dialkyl ether, preferably diethyl ether. The final product may be dried, preferably under vacuum of about $10^{-3}$ mmHg and preferably at room temperature. In a preferred embodiment, where Y is selected from benzophenone the drying step is preferably carried out in the absence of light. In a preferred embodiment, where Y is selected from a silane the drying step is preferably carried out in the absence of moisture.

In another aspect of the present disclosure there is provided a process for preparing a compound of formula (II)

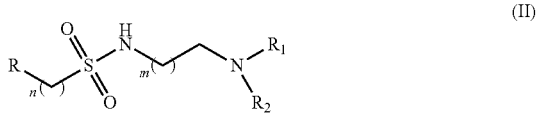

(II)

comprising reacting a compound of formula (IV)

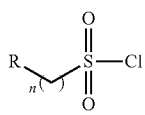

(IV)

with a compound of formula (V)

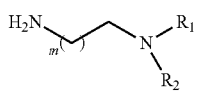

(V)

optionally in the presence of a base, wherein

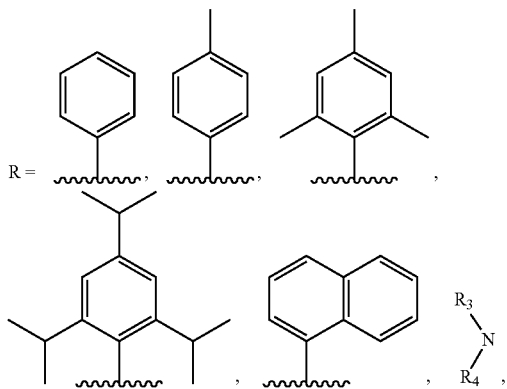

$C_1$-$C_3$ linear or branched alkyl,
$R_1$ and $R_2$ are the same or different and selected from $C_1$ to $C_{18}$ linear or branched alkyl,
$R_3$ and $R_4$ are the same or different and selected from $C_1$ to $C_4$ linear or branched alkyl, $CF_3$, $OR_5$
where $R_5$ is $C_1$ to $C_8$ linear or branched alkyl or polyethylene oxide,
m is 2, 3, 4, 5, 6, 7, 8, 9, 10, 11, 12, 13, 14, 15, 16 or 17, and
n is 0, 1, 2, 3, 4, 5, 6, 7, 8, 9, 10, 11, 12, 13, 14, 15, 16, 17 or 18, wherein the aryl rings of R may be substituted or unsubstituted.

Preferably the optional base is selected from an amine, preferably an alkylamine or pyridine, more preferably a trialkylamine, most preferably triethylamine. In a preferred embodiment, $R_1$ and $R_2$ are the same and selected from methyl, ethyl, n-propyl or isopropyl groups, more preferably methyl groups. In a preferred embodiment, $R_3$ and $R_4$ are the same and selected from methyl, ethyl, n-propyl or isopropyl groups, more preferably methyl groups. In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0.

In a preferred embodiment the process may take place in a polar, aprotic solvent, preferably selected from the group consisting of ACN, DMF, THF, DCM, and combinations thereof, preferably DCM. The addition of reactants may be carried out at the a temperature from about −20° C. to about 10° C., more preferably from about −10° C. to about 5° C. and most preferably at about 0° C. The reaction may proceed from about 0° C. to about room temperature and from formation of some product to complete reaction, preferably from about 2 hours to about 8 hours, more preferably from about 3 hours to about 6 hours.

In another aspect of the present disclosure there is provided an antimicrobial substrate treating, preferably substrate coating, more preferably surface coating composition comprising at least one compound of formula (I)

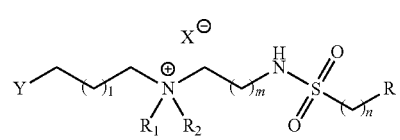

(I)

wherein

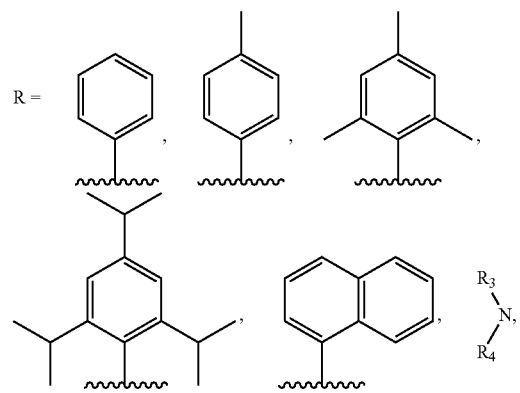

$C_1$-$C_3$ linear or branched alkyl,
$R_1$ and $R_2$ are the same or different and selected from $C_1$ to $C_{18}$ linear or branched alkyl,
$R_3$ and $R_4$ are the same or different and selected from $C_1$ to $C_4$ linear or branched alkyl, $CF_3$, $OR_5$
where $R_5$ is $C_1$ to $C_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18, wherein the aryl rings of R may be substituted or unsubstituted,
X=halogen, and

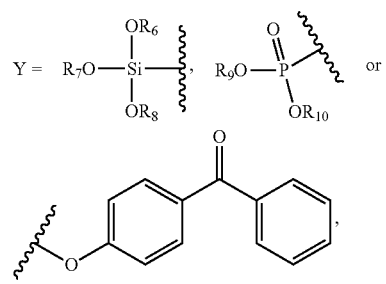

wherein $R_6$, $R_7$, $R_8$, $R_9$ and $R_{10}$ are the same or different and selected from $C_1$ to $C_6$ linear or branched alkyl, wherein the phenyl rings of the benzophenone may be substituted or unsubstituted, and an environmentally friendly carrier. In a preferred embodiment halogen is selected from the group consisting of Cl, Br and I. In a preferred embodiment, $R_1$ and $R_2$ are the same and selected from methyl, ethyl, n-propyl or isopropyl groups, more preferably methyl groups. In a preferred embodiment, $R_3$ and $R_4$ are the same and selected from methyl, ethyl, n-propyl or isopropyl groups, more preferably methyl groups. In a preferred embodiment, l is selected from 1, 2 or 3, more preferably 1. In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, $R_6$, $R_7$ and $R_8$ are the same and selected from methyl, ethyl, n-propyl or isopropyl groups, more preferably methyl groups. In a preferred embodiment, $R_9$ and $R_{10}$ are the same and selected from methyl, ethyl, n-propyl or isopropyl groups, more preferably isopropyl groups.

In a preferred embodiment, the environmentally friendly carrier is water, preferably a mixture of water, preferably distilled water, and at least one alkanol, preferably said alkanol is selected from the group consisting of methanol, ethanol, isopropanol and combinations thereof, wherein the alkanol is preferably methanol or ethanol and said water is preferably, distilled water. In a preferred embodiment the mixture of alkanol and water has a ratio of alkanol to water from about 5:95 to about 80:20, more preferably from about 10:90 to about 75:35 and most preferably from about 10:90 to about 70:30. In a preferred embodiment when the alkanol is methanol the ratio of alkanol to water is from about 30:70 to about 70:30. In a preferred embodiment when the alkanol is ethanol the ratio of alkanol to water is from about 10:90 and about 40:60. In a preferred embodiment the concentration of antimicrobial quaternary ammonium sulfonamide in the composition is from about at least 0.1%, preferably from about 0.5% to about 2%, more preferably from about 0.75% to about 1.5% and most preferably from about 0.75% to about 1.25%.

In another aspect of the present disclosure there is provided a process for treating, preferably coating, a substrate with an antimicrobial comprising the steps of (i) contacting the substrate with an antimicrobial composition comprising at least one compound of formula (I)

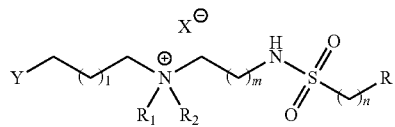
(I)

wherein

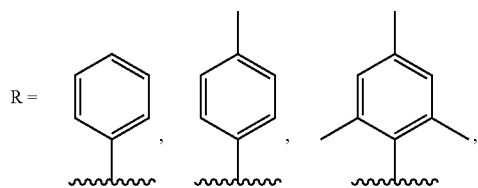

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl rings of R may be substituted or unsubstituted, X=halogen, and

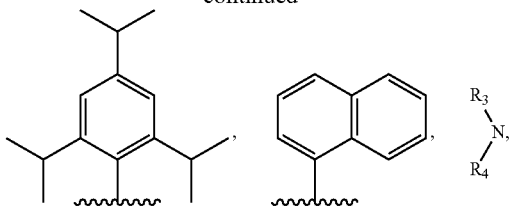

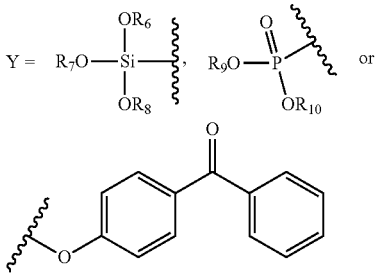

wherein $R_6$, $R_7$, $R_8$, $R_9$ and $R_{10}$ are the same or different and selected from $C_1$ to $C_6$ linear or branched alkyl, wherein the phenyl rings of the benzophenone may be substituted or unsubstituted, and an environmentally friendly carrier, (ii) drying the treated substrate, in one embodiment allowing for passively drying and in another embodiment actively drying, and (iii) optionally irradiating the treated substrate.

In a preferred embodiment, the halogen is selected from the group consisting of Cl, Br and I. In a preferred embodiment, $R_1$ and $R_2$ are the same and selected from methyl, ethyl, n-propyl or isopropyl groups, more preferably methyl groups. In a preferred embodiment, $R_3$ and $R_4$ are the same and selected from methyl, ethyl, n-propyl or isopropyl groups, more preferably methyl groups. In a preferred embodiment, l is selected from 1, 2 or 3, more preferably 1. In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, $R_6$, $R_7$ and $R_8$ are the same and selected from methyl, ethyl, n-propyl or isopropyl groups, more preferably methyl groups. In a preferred embodiment, $R_9$ and $R_{10}$ are the same and selected from methyl, ethyl, n-propyl or isopropyl groups, more preferably isopropyl groups.

In another preferred embodiment, the substrate may be a porous or a non-porous substrate, in yet another preferred embodiment, the substrate may be a surface. In a preferred embodiment, passively drying may include allowing the treated substrate, preferably coated substrate, more preferably coated surface to dry at room temperature. More preferably room temperature is from about 15° C. to about 30° C. and most preferably from about 20° C. to about 25° C. In a preferred embodiment, actively drying may include allowing the treated substrate, preferably coated substrate, more preferably coated surface to dry at a temperature above room temperature and at a pressure at or below room pressure. More preferably the temperature above room temperature is at least 40° C. More preferably the pressure at or below room pressure is from about $10^{-3}$ mm Hg to about 760 mm Hg.

In another aspect of the present disclosure there is provided a process for treating, preferably coating a substrate, preferably a surface, with an antimicrobial comprising the steps of (i) contacting the substrate, preferably the surface with an antimicrobial composition comprising a compound of formula (I)

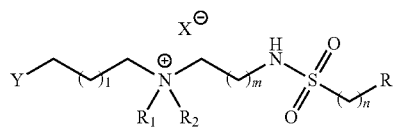

wherein

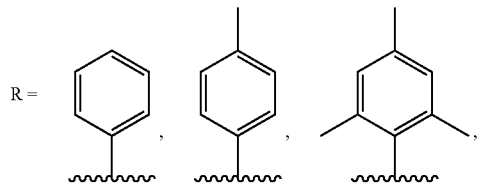

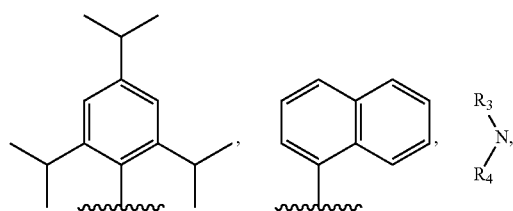

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl rings of R may be substituted or unsubstituted, X=halogen, and

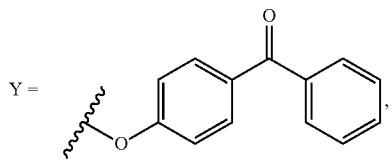

wherein the phenyl rings of the benzophenone may be substituted or unsubstituted, and an environmentally friendly carrier, (ii) drying the treated, preferably coated substrate, preferably coated surface, in one embodiment passively or in another embodiment actively, and (iii) irradiating the treated, preferably coated substrate, more preferably coated surface. In a preferred embodiment, halogen is selected from the group consisting of Cl, Br and I. In a preferred embodiment the substrate, preferably surface, may be a porous or non-porous substrate, preferably a porous or non-porous surface. Preferably the substrate, more preferably the surface, is a polymer or a non-cellulosic fibre. Preferably the substrate, more preferably the surface, may include, but not be limited to, polymers such as polyethylene, polypropylene, acrylonitrile-butadiene-styrene, polyurethane, polyvinyl chloride or nylon articles such as food trays, molded bedding parts, desk chairs and assorted furniture, disposable syringes, plastic handles for appliances, bathroom fixtures, window blinds and the like. Depending on the article or substrate, preferably surface to be treated, preferably coated, the skilled person would take the steps necessary to ensure the composition substantially treats, preferably coats the substrate, preferably the surface, preferably fully coats the substrate, more preferably fully coats the surface. For example, an article may only require one application of the composition, or the article may require multiple applications of the composition to ensure the article is substantially treated, preferably substantially coated. In a preferred embodiment the irradiating step comprises irradiating the treated, preferably coated substrate, more preferably coated surface, preferably with UV light.

In yet another aspect of the present disclosure there is provided a process for treating, preferably coating a substrate, preferably a surface, with an antimicrobial comprising the steps of (i) contacting the substrate, preferably a surface with, an antimicrobial composition comprising a compound of formula (I)

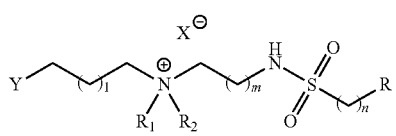

wherein

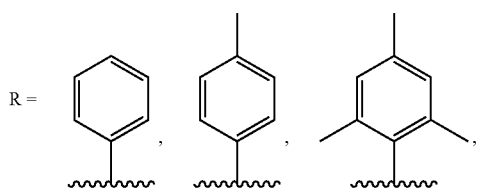

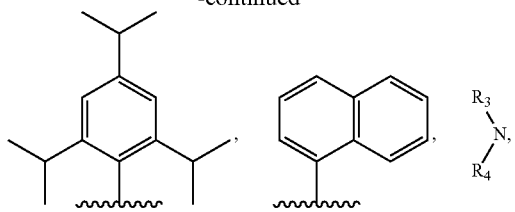

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl rings of R may be substituted or unsubstituted, X=halogen, and

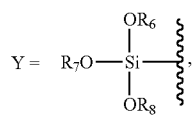

wherein $R_6$, $R_7$ and $R_8$ are the same or different and selected from $C_1$ to $C_6$ linear or branched alkyl, and an environmentally friendly carrier, preferably with stirring and heating, (ii) drying the treated substrate, preferably coated substrate, more preferably coated surface and washing the treated substrate, preferably coated substrate, more preferably coated surface. Preferably the washing step may be carried out using water. In a preferred embodiment, halogen is selected from the group consisting of Cl, Br and I. In a preferred embodiment, $R_1$ and $R_2$ are the same and selected from methyl, ethyl, n-propyl or isopropyl groups, more preferably methyl groups. In a preferred embodiment, $R_3$ and $R_4$ are the same and selected from methyl, ethyl, n-propyl or isopropyl groups, more preferably methyl groups. In a preferred embodiment, 1 is selected from 1, 2 or 3, more preferably 1. In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, $R_6$, $R_7$ and $R_8$ are the same and selected from methyl, ethyl, n-propyl or isopropyl groups, more preferably methyl groups. The substrate may be a porous or a non-porous substrate. Preferably the substrate, more preferably the surface, may include, but not be limited to, glass, cellulosic material, cotton and cotton-blended articles such as textiles, clothing, towels, bandages, outdoor fabrics and the like. In a preferred embodiment the heating is from a radiant heat source to produce a treating temperature from about 30° C. to about 80° C., more preferably from about 35° C. to about 75° C. and most preferably about 40° C. In a preferred embodiment the stirring occurs from about 3 minutes to about 5 minutes, most preferably about 4 minutes. Depending on the article or substrate to be treated, preferably coated, the skilled person would take steps necessary to ensure the composition substantially treats, preferably coats the substrate, preferably surface, and preferably fully coats the substrate, preferably the surface. For example, an article may only require one application of the composition, or the article may require multiple applications of the composition to ensure the article is substantially treated, preferably substantially coated.

In yet another aspect of the present disclosure there is provided a process for treating a substrate, preferably a surface, with an antimicrobial comprising the steps of (i) contacting the substrate, preferably a heated substrate, more preferably a heated surface, with an antimicrobial composition comprising a compound of formula (I)

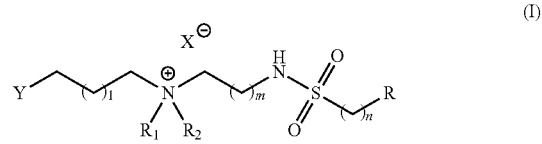

wherein

R =

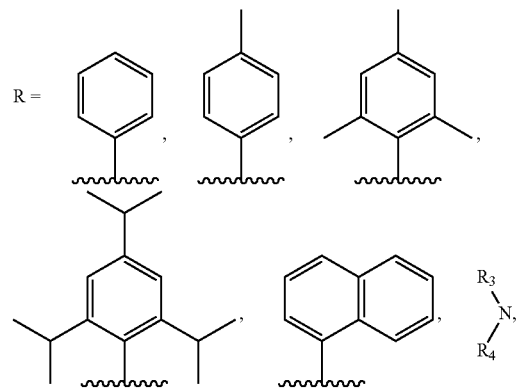

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl rings of R are substituted or unsubstituted, X=halogen, and

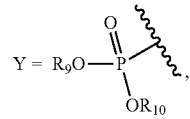

wherein $R_9$ and $R_{10}$ are the same or different and selected from $C_1$ to $C_6$ linear or branched alkyl, and an environmentally friendly carrier, (ii) optionally further heating the substrate thereafter and (iii) drying the substrate. Preferably the heating is radiative heating. In a preferred embodiment, the halogen is selected from the group consisting of Cl, Br and I. In a preferred embodiment, R$_1$ and R$_2$ are the same and selected from methyl, ethyl, n-propyl or isopropyl groups, more preferably methyl groups. In a preferred embodiment, R$_3$ and R$_4$ are the same and selected from methyl, ethyl, n-propyl or isopropyl groups, more preferably methyl groups. In a preferred embodiment, l is selected from 1, 2 or 3, more preferably 1. In a preferred embodiment, R$_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, R$_9$ and R$_{10}$ are the same and selected from methyl, ethyl, n-propyl or isopropyl groups, more preferably isopropyl groups. The substrate may be a porous or a non-porous substrate.

In a preferred embodiment, the antimicrobial coating composition may be applied onto a given substrate, preferably a surface, preferably by dip coating, painting or with aerosol spraying with an about 1 to an about 20 mM solution of the phosphonate compound for a length of time so as to coat, preferably substantially coat, more preferably completely coat the substrate, preferably the surface. In one embodiment, the coating process may be repeated to apply additional layers of the phosphonate antimicrobial. Preferably the antimicrobial coating composition may be coated onto various substrates such as, but not limited to, minerals, metals, metal oxides or metal alloys of aluminum, copper, iron, steel, titanium, zirconium and silicon (silica) and the like. More preferably the substrate is selected from a metal or a metal oxide. Most preferably the substrate is a metal.

In a preferred embodiment, the environmentally friendly carrier is water, preferably a mixture of water and at least one alkanol, said alkanol is selected from the group consisting of methanol, ethanol, isopropanol and mixtures thereof, wherein the alkanol is preferably selected from methanol and ethanol and said water is distilled water. In a preferred embodiment the mixture of at least one alkanol and water has a ratio of alkanol to water from about 5:95 to about 80:20, more preferably from about 10:90 to about 75:35 and most preferably from about 10:90 to about 70:30. In a preferred embodiment when the alkanol is methanol the ratio of alkanol to water is from about 30:70 to about 70:30. In a preferred embodiment when the alkanol is ethanol the ratio of alkanol to water is from about 10:90 and about 40:60.

In yet another aspect of the present disclosure there is provided a test flow device, preferably made from a plastic, for evaluating antimicrobial quaternary ammonium sulfonamide coated substrates at solid/liquid interfaces. In a preferred embodiment the plastic may be exposed to single or multiple strains of bacteria typically capable of forming biofilms under controlled conditions and evaluated for growth or death of colony forming units.

In yet another aspect there is provided an antimicrobial quaternary ammonium sulfonamide for reducing microbial growth at solid/air interfaces. In a preferred embodiment microbial growth may be attributed to a group of microbes consisting of bacterial, fungal and viral.

According to yet another aspect of the present disclosure, there is provided a substrate, preferably a surface, treated, preferably coated, with an antimicrobial as defined herein. In a preferred embodiment the substrate, preferably surface, may be porous or non-porous.

According to yet another aspect of the present disclosure, there is provided a method of reducing growth of at least one microbe on a substrate treated with an antimicrobial composition comprising at least one compound of formula (I)

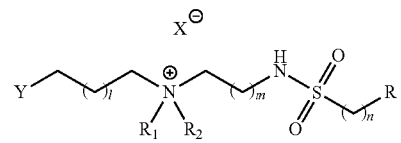

wherein

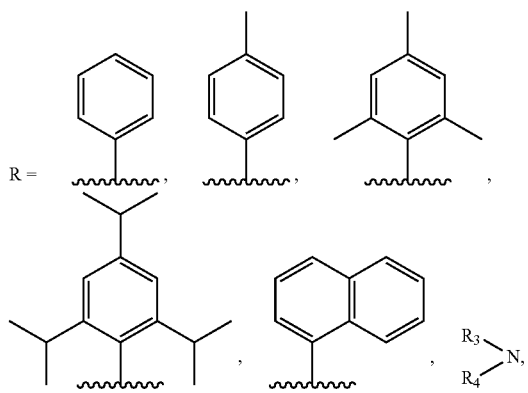

$C_1$-$C_3$ linear or branched alkyl,

R$_1$ and R$_2$ are the same or different and selected from $C_1$ to $C_{18}$ linear or branched alkyl, R$_3$ and R$_4$ are the same or different and selected from $C_1$ to $C_4$ linear or branched alkyl, $CF_3$, $OR_5$ where R$_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl groups of R may be substituted or unsubstituted X=halogen, and

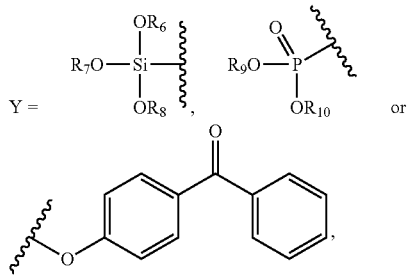

wherein R$_6$, R$_7$, R$_8$, R$_9$ and R$_{10}$ are the same or different and selected from $C_1$ to $C_6$ linear or branched alkyl, wherein the phenyl groups of the benzophenone may be substituted or unsubstituted, and an environmentally friendly carrier. In a preferred embodiment halogen is selected from the group consisting of Cl, Br and I. In a preferred embodiment, R$_1$ and R$_2$ are the same and selected from methyl, ethyl, n-propyl or isopropyl groups, more preferably methyl groups. In a preferred embodiment, R$_3$ and R$_4$ are the same and selected from methyl, ethyl, n-propyl or isopropyl groups, more preferably methyl groups. In a preferred embodiment, l is selected from 1, 2 or 3, more preferably 1. In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, $R_6$, $R_7$ and $R_8$ are the same and selected from methyl, ethyl, n-propyl or isopropyl groups, more preferably methyl groups. In a preferred embodiment, $R_9$ and $R_{10}$ are the same and selected from methyl, ethyl, n-propyl or isopropyl groups, more preferably isopropyl groups.

According to yet another aspect of the present disclosure there is provided a method of reducing growth of at least one microbe on a substrate, preferably a surface, treated with an antimicrobial composition comprising at least one compound selected from the group consisting of 3-(4-benzoylphenoxy)-N,N-dimethyl-N-(3-(2,4,6-trimethylphenylsulfonamido)propyl)propan-1-aminium bromide, 3-(4-benzoylphenoxy)-N,N-dimethyl-N-(3-(4-methylphenylsulfonamido) propyl)propan-1-aminium bromide, 3-(4-benzoylphenoxy)-N,N-dimethyl-N-(3-(phenyl sulfonamido)propyl)propan-1-aminium bromide, 3-(4-benzoylphenoxy)-N,N-dimethyl-N-(3-(naphthalene-1-sulfonamido)propyl)propan-1-aminium bromide, N,N-dimethyl-3-(trimethoxy silyl)-N-(3-(2,4,6-trimethylphenylsulfonamido)propyl)propan-1-aminium chloride, N,N-dimethyl-3-(4-methylphenylsulfonamido)-N-(3-(trimethoxysilyl)propyl)propan-1-aminium chloride, N,N-dimethyl-3-(phenylsulfonamido)-N-(3-(trimethoxysilyl)propyl)propan-1-aminium chloride N,N-dimethyl-3-(naphthalene-1-sulfonamido)-N-(3-(trimethoxysilyl)propyl) propan-1-aminium chloride, and combinations thereof. In a preferred embodiment, the at least one microbe is selected from the group consisting of Listeria monocytogenes, Arthrobacter, Staphylococcus aureus, Pseudomonas aeruginosa, Escherichia coli and combinations thereof.

According to yet another aspect of the present disclosure there is provided a use of an antimicrobial composition comprising a compound of formula (I):

(I)

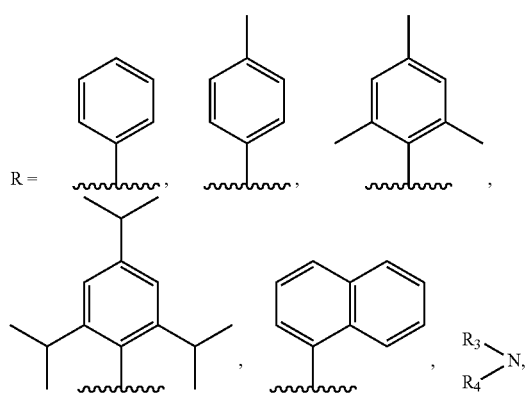

wherein

R =

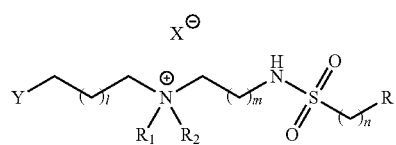

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl groups of R may be substituted or unsubstituted, X=halogen, and Y =
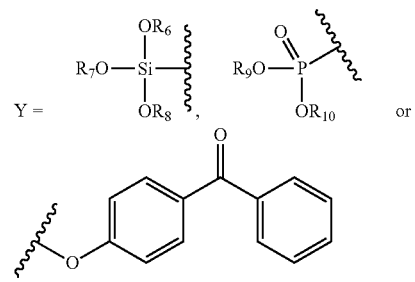

wherein $R_6$, $R_7$, $R_8$, $R_9$ and $R_{10}$ are the same or different and selected from $C_1$ to $C_6$ linear or branched alkyl, wherein the phenyl groups of the benzophenone may be substituted or unsubstituted, to protect a substrate from bio-fouling. In a preferred embodiment, the halogen is selected from the group consisting of Cl, Br and I. In a preferred embodiment, $R_1$ and $R_2$ are the same and selected from methyl, ethyl, n-propyl or isopropyl groups, more preferably methyl groups. In a preferred embodiment, $R_3$ and $R_4$ are the same and selected from methyl, ethyl, n-propyl or isopropyl groups, more preferably methyl groups. In a preferred embodiment, l is selected from 1, 2 or 3, more preferably 1. In a preferred embodiment, $R_5$ is selected from methyl, ethyl, n-propyl or isopropyl groups, more preferably methyl. In a preferred embodiment, m is selected from 1, 2 or 3, more preferably 2. In a preferred embodiment, n is selected from 0, 1, 2 or 3, more preferably 0. In a preferred embodiment, $R_6$, $R_7$ and $R_8$ are the same and selected from methyl, ethyl, n-propyl or isopropyl groups, more preferably methyl groups. In a preferred embodiment, $R_9$ and $R_{10}$ are the same and selected from methyl, ethyl, n-propyl or isopropyl groups, more preferably isopropyl groups. In a preferred embodiment, the bio-fouling is caused by a biofilm.

According to yet another aspect of the present disclosure there is provided a quaternary ammonium di-sulfonamide compound of the formula (VI):

(VI)

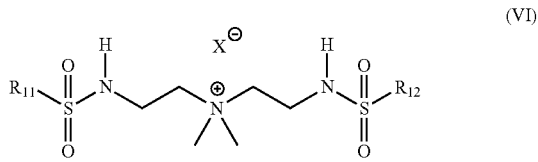

wherein $R_{11}$ and $R_{12}$ are the same or different and are selected from the group consisting of:

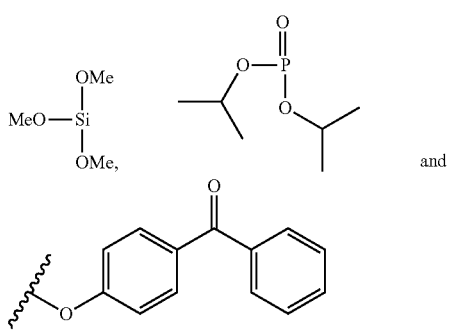

and X is halogen.

In a preferred embodiment, the halogen is selected from the group consisting of Cl, Br and I. In a preferred embodiment, $R_{11}$ and $R_{12}$ are the same and

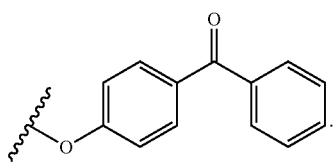 [SMILES: *Oc1ccc(C(=O)c2ccccc2)cc1]

In yet another aspect of the disclosure there is provided a use of a compound of formula (I)

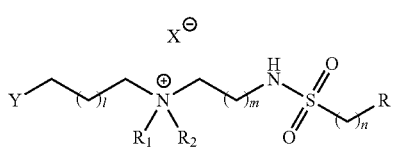

wherein

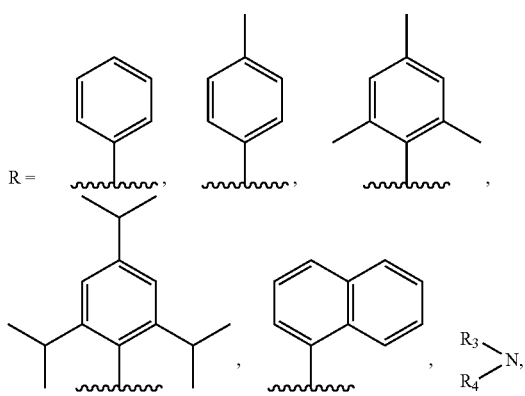

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, wherein the aryl rings of R may be substituted or unsubstituted, X=halogen, and

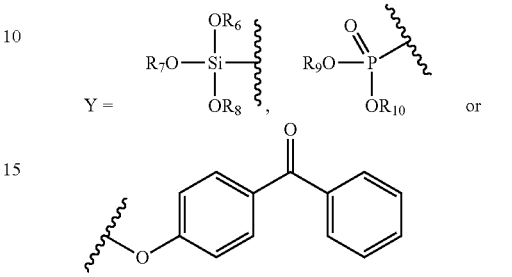

wherein $R_6$, $R_7$, $R_8$, $R_9$ and $R_{10}$ are the same or different and selected from $C_1$ to $C_6$ linear or branched alkyl, wherein the phenyl groups of the benzophenone may be substituted or unsubstituted, for reducing bacterial growth on a solid/air interface.

Further and other aspects will be appreciated by the skilled reader.

DETAILED DESCRIPTION

A series of alkyl and aryl, UV and heat curable quaternary ammonium sulfonamide antimicrobials may be prepared by both conventional and microwave synthesis. Common to all the UV curable compounds is the sulfonamide linkage, the quaternary ammonium site and the benzophenone linker moiety. Additionally, compounds containing a silane linker, preferably for attaching to porous substrates and the like, or a phosphonate linker, preferably for attaching to metal substrates and the like, may be prepared using similar techniques.

These materials may be designed with dual functionality: 1) a functional anchoring group that grafts selectively to porous or non-porous substrates and 2) a quaternary ammonium charge and sulfonamide linkage for attracting bacteria, preferably harmful bacteria and kill them, for example, by mechanical means operating at the solid/air interface.

The term quaternary ammonium sulfonamide refers to quaternary ammonium compounds that have been substituted with a sulfonamide group R—S(=O)$_2$— wherein

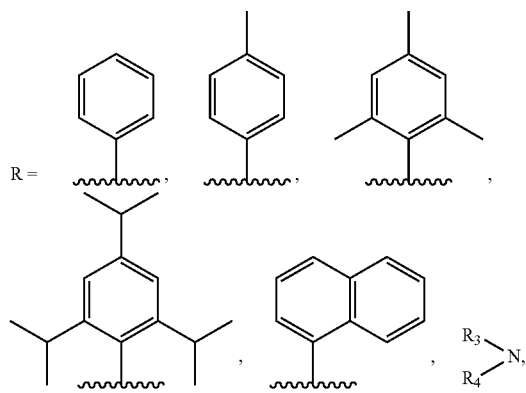

$C_1$-$C_3$ linear or branched alkyl, wherein the aryl rings of R may be substituted or unsubstituted, wherein $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, and the sulfonamide moiety is linked to the quaternary ammonium nitrogen centre by a carbon atom chain, preferably a saturated chain, more preferably a three carbon chain, most preferably a saturated three carbon chain.

The term polar, aprotic solvent means a solvent that has a dipole moment but does not have an acidic hydrogen. Non-limiting examples include acetonitrile, dimethylformamide, dimethylsulfoxide and dichloromethane.

The quaternary ammonium sulfonamide compounds presently disclosed utilize a covalently bound linkage to metal (phosphonate linkage), plastics (UV curable benzophenone linkage) or textiles and glass (silane linkage) and sulfonamide functionality along with a quaternary ammonium salt that renders these materials antimicrobial. Antimicrobial coating compositions of these compounds may be formulated as an alcohol-based, water/alcohol or water based formulations. The use of such solvent systems make these compositions non-toxic, low cost, with minimum impact to the environment and may be applied by electrospray or traditional painting techniques.

These formulations require no photoinitiator in order to graft the quaternary ammonium sulfonamide compounds to substrates. These antimicrobial coating compositions may be sprayed, aerosolized or painted on to non-porous and porous surfaces, allowed to dry and are then actively grafted or cured (covalently attached) to these substrates via low heat, air or UV irradiation to form self-assembled monolayers. These cured antimicrobial coatings form durable bonds to these hard-to-stick-to-surfaces and as a result may inhibit biofilm formation at solid/air interface. The solid/air interface is where many biofilms, and the harmful bacteria that can reside in them, exist. These formulations are non-leaching and water-based and may provide effective preventative protection against harmful bacteria. These compounds work at a solid/air interface where desiccant tolerant pathogenic bacteria can persist where individual or colonizing bacteria flourish.

The antimicrobial quaternary ammonium sulfonamide compounds of the present disclosure may be applied to protect a variety of porous and non-porous substrates, preferably surfaces. In one embodiment, benzophenone-attachment compounds may be attached, for example, to polymers including polyethylene and polypropylene; silane-attachment compounds may be attached, for example, to cellulosic fibres and textiles including cotton and cotton blends; and phosphonate-attachment compounds may be attached, for example, to metal and metal oxide substrates, composites and glasses. The substrate attached terminated sulfonamide containing quaternary ammonium salts form a protective self-assembled monolayer that is 1-2 molecules thick at the substrate. These protective coatings may find applications where antimicrobial substrates are required, in particular, biomedical applications.

In one preferred embodiment, coating of a polymer substrate was achieved by first dissolving the quaternary salt in 10:90 solution of ethanol:water, followed by electrostatic spraying (2×), and a short 30 sec UV cure cycle.

Microbiological assessment of antimicrobial quaternary ammonium sulfonamide coated substrates of the present disclosure reveal them to be highly potent.

With reference to FIG. 1, the presence of benzophenone-anchored quaternary ammonium sulfonamide on polystyrene, polyethylene, polyvinyl chloride and polyether ether ketone coupons was confirmed by bromophenol blue indicator. Darker coloured samples indicate the presence of benzophenone-anchored quaternary ammonium sulfonamide versus lighter coloured untreated samples.

Figure 2:
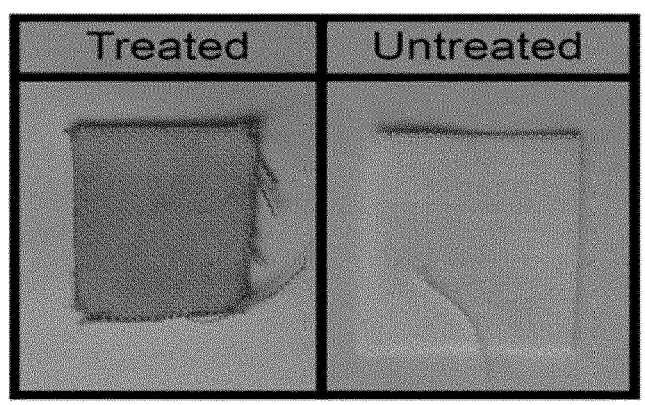
FIG. 2 shows an image of cotton fabric samples before (light coloured) and after (dark coloured) treatment with silane-anchored sulfonamide quat antimicrobial compound.

With reference to FIG. 2, the presence of silane-anchored quaternary ammonium sulfonamide on cotton fabric samples was confirmed by bromophenol blue indicator. The light coloured sample shows no treatment; the darker coloured sample shows treatment.

Figure 3:
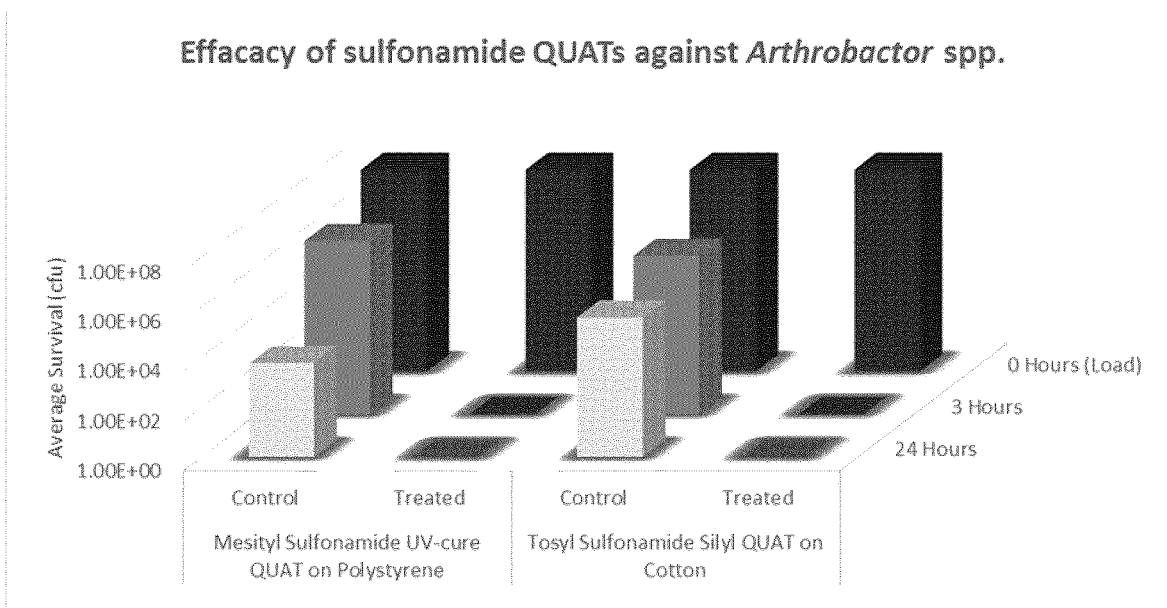
FIG. 3 shows a graph of the dry-surface change in log (colony forming units) over time upon exposure of untreated control and 3-(4-benzoylphenoxy)-N,N-dimethyl-N-(3-(2,4,6-trimethylphenylsulfonamido)propyl)propan-1-aminium bromide treated polystyrene and N,N-dimethyl-3-(4-methylphenylsulfonamido)-N-(3-(trimethoxysilyl)propyl)propan-1-aminium chloride treated cotton to *Arthrobacter* spp.

With reference to FIG. 3, polystyrene untreated and treated with 3-(4-benzoylphenoxy)-N,N-dimethyl-N-(3-(2,4,6-trimethylphenylsulfonamido)propyl)propan-1-aminium bromide, and cotton untreated and treated with N,N-dimethyl-3-(4-methylphenylsulfonamido)-N-(3-(trimethoxysilyl)propyl)propan-1-aminium chloride were inoculated with *Arthrobacter* spp. All bacteria on both treated samples were eradicated within three hours compared to the control. See Example 34 for data.

Figure 4:
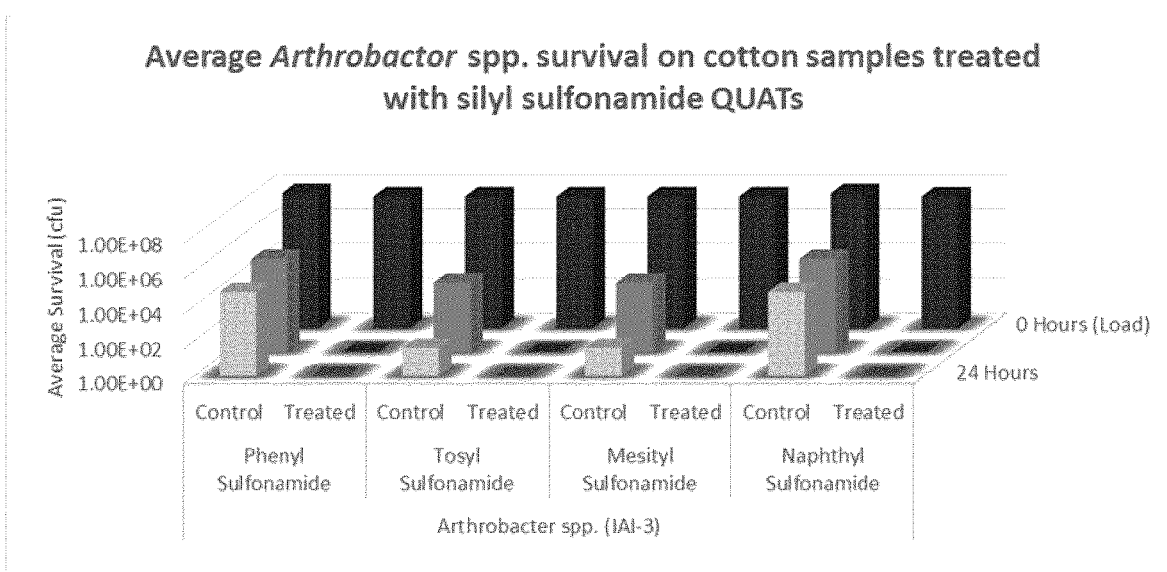
FIG. 4 shows a graph of the dry-surface change in log (colony forming units) over time upon exposure of untreated control and N,N-dimethyl-3-(phenylsulfonamido)-N-(3-(trimethoxysilyl)propyl)propan-1-aminium chloride, N,N-dimethyl-3-(4-methylphenyl sulfonamido)-N-(3-(trimethoxysilyl)propyl)propan-1-aminium chloride, N,N-dimethyl-3-(tri methoxysilyl)-N-(3-(2,4,6-trimethylphenylsulfonamido)propyl)propan-1-aminium chloride and N,N-dimethyl-3-(naphthalene-1-sulfonamido)-N-(3-(trimethoxysilyl)propyl)propan-1-aminium chloride treated cotton to *Arthrobacter* spp.

With reference to FIG. 4, cotton untreated and treated with N,N-dimethyl-3-(phenylsulfonamido)-N-(3-(trimethoxysilyl)propyl)propan-1-aminium chloride, N,N-dimethyl-3-(4-methylphenylsulfonamido)-N-(3-(trimethoxysilyl)propyl)propan-1-aminium chloride, N,N-dimethyl-3-(trimethoxysilyl)-N-(3-(2,4,6-trimethylphenylsulfonamido)propyl)propan-1-aminium chloride or N,N-dimethyl-3-(naphthalene-1-sulfonamido)-N-(3-(trimethoxysilyl)propyl)propan-1-aminium chloride were inoculated with *Arthrobacter* spp. All bacteria on all four samples were eradicated within three hours compared to the control. See Example 34 for data.

Figure 5:
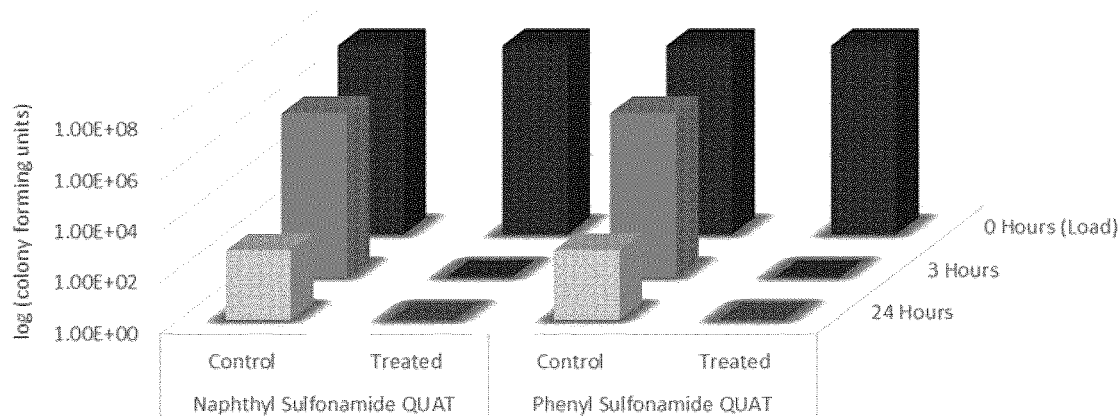
FIG. 5 shows a graph of the dry-surface change in log (colony forming units) over time upon exposure of untreated control and 3-(4-benzoylphenoxy)-N,N-dimethyl-N-(3-(naphthalene-1-sulfonamido)propyl)propan-1-aminium bromide and 3-(4-benzoylphenoxy)-N,N-dimethyl-N-(3-(phenylsulfonamido)propyl)propan-1-aminium bromide treated polyethylene to *Arthrobacter* spp.

With reference to FIG. 5, polyethylene coupons untreated and treated with 3-(4-benzoylphenoxy)-N,N-dimethyl-N-(3-(naphthalene-1-sulfonamido)propyl)propan-1-aminium bromide or 3-(4-benzoylphenoxy)-N,N-dimethyl-N-(3-(phenylsulfonamido)propyl)propan-1-aminium bromide were inoculated with *Arthrobacter* spp. All bacteria on both samples were eradicated within three hours compared to the control. See Example 34 for data.

Figure 6:
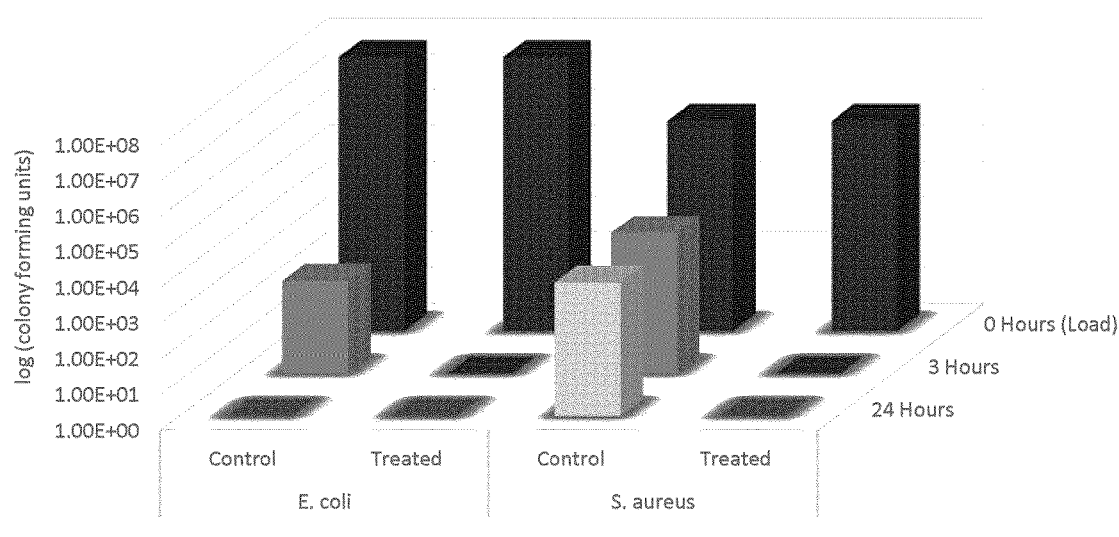
FIG. 6 shows a graph of the dry-surface change in log (colony forming units) over time upon exposure of untreated control and 3-(4-benzoylphenoxy)-N,N-dimethyl-N-(3-(2,4,6-trimethylphenylsulfonamido)propyl)propan-1-aminium bromide treated polyethylene to *E. coli* and *S. aureus*.

With reference to FIG. 6, polyethylene coupons untreated and treated with 3-(4-benzoylphenoxy)-N,N-dimethyl-N-(3-(2,4,6-trimethylphenylsulfonamido)propyl)propan-1-aminium bromide were inoculated with *E. coli* or *S. aureus*. All bacteria were eradicated within three hours compared to the control. See Example 34 for data.

Figure 7:
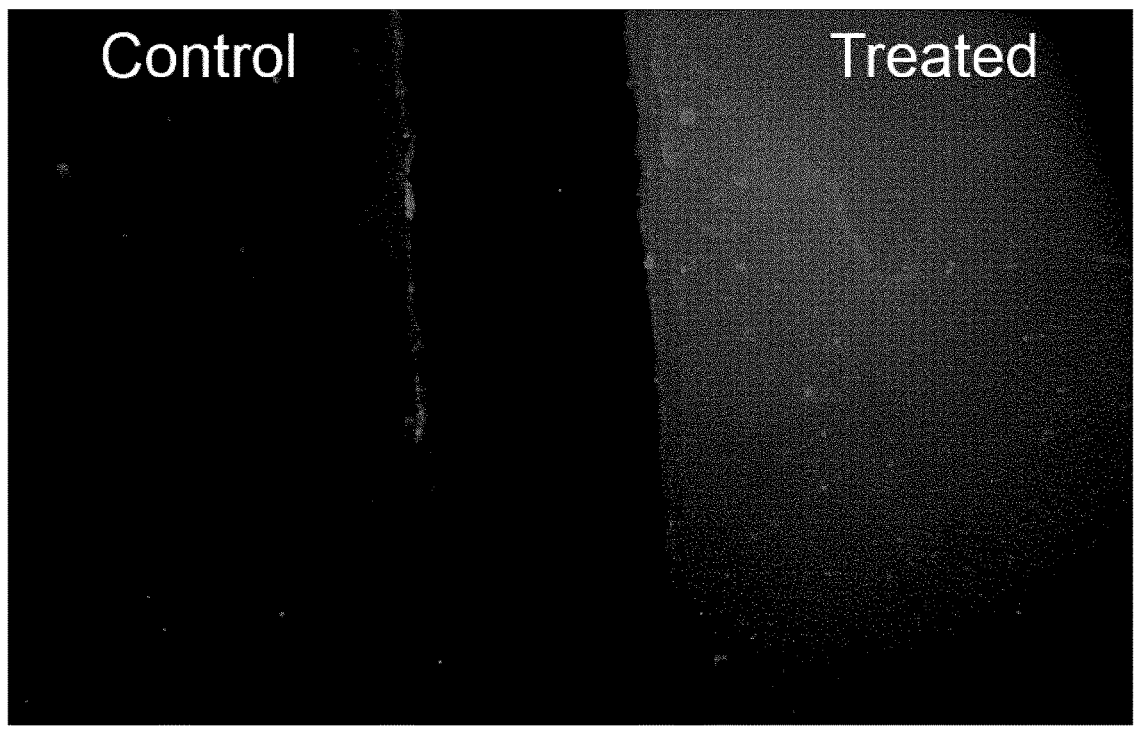
FIG. 7 shows an image of polyethylene samples before (control) and after (treated) treatment with 3-(4-benzoylphenoxy)-N,N-dimethyl-N-(3-(2,4,6-trimethylphenylsulfonamido)propyl) propan-1-aminium bromide containing trace (0.05% w/v) fluorophore.

With reference to FIG. 7, the presence of 3-(4-benzoylphenoxy)-N,N-dimethyl-N-(3-(2,4,6-trimethylphenylsulfonamido)propyl)propan-1-aminium bromide containing a trace (0.05% w/v) of fluorophore on polyethylene coupons was confirmed by UV imaging. The dark sample shows no treatment; the light sample shows treatment.

Figure 8:
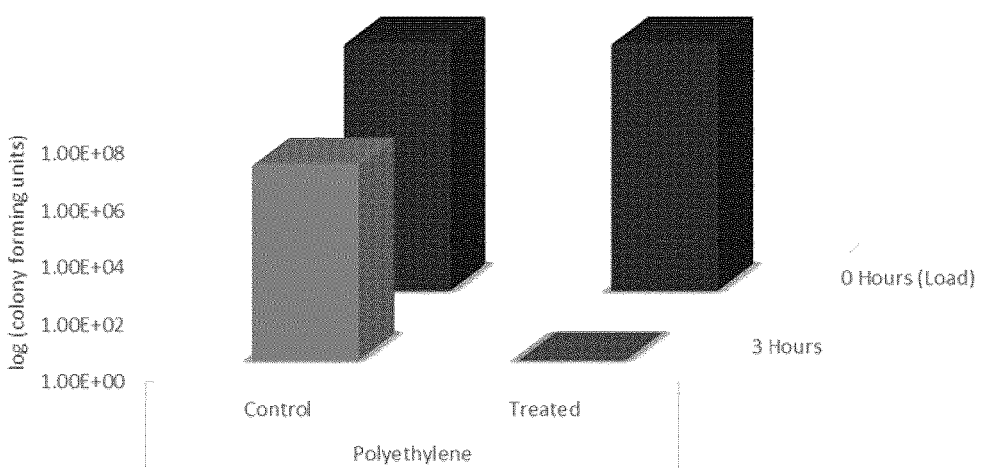
FIG. 8 shows a graph of the dry-surface change in log (colony forming units) over time upon exposure of untreated control and antimicrobial compound 3-(4-benzoylphenoxy)-N,N-dimethyl-N-(3-(2,4,6-trimethylphenylsulfonamido)propyl)propan-1-aminium bromide containing 0.05% w/v fluorophore compound treated polyethylene to *Arthrobacter* spp.

With reference to FIG. 8, polyethylene coupons untreated and treated with 3-(4-benzoylphenoxy)-N,N-dimethyl-N-(3-(2,4,6-trimethylphenylsulfonamido)propyl)propan-1-aminium bromide containing 0.05% w/v fluorophore were inoculated with *Arthrobacter* spp. All bacteria were eradicated within three hours compared to the control. See Example 34 for data.

Figure 9:
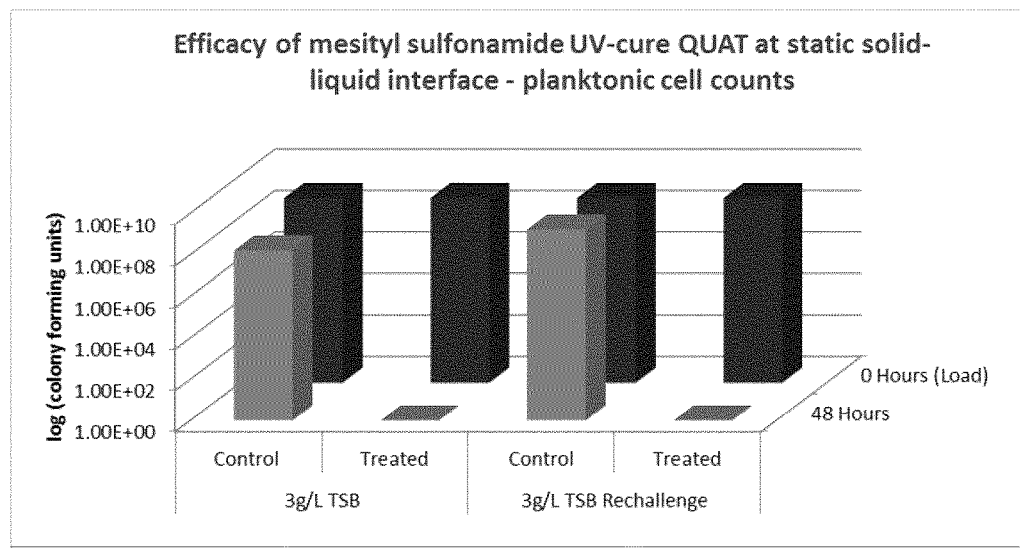
FIG. 9 shows a graph of the solid-liquid interface change in log (colony forming units) over 48 hours exposure of untreated control and 3-(4-benzoylphenoxy)-N,N-dimethyl-N-(3-(2,4,6-trimethylphenylsulfonamido)propyl)propan-1-aminium bromide treated polyethylene test tubes to *Arthrobacter* spp., and planktonic cell survival.

With reference to FIG. 9, the interior of polyethylene test tubes was coated with 3-(4-benzoylphenoxy)-N,N-dimethyl-N-(3-(2,4,6-trimethylphenylsulfonamido)propyl)propan-1-aminium bromide and inoculated with *Arthrobacter* spp. and planktonic cells were sampled after 48 hours incubation and agitation. Biofilm presence was assessed after washing out the growth media and inoculant. Re-challenge to determine whether the antimicrobial effect persisted after repeated exposure was performed. In both cases, there was complete eradication of planktonic cells. See Example 35 for data.

Figure 10:
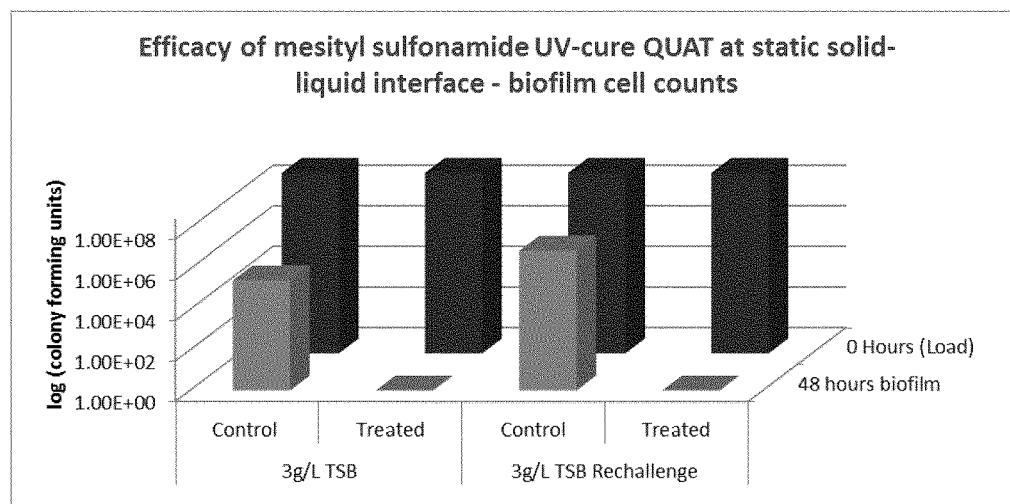
FIG. 10 shows a graph of the solid-liquid interface change in log (colony forming units) over 48 hours exposure of untreated control and 3-(4-benzoylphenoxy)-N,N-dimethyl-N-(3-(2,4,6-trimethylphenylsulfonamido)propyl)propan-1-aminium bromide treated polyethylene test tubes to *Arthrobacter* spp., and biofilm cell survival.

With reference to FIG. 10, the same test as in FIG. 9 was performed to assess biofilm cell survival. After 48 hours biofilm cells were eradicated. See Example 35 for data.

The following non-limiting examples are provided.
Acronyms:
ACN—acetonitrile
DCM—dichloromethane
Et$_2$O—diethyl ether
Et$_3$N—triethylamine
QAC, QUAT—quaternary ammonium compound
TSB—tryptic soy broth General Method 1 Aromatic Sulfonamides Precursor To a flame dried, round bottom flask on ice bath equipped with a stir bar containing 40-50 mL of anhydrous DCM, 1.0 equivalent of respective sulfonyl chloride was added followed by 1.5 equivalents of Et$_3$N, and dropwise addition of 1.5 equivalents of 3-(dimethylamino)propylamine. The reaction mixture was taken off ice bath and allowed to stir for the indicated time at room temperature. The reaction was then transferred to a separatory funnel and extracted with a 30-70 mL of distilled water. Volatiles and/or solvent were removed from the organic phase using a rotary evaporator followed by drying under 10$^{-3}$ mm Hg vacuum.

Scheme 1: General reaction for aromatic sulfonamide precursor

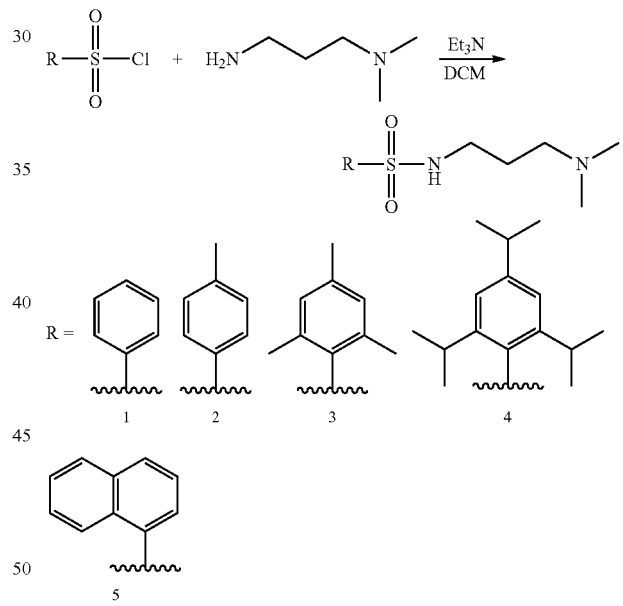

General Method 2 Aliphatic Sulfonamides

To a flame dried, round bottom flask on ice bath equipped with a stir bar containing 40-50 mL of anhydrous DCM, 1.0 equivalent of 3-(dimethylamino)propylamine was added followed by drop wise addition of the respective sulfonyl chlorides (1.0 equivalents). The reaction mixture was taken off ice bath and allowed to stir for 3-5 hours at room temperature. Upon completion the reaction solvent was evaporated using rotary evaporator, the resultant residue was then dissolved in an appropriate amount of potassium carbonate solution (0.05 M) and extracted using 40-60 mL of DCM. Volatiles and/or solvent were removed from the organic phase using a rotary evaporator followed by drying under 10$^{-3}$ mm Hg vacuum.

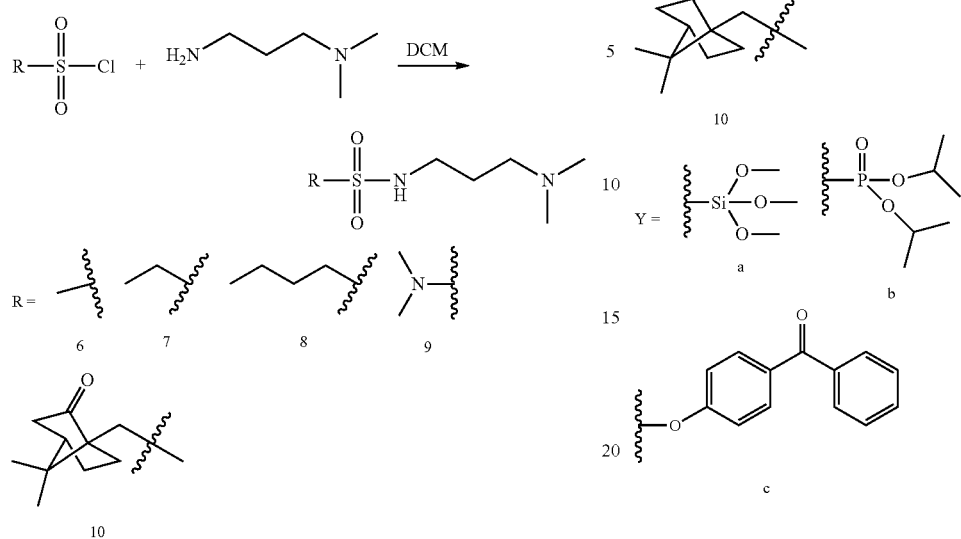

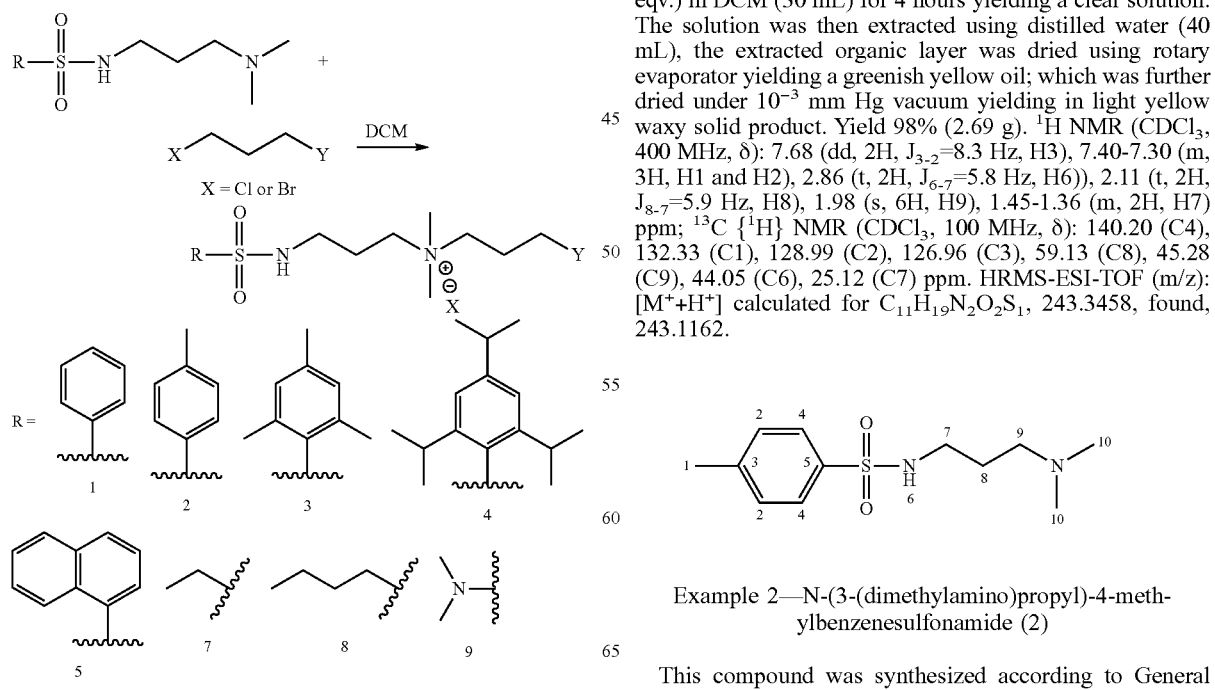

General Method 3 Sealed Tube Menschutkin Quaternization Reactions

In a 20 mL scintillation/microwave vial 1.0 equivalent of the sulfonamide was added followed by addition of 1.0-1.5 equivalents of respective linker group (Silane, phosphonate, or benzophenone) along with a magnetic stir bar and sealed with a screw cap. The reaction mixture was heated using an oil bath at 110° C. for 3-48 hours. The crude material was purified by addition of Et$_2$O (10-30 mL) directly into the reaction mixture followed by decanting (Et$_2$O wash×3) and dried under 10$^{-1}$ mm Hg vacuum.

Synthesis of Aromatic Sulfonamides

Example 1—N-(3-(dimethylamino)propyl)benzenesulfonamide (1)

This compound was synthesized according to General Method 1 using benzenesulfonyl chloride (1.4 mL, 11.32 mmol), triethylamine (2.4 mL, 16.99 mmol, 1.5 eqv.), and 3-(dimethylamino)propylamine (2.1 mL, 16.99 mmol, 1.5 eqv.) in DCM (30 mL) for 4 hours yielding a clear solution. The solution was then extracted using distilled water (40 mL), the extracted organic layer was dried using rotary evaporator yielding a greenish yellow oil; which was further dried under 10$^{-3}$ mm Hg vacuum yielding in light yellow waxy solid product. Yield 98% (2.69 g). $^1$H NMR (CDCl$_3$, 400 MHz, δ): 7.68 (dd, 2H, J$_{3-2}$=8.3 Hz, H3), 7.40-7.30 (m, 3H, H1 and H2), 2.86 (t, 2H, J$_{6-7}$=5.8 Hz, H6)), 2.11 (t, 2H, J$_{8-7}$=5.9 Hz, H8), 1.98 (s, 6H, H9), 1.45-1.36 (m, 2H, H7) ppm; $^{13}$C {$^1$H} NMR (CDCl$_3$, 100 MHz, δ): 140.20 (C4), 132.33 (C1), 128.99 (C2), 126.96 (C3), 59.13 (C8), 45.28 (C9), 44.05 (C6), 25.12 (C7) ppm. HRMS-ESI-TOF (m/z): [M$^+$+H$^+$] calculated for C$_{11}$H$_{19}$N$_2$O$_2$S$_1$, 243.3458, found, 243.1162.

Example 2—N-(3-(dimethylamino)propyl)-4-methylbenzenesulfonamide (2)

This compound was synthesized according to General Method 1 using p-toluenesulfonyl chloride (10.505 g, 55.10 mmol), triethylamine (11.5 mL, 82.65 mmol, 1.5 eqv.), and 3-(dimethylamino)propylamine (10.4 mL, 82.65 mmol, 1.5 eqv.) in DCM (100 mL) for 4 hours yielding a milky white solution. The solution was then extracted using distilled water (100 mL), the extracted organic layer was dried using rotary evaporator yielding a pale yellow oil; which was further dried under $10^{-3}$ mm Hg vacuum yielding in pale white waxy solid product. Yield 98% (13.85 g). $^1$H NMR (CDCl$_3$, 400 MHz, δ): 7.73 (d, 2H, $J_{4-2}$=8.3 Hz, H4), 7.29 (d, 2H, $J_{2-4}$=7.9 Hz, H2), 3.03 (t, 2H, $J_{7-8}$=5.8 Hz, H7), 2.42 (s, 3H, H1), 2.29 (t, 2H, $J_{9-8}$=5.8 Hz, H9), 2.16 (s, 6H, H10), 1.62-1.53 (m, 2H, H8) ppm; $^{13}$C {$^1$H} NMR (CDCl$_3$, 100 MHz, δ): 142.83 (C5), 137.11 (C3), 129.44 (C2), 126.88 (C4), 58.76 (C9), 45.15 (C10), 43.65 (C7), 25.23 (C8), 21.32 (C1) ppm. HRMS-ESI-TOF (m/z): [M$^+$+H$^+$] calculated for C$_{12}$H$_{21}$N$_2$O$_2$S$_1$, 257.3723, found, 257.1322.

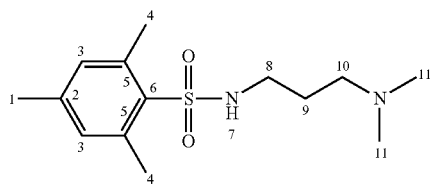

Example 3—N-(3-(dimethylamino)propyl)-2,4,6-trimethylbenzenesulfonamide (3)

This compound was synthesized according to General Method 1 using 2,4,6-trimethylbenzene-1-sulfonyl chloride (2 g, 9.14 mmol), triethylamine (1.9 mL, 13.72 mmol, 1.5 eqv.), and 3-(dimethylamino)propylamine (1.7 mL, 13.72 mmol, 1.5 eqv.) in DCM (50 mL) for 3 hours yielding a clear solution. The solution was then extracted using distilled water (75 mL), the extracted organic layer was dried using rotary evaporator yielding a clear oil; which was further dried under $10^{-3}$ mm Hg vacuum yielding in pale white waxy solid product. Yield 98.5% (2.56 g). $^1$H NMR (CDCl$_3$, 400 MHz, δ): 7.04 (br. s, 1H, H7), 6.93 (s, 2H, H3), 2.94 (t, 2H, $J_{8-9}$=5.7 Hz, H8), 2.61 (s, 6H, H4), 2.32 (t, 2H, $J_{10-9}$=5.6 Hz, H10), 2.27 (s, 3H, H1), 2.18 (s, 6H, H11), 1.69-1.56 (m, 2H, H9) ppm; $^{13}$C {$^1$H} NMR (CDCl$_3$, 100 MHz, δ): 141.74 (C6), 139.07 (C2), 133.80 (C5), 131.87 (C3), 59.66 (C10), 45.48 (C11), 43.72 (C8), 24.99 (C9), 22.88 (C4), 20.95 (C1) ppm. HRMS-ESI-TOF (m/z): [M$^+$+H$^+$] calculated for C$_{14}$H$_{25}$N$_2$O$_2$S$_1$, 285.4255, found, 285.1643.

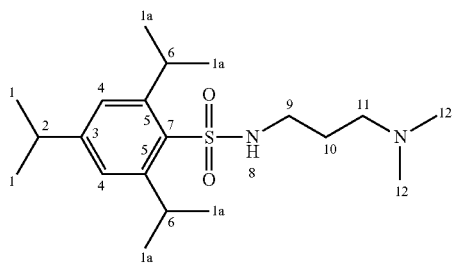 [SMILES: CC(C)c1cc(C(C)C)c(S(=O)(=O)NCCCN(C)C)c(C(C)C)c1]

Example 4—N-(3-(dimethylamino)propyl)-2,4,6-triisopropylbenzenesulfonamide (4)

This compound was synthesized according to General Method 1 using 2,4,6-triisopropylbenzene-1-sulfonyl chloride (2 g, 6.60 mmol), triethylamine (1.4 mL, 9.91 mmol, 1.5 eqv.), and 3-(dimethylamino)propylamine (1.2 mL, 9.91 mmol, 1.5 eqv.) in DCM (50 mL) for 3 hours yielding a clear solution. The solution was then extracted using distilled water (75 mL), the extracted organic layer was dried using rotary evaporater yielding a faint green oil; which was further dried under $10^{-3}$ mm Hg vacuum yielding in pale white waxy solid product. Yield 97% (2.36 g). $^1$H NMR (CDCl$_3$, 400 MHz, δ): 7.15 (s, 2H, H4), 4.23-4.11 (m, 2H, H6), 3.08 (t, 2H, $J_{9-10}$=5.9 Hz, H9), 2.89 (m, 1H, H2), 2.60-2.40 (br. m, 2H, H11), 2.30 (br. s, 6H, H12), 1.83-1.66 (br. m, 2H, H10), 1.29-1.22 (br. m, 18H, H1 and H1a) ppm; $^{13}$C {$^1$H} NMR (CDCl$_3$, 100 MHz, δ): 152.48 (C7), 150.45 (C5), 132.57 (C3), 123.79 (C4), 59.03 (C11), 45.28 (C12), 42.93 (C9), 34.25 (C2), 29.74 (C6), 25.61 (C10), 25.10 (C1a), 23.73 (C1) ppm. HRMS-ESI-TOF (m/z): [M$^+$+H$^+$] calculated for C$_{20}$H$_{37}$N$_2$O$_2$S$_1$, 369.5850, found, 369.2570.

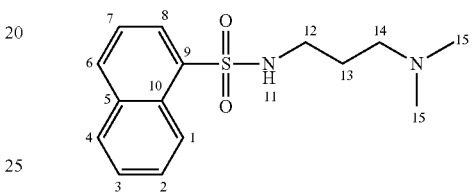

Example 5—N-(3-(dimethylamino)propyl)naphthalene-1-sulfonamide (5)

This compound was synthesized according to General Method 1 using naphthalene-1-sulfonyl chloride (4 g, 18.04 mmol), triethylamine (3.8 mL, 27.06 mmol, 1.5 eqv.), and 3-(dimethylamino)propylamine (3.4 mL, 27.06 mmol, 1.5 eqv.) in DCM (50 mL) for 3 hours yielding a clear solution. The solution was then extracted using distilled water (50 mL), the extracted organic layer was dried using rotary evaporator yielding a greenish yellow oil; which was further dried under $10^{-3}$ mm Hg vacuum yielding in pale white waxy solid product. Yield 99.7% (5.27 g). $^1$H NMR (CDCl$_3$, 400 MHz, δ): 8.67 (d, 1H, $J_{1-2}$=8.5 Hz, H1), 8.25 (d, 1H, $J_{8-7}$=6.2 Hz, H8), 8.05 (d, 1H, $J_7$=8.2 Hz, H6), 7.95 (d, 1H, $J_{4-3}$=7.8 Hz, H4), 7.65 (m, 1H, H2), 7.59 (m, 1H, H3), 7.52 (t, 1H, H7), 2.95 (t, 2H, $J_{12-13}$=5.6 Hz H12), 2.21 (t, 2H, $J_{14-13}$=5.6 Hz, H14), 2.12 (s, 6H, H15), 1.55 (m, 2H, H13) ppm; $^{13}$C {$^1$H} NMR (CDCl$_3$, 100 MHz, δ): 134.85 (C9), 134.45 (C5), 133.96 (C4), 129.79 (C6), 129.16 (C2), 128.42 (C10), 128.21 (C3), 126.82 (C8), 124.76 (C7), 124.28 (C1), 59.80 (C14), 45.56 (C15), 44.77 (C12), 24.68 (C13) ppm. HRMS-ESI-TOF (m/z): [M$^+$+H$^+$] calculated for C$_{15}$H$_{21}$N$_2$O$_2$S$_1$, 293.4044, found, 293.1319.

Synthesis of Aliphatic Sulfonamides

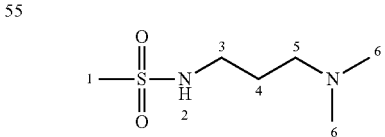

Example 6—N-(3-(dimethylamino)propyl)methanesulfonamide (6)

This compound was synthesized according to General Method 2 using methanesulfonyl chloride (1.4 mL, 17.46 mmol) and 3-(dimethylamino)propylamine (2.2 mL, 17.46 mmol, 1.5 eq.) in DCM (50 mL) for 4 hours and extracted using K$_2$CO$_3$ (0.05 M, 40 mL) yielding in clear oil after drying under 10$^{-3}$ mm Hg vacuum. Yield: 65% (2.05 g). $^1$H NMR (CDCl$_3$, 400 MHz, δ): 3.23 (t, 2H, H3), 2.91 (s, 3H, H1), 2.43 (t, 2H, H5), 2.22 (s, 6H, H6), 1.77-1.65 (m, 2H, H4) ppm; $^{13}$C {$^1$H} NMR (CDCl$_3$, 100 MHz, δ): 59.26 (C5), 45.37 (C6), 44.08 (C3), 39.70 (C1), 25.72 (C4) ppm.

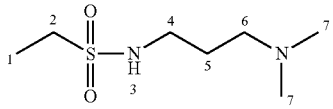

Example 7—N-(3-(dimethylamino)propyl)ethane-sulfonamide (7)

This compound was synthesized according to General Method 2 using ethanesulfonyl chloride (0.7 mL, 7.78 mmol) and 3-(dimethylamino)propylamine (1.5 mL, 11.67 mmol, 1.5 eq.) in DCM (50 mL) for 4 hours and extracted using K$_2$CO$_3$ (0.05 M, 50 mL) yielding in clear oil after drying under 10$^{-3}$ mm Hg vacuum. Yield: 61% (0.92 g). $^1$H NMR (CDCl$_3$, 400 MHz, δ): 3.19 (t, 2H, J$_{4-5}$=5.8 Hz, H4), 3.0 (q, 2H, J$_{2-1}$=7.4 Hz, H2), 2.42 (t, 2H, J$_{6-5}$=5.8 Hz, H6), 2.22 (s, 6H, H7), 1.75-1.64 (m, 2H, H5), 1.34 (t, 3H, J$_{1-2}$=7.4 Hz, H1) ppm; $^{13}$C {$^1$H} NMR (CDCl$_3$, 100 MHz, δ): 59.33 (C6), 46.05 (C2), 45.41 (C7), 44.11 (C4), 25.91 (C5), 8.35 (C1) ppm. HRMS-ESI-TOF (m/z): [M$^+$+H$^+$] calculated for C$_7$H$_{19}$N$_2$O$_2$S$_1$, 195.1162, found, 195.1167.

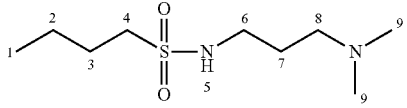

Example 8—N-(3-(dimethylamino)propyl)butane-1-sulfonamide (8)

This compound was synthesized according to General Method 2 using butanesulfonyl chloride (1.7 mL, 12.77 mmol) and 3-(dimethylamino)propylamine (2.4 mL, 19.15 mmol, 1.5 eq.) in DCM (50 mL) for 4 hours and extracted using K$_2$CO$_3$ (0.05 M, 50 mL) yielding in clear oil after drying under 10$^{-3}$ mm Hg vacuum. Yield: 81% (2.31 g). $^1$H NMR (CDCl$_3$, 400 MHz, δ): 3.15 (t, 2H, J$_{6-7}$=5.9 Hz, H6), 2.94 (t, 2H, J$_{4-3}$=7.9 Hz, H4), 2.38 (t, 2H, J$_{8-7}$=5.9 Hz, H8), 2.18 (s, 6H, H9), 7.78-1.61 (m, 4H, H), 1.48-1.34 (m, 2H, H2), 0.91 (t, 3H, J$_{1-2}$=7.3 Hz, H1) ppm; $^{13}$C {$^1$H} NMR (CDCl$_3$, 100 MHz, δ): 59.08 (C8), 51.56 (C4), 45.38 (C9), 43.83 (C6), 26.05 (C3), 25.70 (C7), 21.54 (C2), 13.63 (C1) ppm. HRMS-ESI-TOF (m/z): [M$^+$+H$^+$] calculated for C$_9$H$_{23}$N$_2$O$_2$S$_1$, 223.1475, found, 223.1480.

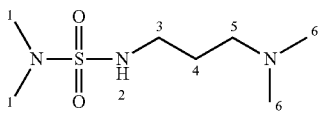

Example 9—N-(2-(dimethylamino)propyl)-N,N-Dimethyl-sulfamide (9)

This compound was synthesized according to General Method 2 using N,N-dimethylsulfamoyl chloride (1.5 mL, 13.93 mmol) and 3-(dimethylamino)propylamine (2.6 mL, 20.89 mmol, 1.5 eq.) in DCM (50 mL) for 4 hours and extracted using K$_2$CO$_3$ (0.05 M, 50 mL) yielding in clear oil after drying under 10$^{-3}$ mm Hg vacuum. Yield: 79.8% (2.33 g). $^1$H NMR (CDCl$_3$, 400 MHz, δ): 3.11 (t, 2H, J$_{3-4}$=6.0 Hz, H3), 2.75 (s, 6H, H1), 2.38 (t, 2H, J$_{5-4}$=6.0 Hz, H5), 2.19 (s, 6H, H6), 1.69-1.61 (m, 2H, H4) ppm. $^{13}$C {$^1$H} NMR (CDCl$_3$, 100 MHz, δ): 59.24 (C5), 45.39 (C6), 44.31 (C3), 38.00 (C1), 25.62 (C4) ppm. HRMS-ESI-TOF (m/z): [M$^+$+H$^+$] calculated for C$_7$H$_{20}$N$_3$O$_2$S$_1$, 210.1271, found, 210.1276.

Example 9A 3-(((1S,4S)-7,7-dimethyl-2-oxobicyclo[2.2.1]heptan-1-yl)methylsulfonamido)-N,N-dimethylpropan-1-aminium chloride

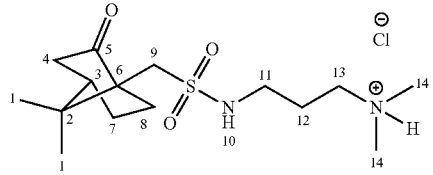 [SMILES: C[NH+](C)CCCNS(=O)(=O)CC12CCC(CC1=O)C2(C)C ; [Cl-]]

This compound was synthesized according to Method 1 using (1 S)-(+)-camphorsulfonyl chloride (20.938 g, 83.75 mmol), and 3-(dimethylamino)propylamine (10.5 mL, 83.75 mmol, 1.0 eqv.) in DCM (50 mL) for 3 hours at room temperature yielding a light yellow cloudy precipitate. The mixture was dried on a rotary evaporated yielding a yellow oil which solidified under a pressurized vacuum system to a pale off white hard solid of the HCl camphor amine salt. Yield 100% (26.151 g, 83.5 mmol). $^1$H NMR (CDCl$_3$, 400 MHz, δ): 5.44 (s, 1H), 4.33 (s, 4H), 3.69 (s, 4H), 3.44 (s, 4H), 2.77 (s, 4H), 2.71 (s, 4H), 2.52-2.48 (m, 8H), 2.43-2.06 (m, 37H), 2.10 (d, J=2.3 Hz, 9H), 2.10 (d, J=2.3 Hz, 7H), 2.04 (s, 5H), 1.86 (s, 3H), 1.74-1.64 (m, 8H), 1.59 (s, 3H), 1.34 (s, 3H), 1.04 (s, 3H, H1), 0.87 (s, 3H, H1) ppm; Agrees well with literature values. (Eur. J. Pharm. Sci. 65 (2014) 29-37).

General Procedure 4 for the Menschutkin Quaternization 1.0 equivalent of sulfonamide containing tertiary amine and 1.0-1.5 equivalents of respective end functionality (silane, phosphorus or benzophenone) halide were mixed in ACN using Method 3 and heated for 3-48 hours. The reaction vial was allowed to cool to RT and the crude product was purified as indicated in Method 3.

Synthesis of Organosilane based QAC

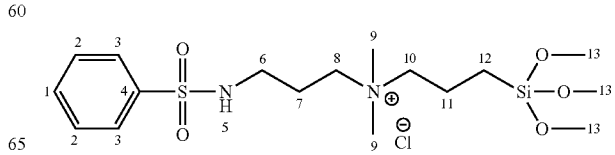

Example 10—N,N-dimethyl-3-(phenylsulfonamido)-N-(3-(trimethoxysilyl)propyl)propan-1-aminium chloride (1a)

This compound was synthesized using N-(3-(dimethylamino)propyl)benzenesulfonamide (1.0 g, 4.13 mmol) and (3-Chloropropyl)trimethoxysilane (1.1 mL, 6.19 mmol, 1.5 eq.) in ACN (3 mL) for 4 hours resulting in viscous golden yellow brown solution. The product was purified using $Et_2O$ (10 mL×3) and obtained as clear golden brown gummy oil after drying under $10^{-3}$ mm Hg vacuum at room temperature. Yield: 97.5% (1.77 g). $^1H$ NMR ($CDCl_3$, 400 MHz, δ): 8.39 (br. S, 1H, H5), 7.96 (d, 2H, H3), 7.54-7.341 (m, 3H, H1 & H2), 3.69-3.62 (m, 2H, H8), 3.51 (s, 9H, H13), 3.37-3.30 (t, 2H, H10), 3.21 (s, 6H, H9), 3.03-2.96 (m, 2H, H6), 2.12-2.015 (m, 2H, H7), 1.80-1.68 (m, 2H, H11), 0.59 (t, 2H, $J_{12-11}$=7.8 Hz, H12) ppm. $^{13}C$ {$^1H$} NMR ($CDCl_3$, 100 MHz, δ): 139.86 (C4), 132.41 (C1), 129.14 (C2), 127.20 (C3), 65.94 (C10), 62.45 (C8), 51.10 (C9), 50.72 (C13), 39.93 (C6), 22.61 (C7), 16.45 (C11), 5.57 (C12) ppm. $^{29}Si$ {$^1H$} NMR (79.4 MHz, $CDCl_3$, δ): −44.41 ppm.

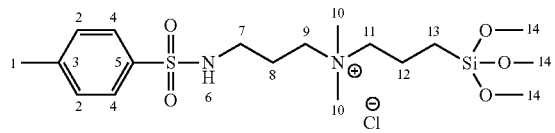

Example 11—N,N-dimethyl-3-(4-methylphenylsulfonamido)-N-(3-(trimethoxysilyl)propyl) propan-1-aminium chloride (2a)

This compound was synthesized using N-(3-(dimethylamino)propyl)-4-methylbenzenesulfonamide (1.0 g, 3.90 mmol) and (3-Chloropropyl)trimethoxysilane (1.1 mL, 5.85 mmol, 1.5 eq.) in ACN (3 mL) for 3.5 hours resulting in viscous golden yellow brown solution. The product was purified using $Et_2O$ (10 mL×3) and obtained as clear golden brown gummy oil after drying under $10^{-3}$ mm Hg vacuum at room temperature. Yield: 97% (1.67 g). $^1H$ NMR ($CDCl_3$, 400 MHz, δ): 8.18 (br. s, 1H, H6), 7.85 (d, 2H, $J_{4-2}$=7.9 Hz, H4), 7.29 (d, 2H, $J_{2-4}$=7.7 Hz, H2), 3.75-3.62 (m, 2H, H9), 3.55 (s, 9H, H14), 3.41-3.32 (m, 2H, H11), 3.25 (s, 6H, H10), 3.08-2.94 (m, 2H, H7), 2.40 (s, 3H, H1), 2.15-2.05 (m, 2H, H8), 1.84-1.58 (m, 2H, H12), 0.63 (t, 2H, $J_{4-2}$=7.7 Hz, H13) ppm. $^{13}C$ {$^1H$} NMR ($CDCl_3$, 100 MHz, δ): 143.08 (C5), 136.85 (C3), 129.70 (C2), 127.85 (C4), 65.82 (C11), 62.45 (C9), 51.10 (C14), 50.70 (C10), 39.91 (C7), 22.66 (C1), 21.46 (C8), 16.44 (C12), 5.57 (C13) ppm. $^{29}Si$ {(H} NMR (79.4 MHz, $CDCl_3$, δ): −44.37 ppm. HRMS-ESI-TOF (m/z): [$M^+$–$Cl^-$] calculated for $C_{18}H_{35}N_2O_5S_1Si_1$, 419.6309, found, 419.2026.

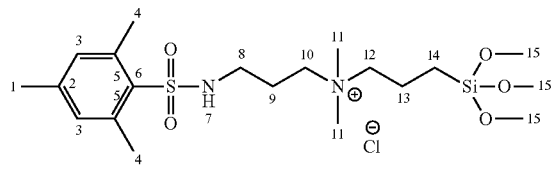

Example 12—N,N-dimethyl-3-(trimethoxysilyl)-N-(3-(2,4,6-trimethylphenylsulfonamido) propyl)propan-1-aminium chloride (3a)

This compound was synthesized using N-(3-(dimethylamino)propyl)-2,4,6-trimethylbenzenesulfonamide (2.0 g, 7.03 mmol) and (3-Chloropropyl)trimethoxysilane (1.9 mL, 10.55 mmol, 1.5 eq.) in ACN (3 mL) for 4.5 hours resulting in viscous golden yellow brown solution. The product was purified using $Et_2O$ (10 mL×3) and obtained as clear golden brown gummy oil after drying under $10^{-3}$ mm Hg vacuum at room temperature. Yield: 92.6% (3.27 g). $^1H$ NMR ($CDCl_3$, 400 MHz, δ): 7.74 (t, 1H, $J_7$=6.0 Hz, H7), 6.90 (s. 2H, H3), 3.70 (t, 2H, $J_{8-9}$=7.9 Hz, H8), 3.53 (s, 9H, H15), 3.40-3.33 (m, 2H, H12), 3.25 (s, 6H, H11), 3.02-2.94 (m, 2H, H10), 2.62 (br. s, 6H, H4), 2.25 (s, 3H, H1), 2.14-2.04 (m, 2H, H9), 1.83-1.72 (m, 2H, H13), 0.62 (t, 2H, $J_{14-13}$=7.9 Hz, H14) ppm. $^{13}C$ {$^1H$} NMR ($CDCl_3$, 100 MHz, δ): 142.01 (C6), 139.22 (C5), 133.83 (C2), 132.01 (C3), 66.06 (C12), 62.51 (C10), 51.22 (C11), 50.81 (C15), 39.33 (C8), 23.28 (C4), 22.88 (C1), 20.95 (C9), 16.57 (C13), 5.70 (C14) ppm. $^{29}Si$ {$^1H$} NMR (79.4 MHz, $CDCl_3$, δ): −44.43 ppm. HRMS-ESI-TOF (m/z): [$M^+$–$Cl^-$] calculated for $C_{20}H_{39}N_2O_5S_1Si_1$, 447.6840, found, 447.2357.

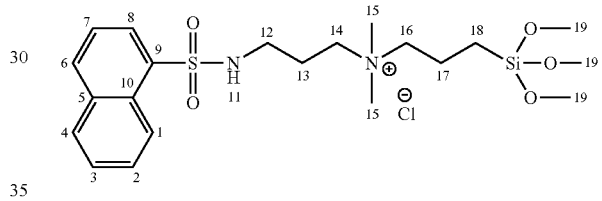

Example 13—N,N-dimethyl-3-(naphthalene-1-sulfonamido)-N-(3-(trimethoxysilyl)propyl)propan-1-aminium chloride (5a)

This compound was synthesized using N-(3-(dimethylamino)propyl)naphthalene-1-sulfonamide (0.5 g, 2.21 mmol) and (3-Chloropropyl)trimethoxysilane (0.6 mL, 3.31 mmol, 1.5 eq.) in ACN (3 mL) for 5 hours resulting in viscous golden yellow brown solution. The product was purified using $Et_2O$ (10 mL×3) and obtained as clear golden brown gummy oil after drying under $10^{-3}$ mm Hg vacuum at room temperature. Yield: 78.8% (0.85 g). $^1H$ NMR ($CDCl_3$, 400 MHz, δ): 8.83 (d, 1H, $J_{8-7}$=8.6 Hz, H8), 8.47 (t, 1H, $J_{11-12}$=5.7 Hz, H11), 8.20 (d, 1H, $J_{6-7}$=7.3 Hz, Hs6), 7.99 (d, 1H, $J_{1-2}$=8.1 Hz, H1), 7.87 (d, 1H, $J_{4-3}$=8.1 Hz, H4), 7.74-7.65 (m, 1H, H7), 7.55-7.46 (m, 2H, H3 & H2), 3.51-3.46 (m, 11H, H14 & H19), 3.22-3.16 (m, 2H, H16), 3.09-3.01 (m, 8H, H12 & H15), 1.98-1.86 (m, 2H, H13), 1.68-1.54 (m, 2H, H17), 0.51 (t, 2H, $J_{18-17}$=7.8 Hz, H18) ppm. $^{13}C$ {$^1H$} NMR ($CDCl_3$, 100 MHz, 5): 135.12 (C9), 134.16 (C5), 133.91 (C1), 129.07 (C6), 128.8 (C4), 128.56 (C7), 128.12 (C10), 127.02 (C3), 125.30 (C8), 124.31 (C2), 65.84 (C16), 62.32 (C14), 50.92 (C15), 50.69 (C19), 39.79 (C12), 22.81 (C13), 16.33 (C17), 5.48 (C18) ppm. $^{29}Si$ {$^1H$} NMR (79.4 MHz, $CDCl_3$, δ): −44.49 ppm. HRMS-ESI-TOF (m/z): [$M^+$–$Cl^-$] calculated for $C_{21}H_{35}N_2O_5S_1Si_1$, 455.2030, found, 455.2018.

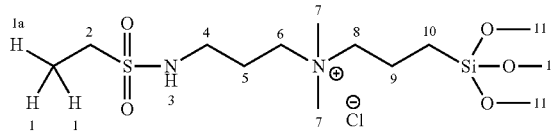

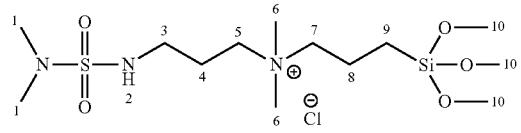

Example 14—3-(ethylsulfonamido)-N,N-dimethyl-N-(3-(trimethoxysilyl)propyl)propan-1-aminium chloride (7a)

This compound was synthesized using N-(3-(dimethylamino)propyl)ethanesulfonamide (1.0 g, 5.15 mmol) and (3-Chloropropyl)trimethoxysilane (1.4 mL, 7.72 mmol, 1.5 eq.) in ACN (3 mL) for 5 hours resulting in viscous golden yellow brown solution. The product was purified using $Et_2O$ (10 mL×3) and obtained as clear golden brown gummy oil after drying under $10^{0.3}$ mm Hg vacuum at room temperature. Yield: 86.0% (1.73 g). $^1$H NMR ($CDCl_3$, 400 MHz, δ): 7.63 (s, 1H, H3), 3.75-3.47 (m, 11H, H6 & H1), 3.39-3.31 (m, 2H, H8), 3.25-3.15 (m, 8H, H7 & H4), 3.07-2.98 (m, 2H, H2), 2.19-2.02 (m, 2H, H5), 1.88-1.69 (m, 2H, H9), 1.31 (td, 3H, $J_{1-2}$=7.3 Hz, $J_{1-1a}$=3.4 Hz, H1 &H1a), 0.62 (t, 2H, $J_{10-9}$=7.8 Hz, H10) ppm. $^{13}$C {$^1$H} NMR ($CDCl_3$, 100 MHz, δ): 65.89 (C8), 62.40 (C6), 51.18 (C7), 50.81 (C11), 46.37 (C2), 40.09 (C4), 23.58 (C5), 16.54 (C9), 8.28 (C1), 5.73 (C10) ppm. $^{29}$Si {$^1$H} NMR (79.4 MHz, $CDCl_3$, δ): −44.51 ppm.

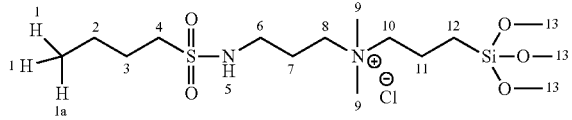

Example 15—3-(butylsulfonamido)-N,N-dimethyl-N-(3-(trimethoxysilyl)propyl)propan-1-aminium chloride (8a)

This compound was synthesized using N-(3-(dimethylamino)propyl)butanesulfonamide (1.0 g, 4.50 mmol) and (3-Chloropropyl)trimethoxysilane (1.2 mL, 6.75 mmol, 1.5 eq.) in ACN (3 mL) for 5 hours resulting in viscous golden yellow brown solution. The product was purified using $Et_2O$ (10 mL×5) and obtained as clear golden brown gummy oil after drying under $10^{-1}$ mm Hg vacuum at room temperature. Yield: 60.0% (1.13 g). $^1$H NMR ($CDCl_3$, 400 MHz, δ): 7.62 (br. s, 1H, H5), 3.67-3.60 (m, 2H, H8), 3.51 (s, 9H, H13), 3.36-3.29 (m, 2H, H4), 2.15-2.04 (m, 2H, H7), 1.83-1.66 (m, 4H, H11 & H3), 1.41-1.33 (m, 2H, H2), 0.87 (td, $J_{1-2}$=7.3 Hz, $J_{1-1a}$=3.1 Hz, H1 & H1a), 0.60 (t, 2H, $J_{12-11}$=7.3 Hz, H12) ppm. $^{13}$C {$^1$H} NMR ($CDCl_3$, 100 MHz, δ): 65.82 (C10), 51.81 (C4), 51.12 (C9), 50.74 (C13), 40.04 (C6), 25.38 (C3), 23.50 (C7), 21.58 (C2), 16.50 (C11), 13.62 (C1), 5.68 (C12) ppm. $^{29}$Si {$^1$H} NMR (79.4 MHz, $CDCl_3$, δ): −44.50 ppm. HRMS-ESI-TOF (m/z): [M$^+$−Cl$^-$] calculated for $C_{15}H_{37}N_2O_5S_1Si_1$, 385.2187, found, 385.2185.

Example 16—3-((N,N-dimethylsulfamoyl)amino)-N,N-dimethyl-N-(3-(trimethoxysilyl) propyl)propan-1-aminium chloride (9a)

Synthesis of Organophosphosophorus based QAC

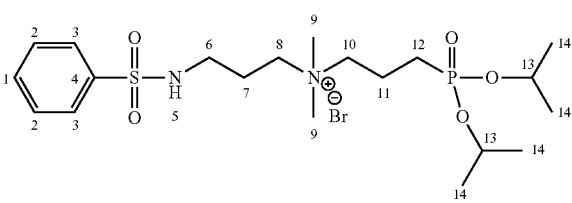 [SMILES: CC(C)OP(=O)(CCC[N+](C)(C)CCCNS(=O)(=O)c1ccccc1)OC(C)C ; [Br-]]

Example 17—3-(diisopropoxyphosphoryl)-N,N-dimethyl-N-(3-(phenylsulfonamido)propyl) propan-1-aminium bromide (1b)

This compound was synthesized using N-(3-(dimethylamino)propyl)benzenesulfonamide (1.0 g, 4.13 mmol) and diisopropyl (3-bromopropyl)phosphonate (1.10 mL, 4.13 mmol, 1 eq.) in ACN (3 mL) for 4 hours resulting in viscous golden yellow brown solution. The product was purified using $Et_2O$ (10 mL×3) and obtained as pale yellow fluffy/gummy powder after drying under $10^{-3}$ mm Hg vacuum at room temperature. Yield: 86.0% (1.87 g). $^1$H NMR ($CDCl_3$, 400 MHz, δ): 7.94 (d, 2H, $J_{3-2}$=6.5 Hz, H3), 7.65 (t, 1H, $J_{5-6}$=5.9 Hz, H5), 7.54-7.46 (m, 3H, H1 & H2), 4.70-4.57 (m, 2H, H13), 3.73-3.65 (m, 2H, H8), 3.64-3.56 (m, 2H, H10), 3.27 (s, 6H, H9), 3.02 (dd, 2H, $J_{6-5}$=11.3 Hz, $J_{6-7}$=5.6 Hz, H6), 2.16-1.94 (m, 4H, (H7, H11, & ACN)), 1.79 (dt, 2H, $J_{12-P}$=17.7 Hz, H8, $J_{12-11}$=7.2 Hz, H12), 1.28 (dd, 12H, $J_{14-P}$=6.2 Hz, H8, $J_{14-13}$=1.7 Hz, H14) ppm. $^{13}$C {$^1$H} NMR ($CDCl_3$, 100 MHz, δ): 139.57 (C4), 132.59 (C2), 129.23 (C1), 127.19 (C3), 70.82 (d, $^2J_{13-P}$=6.7 Hz, C13), 6.74 (d, $^3J_{10-P}$=15.1 Hz, C10), 62.41 (C8), 51.28 (C9), 39.89 (C6), 24.12 (d, $J_{14-P}$=4.5 Hz, C14), 23.99 (d, $J_{14-P}$=4.0 Hz, C14), 23.82 & 22.38 (d, $J_{12-P}$=144.3 Hz, C12), 22.68 (C7), 16.67 (C11) ppm. $^{31}$P{(H} NMR ($CDCl_3$, 121.45 MHz, δ): 27.36 ppm. HRMS-ESI-TOF (m/z): [M$^+$−Br$^-$] calculated for $C_{20}H_{38}N_2O_5P_1S_1$, 449.2234, found, 449.2232.

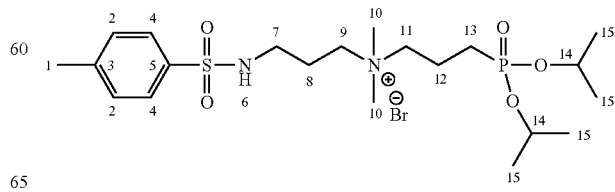

Example 18—3-(diisopropoxyphosphoryl)-N,N-dimethyl-N-(3-(4-methylphenylsulfon amido)propyl)propan-1-aminium bromide (2b)

This compound was synthesized using N-(3-(dimethylamino)propyl)-4-methylbenzenesulfonamide (0.50 g, 1.95 mmol) and diisopropyl (3-bromopropyl)phosphonate (0.50 mL, 1.95 mmol, 1 eq.) in ACN (3 mL) for 3 hours resulting in pale yellow solution with some precipitate formation. The product was purified using $Et_2O$ (10 mL×3) and obtained as white puffy powder after drying under $10^{0.3}$ mm Hg vacuum at room temperature. Yield: 89.5% (0.95 g). $^1$H NMR ($CDCl_3$, 400 MHz, δ): 7.78 (d, 2H, $J_{4-2}$=8.2 Hz, H4), 7.55 (t, 1H, $J_{6-7}$=5.8 Hz, H6), 7.28-7.23 (m, 2H, H2 and $CDCl_3$), 4.72-4.49 (m, 2H, H14), 3.72-3.63 (m, 2H, H9), 3.62-3.54 (m, 2H, H11), 3.25 (s, 6H, H10), 3.00-2.90 (m, 2H, H7), 2.36 (s, 3H, H1), 2.16-1.90 (m, 4H, H8 & H12), 1.75 (dt, 2H, $J_{13-P}$=17.8 Hz, $J_{13-12}$=7.1 Hz, H13), 1.25 (dd, 12H, $J_{15-P}$=56.15 Hz, $J_{15-14}$=2.1 Hz, H15) ppm. $^{13}$C {$^1$H} NMR ($CDCl_3$, 100 MHz, δ): 143.25 (C5), 136.46 (C3), 129.74 (C2), 127.22 (C4), 70.71 (d, $^2J_{14-P}$=6.7 Hz, C14), 63.67 (d, $^3J_{11-P}$=15.8 Hz, C11), 62.42 (C9), 51.17 (C10), 39.86 (C7), 24.10 (d, $J_{15-P}$=4.5 Hz, C15), 23.97 (d, $J_{15-P}$=4.0 Hz, C15), 23.79 & 22.36 (d, $J_{13-P}$=144.1 Hz, C13), 22.52 (C8), 21.47 (C1), 16.69 (d, $^2J_{12-P}$=4.1 Hz, C12) ppm. $^{31}$P {$^1$H} NMR ($CDCl_3$, 121.45 MHz, δ): 27.15 ppm. HRMS-ESI-TOF (m/z): [M$^+$−Br$^-$] calculated for $C_{21}H_{40}N_2O_5P_1S_1$, 463.5909, found, 463.2394.

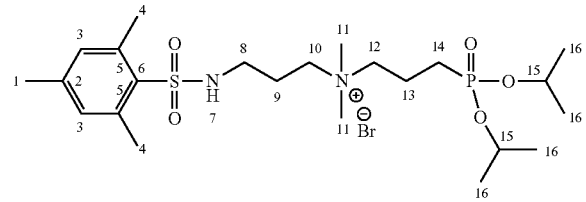 [SMILES: Cc1cc(C)c(S(=O)(=O)NCCC[N+](C)(C)CCCP(=O)(OC(C)C)OC(C)C)c(C)c1 ; [Br-]]

Example 19—3-(diisopropoxyphosphoryl)-N,N-dimethyl-N-(3-(2,4,6-trimethylphenylsulfon amido) propyl)propan-1-aminium bromide (3b)

This compound was synthesized using N-(3-(dimethylamino)propyl)-2,4,6-trimethylbenzenesulfonamide (0.50 g, 1.76 mmol) and diisopropyl (3-bromopropyl)phosphonate (0.40 mL, 1.76 mmol, 1 eq.) in ACN (3 mL) for 4 hours resulting in viscous golden yellow brown solution. The product was purified using $Et_2O$ (10 mL×3) and obtained as pale yellow fluffy/gummy powder after drying under $10^3$ mm Hg vacuum at room temperature. Yield: 71.0% (0.71 g). $^1$H NMR ($CDCl_3$, 400 MHz, δ): 7.14 (t, 1H, $J_7$=6.0 Hz, H7), 6.92 (s, 2H, H3), 4.71-4.57 (m, 2H, H15), 3.84-3.75 (m, 2H, H10), 3.74-3.60 (m, 2H, H12), 3.32 (s, 6H, H11), 3.01 (dd, 2H, $J_{8-7}$=11.2 Hz, $J_{8-9}$=5.6 Hz, H8), 2.63 (s, 6H, H4), 2.27 (s, 3H, H1), 2.22-2.00 (m, 4H, H9 & H13), 1.81 (dt, 2H, $J_{14-P}$=17.8 Hz, $J_{14-13}$=7.0 Hz, H14), 1.30 (d, 12H, $J_{16-15}$=6.2 Hz, H16) ppm. $^{13}$C {$^1$H} NMR ($CDCl_3$, 100 MHz, δ): 142.11 (C6), 139.07 (C2), 133.33 (C5), 132.00 (C3), 70.80 (d, $^2J_{15-P}$=6.7 Hz, C15), 63.68 (d, $^2J_{12-P}$=15.0 Hz, C112), 62.35 (C10), 51.32 (C11), 39.20 (11C8), 24.13 (d, $J_{16-P}$=4.5 Hz, C16), 24.00 (d, $J_{16-P}$=4.0 Hz, C16), 23.81 & 22.38 (d, $J_{14-P}$=144.3 Hz, C14), 23.22 (C4), 22.68 (C9), 20.89 (C1), 16.76 (C13) ppm. $^{31}$P {$^1$H} NMR ($CDCl_3$, 121.45 MHz, δ): 27.16 ppm. HRMS-ESI-TOF (m/z): [M$^+$−Br$^-$] calculated for $C_{23}H_{44}N_2O_5P_1S_1$, 491.2703, found, 491.2693.

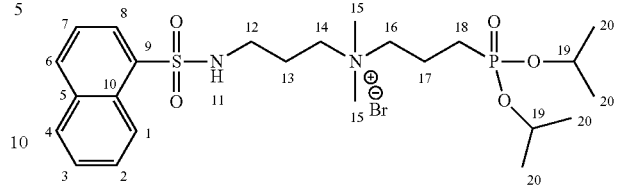

Example 20—3-(diisopropoxyphosphoryl)-N,N-dimethyl-N-(3-(naphthalene-1-sulfonamido) propyl) propan-1-aminium bromide (5b)

This compound was synthesized using N-(3-(dimethylamino)propyl)naphthalene-1-sulfonamide (0.50 g, 4.13 mmol) and diisopropyl (3-bromopropyl)phosphonate (0.50 mL, 3.42 mmol, 1 eq.) in ACN (3 mL) for 5.5 hours resulting in viscous golden yellow brown solution. The product was purified using $Et_2O$ (10 mL×3) and obtained as pale yellow fluffy/gummy powder after drying under $10^{-3}$ mm Hg vacuum at room temperature. Yield: 77.4% (0.77 g). $^1$H NMR ($CDCl_3$, 400 MHz, δ): 8.82 (d, 1H, $J_{6-7}$=8.7 Hz, H8), 8.20 (d, 1H, $J_{6-7}$=7.3 Hz, H6), 8.02 (d, 1H, $J_{1-2}$=8.3 Hz, H1), 7.92-7.84 (m, 2H, H4 & H11), 7.73-7.62 (m, 1H, H7), 7.57-7.48 (m, 2H, H3 & H2), 4.69-4.50 (m, 2H, H19), 3.62-3.47 (m, 4H, H14 & H16), 3.12 (s, 6H, H15), 3.03 (dd, 2H, $J_{12-11}$=11.2 Hz, $J_{12-13}$=5.6 Hz, H12), 2.08-1.82 (m, 7H, (ACN, H13 & H17)), 1.71 (dt, 2H, $J_{18-P}$=17.5 Hz, $J_{18-17}$=7.2 Hz, H18), 1.12 (t, 12H, $J_{20-19}$=6.0 Hz, H20) ppm. $^{13}$C {$^1$H} NMR ($CDCl_3$, 100 MHz, δ): 134.63 (C9), 134.18 (C5), 13.14 (C1), 129.37 (C6), 128.92 (C4), 128.63 (C7), 128.03 (C10), 127.08 (C3), 125.17 (C8), 124.36 (C2), 70.80 (d, $^2J_{19-P}$=6.7 Hz, C19), 63.60 (d, $^3J_{16-P}$=15.1 Hz, C16), 62.36 (C14), 51.14 (C15), 39.74 (C12), 24.12 (d, $J_{20}$-P=4.5 Hz, C20), 23.99 (d, $J_{20-P}$=4.0 Hz, C20), 23.74 & 22.31 (d, $J_{18-P}$=144.5 Hz, C18), 22.68 (C13), 16.65 (d, $^2J_{17-P}$=144.3 Hz, C17) ppm. $^{31}$P{$^1$H} NMR ($CDCl_3$, 121.45 MHz, δ): 27.19 ppm. HRMS-ESI-TOF (m/z): [M$^+$−Br$^-$] calculated for $C_{24}H_{40}N_2O_5P_1S_1$, 499.2390, found, 499.2385.

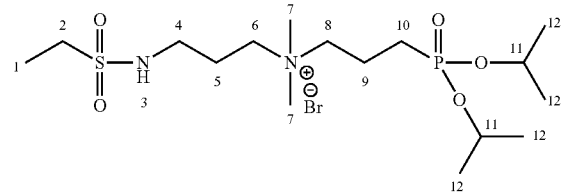 [SMILES: CCS(=O)(=O)NCCC[N+](C)(C)CCCP(=O)(OC(C)C)OC(C)C ; [Br-]]

Example 21—3-(diisopropoxyphosphoryl)-N-(3-(ethylsulfonamido)propyl)-N,N-dimethyl propan-1-aminium bromide (7b)

This compound was synthesized using N-(3-(dimethylamino)propyl)ethanesulfonamide (0.25 g, 1.29 mmol) and diisopropyl (3-bromopropyl)phosphonate (0.30 mL, 1.29 mmol, 1 eq.) in ACN (3 mL) for 5 hours resulting in viscous golden yellow brown solution. The product was purified using $Et_2O$ (10 mL×3) and obtained as white gummy powder after drying under $10^{-3}$ mm Hg vacuum at room temperature. Yield: 86.0% (0.53 g). $^1$H NMR (CDCl$_3$, 400 MHz, δ): 7.08 (t, 1H, $J_{3-4}$=5.8 Hz, H3), 4.76-4.54 (m, 2H, H11), 3.74 (t, 2H, $J_{6-5}$=7.6 Hz, H6), 3.63 (t, 2H, $J_{8-9}$=7.9 Hz, H8), 3.35-3.16 (m, 8H, H7 & H4), 3.07 (q, 2H, $J_{2-1}$=7.4 Hz, H2), 2.27-2.13 (m, 2H, H5), 2.12-1.96 (m, 2H, H9), 1.82 (dt, 2H, $J_{10-P}$=17.4 Hz, $J_{10-9}$=7.2 Hz, H10), 1.44-1.24 (m, 15H, H1 & H12) ppm. $^{13}$C {$^1$H} NMR (CDCl$_3$, 100 MHz, δ): 70.74 (d, $^2J_{11-P}$=6.7 Hz, C11), 63.75 (d, $^3J_{8-P}$=15.7 Hz, C8), 62.36 (C6), 51.20 (C7), 46.22 (C2), 39.97 (C4), 24.12 (d, $J_{12-P}$=4.5 Hz, C12), 23.98 (d, $J_{12-P}$=4.0 Hz, C12), 23.86 & 22.43 (d, $^2J_{10-P}$=144.3 Hz, C10), 23.36 (C8), 16.74 (C9), 8.24 (C1) ppm. $^{31}$P{H} NMR (CDCl$_3$, 121.45 MHz, δ): 27.05 ppm. HRMS-ESI-TOF (m/z): [M$^+$–Br$^-$] calculated for C$_{16}$H$_{38}$N$_2$O$_5$P$_1$S$_1$, 401.2234, found, 401.2235.

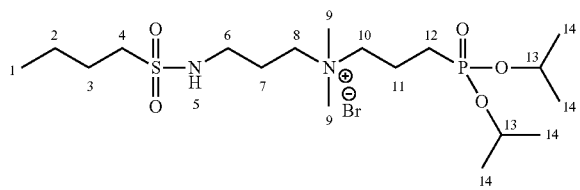 [SMILES: CCCCS(=O)(=O)NCCC[N+](C)(C)CCCP(=O)(OC(C)C)OC(C)C ; [Br-]]

Example 22—3-(butylsulfonamido)-N-(3-(diisopropoxyphosphoryl)propyl)-N,N-dimethyl propan-1-aminium bromide (8b)

This compound was synthesized using N-(3-(dimethylamino)propyl)butane-1-sulfonamide (0.50 g, 2.25 mmol) and diisopropyl (3-bromopropyl)phosphonate (0.60 mL, 2.25 mmol, 1 eq.) in ACN (3 mL) for 3 hours resulting in viscous golden yellow brown solution. The product was purified using Et$_2$O (10 mL×3) and obtained as pale yellow gummy powder after drying under $10^{-3}$ mm Hg vacuum at room temperature. Yield: 82.0% (0.94 g). $^1$H NMR (CDCl$_3$, 400 MHz, δ): 7.07 (t, 1H, $J_{3-4}$=6.1 Hz, H5), 4.69 (qd, 2H, $J_{13-P}$=12.4 Hz, $J_{13-14}$=6.2 Hz, H13), 3.78 (t, 2H, $J_{8-7}$=7.8 Hz, H8), 3.66 (t, 2H, $J_{10-11}$=8.4 Hz, H10), 3.33 (s, 6H, H9), 3.28 (dd, 2H, $J_{6-5}$=12.0 Hz, $J_{6-7}$=6.0 Hz, H6), 3.29 (t, 2H, $J_{4-3}$=8.4 Hz, H4), 2.24-2.15 (m, 2H, H7), 2.15-2.03 (m, 2H, H11), 1.89-1.75 (m, 4H, H3 & H12), 1.45 (dq, 2H, $J_{2-3}$=14.7, $J_{2-1}$=7.3, H2), 1.38-1.29 (m, 12H, H14), 0.96 (t, 3H, $J_{1-2}$=7.4 Hz, H1) ppm. $^{13}$C {$^1$H} NMR (CDCl$_3$, 100 MHz, δ): 70.77 (d, $^2J_{13-P}$=6.7 Hz, C13), 63.73 (d, $^3J_{10-P}$=15.5 Hz, C10), 62.36 (C8), 51.72 (C4), 51.25 (C9), 39.98 (C6), 25.35 (C3), 24.14 (d, $J_{14-P}$=4.5 Hz, C14), 24.00 (d, $J_{14-P}$=4.0 Hz, C14), 23.87 & 22.43 (d, $J_{12-P}$=144.4 Hz, C12), 23.37 (C7), 21.51 (C2), 16.73 (d, $^2J_{11-P}$=4.2 Hz, C11), 13.62 (C1) ppm. $^{31}$P{$^1$H}NMR (CDCl$_3$, 121.45 MHz, δ): 27.22 ppm. HRMS-ESI-TOF (m/z): [M$^+$–Br$^-$] calculated for C$_{18}$H$_{42}$N$_2$O$_5$P$_1$S$_1$, 429.2547, found, 429.2543.

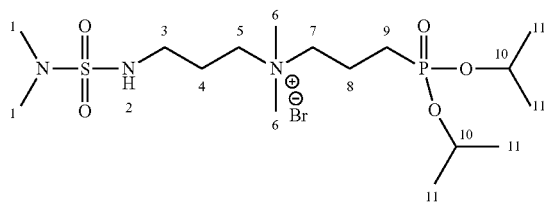 [SMILES: CC(C)OP(=O)(CCC[N+](C)(C)CCCNS(=O)(=O)N(C)C)OC(C)C ; [Br-]]

Example 23—3-(diisopropoxyphosphoryl)-N-(3-((N,N-dimethylsulfamoyl)amino)propyl)-N,N-dimethylpropan-1-aminium bromide (9b)

This compound was synthesized using N-(2-(dimethylamino)propyl)-N,N-Dimethyl-sulfamide (0.50 g, 2.39 mmol) and diisopropyl (3-bromopropyl)phosphonate (0.6 mL, 2.39 mmol, 1 eq.) in ACN (3 mL) for 3 hours resulting in viscous pale yellow solution. The product was purified using Et$_2$O (10 mL×3) and obtained as pale yellow fluffy/gummy powder after drying under $10^{-3}$ mm Hg vacuum at room temperature. Yield: 91.7% (1.09 g). $^1$H NMR (CDCl$_3$, 400 MHz, δ): 7.02 (t, 1H, $J_{2-3}$=5.9 Hz, H2), 4.62 (qd, 2H, $J_{10-P}$=12.4 Hz, $J_{10-11=6.2}$ Hz, H10), 3.66 (t, 2H, $J_{5-4}$=7.9 Hz, H5), 3.59 (t, 2H, $J_{7-8}$=8.2 Hz, H7), 3.26 (s, 6H, H6), 3.14 (dd, 2H, $J_{3-2}$=12.0 Hz, $J_{3-4}$=6.0 Hz, H3), 2.75 (s, 6H, H1), 2.20-2.06 (m, 2H, H4), 2.05-1.97 (m, 2H, H8), 1.78 (dt, 2H, $J_{9-P}$=17.4 Hz, $J_{9-8}$=7.2 Hz, H9), 1.31-1.20 (m, 12H, H11) ppm. $^{13}$C {$^1$H} NMR (CDCl$_3$, 100 MHz, δ): 70.78 (d, $^2J_{10-P}$=6.6 Hz, C10), 63.74 (d, $^3J_{7-P}$=15.4 Hz, C7), 62.44 (C5), 51.24 (C6), 40.19 (C6), 38.15 (C1), 24.13 (d, $J_{11-P}$=4.5 Hz, C11), 24.06 (d, $J_{11-P}$=4.0 Hz, C11), 23.87 & 22.44 (d, $J_{9-P}$=144.0 Hz, C9). 22.84 (C4), 16.74 (C8) ppm. $^{31}$P{H} NMR (CDCl$_3$, 121.45 MHz, δ): 27.27 ppm. HRMS-ESI-TOF (m/z): [M$^+$–Br$^-$] calculated for C$_{16}$H$_{39}$N$_3$O$_5$P$_1$S$_1$, 416.2343, found, 416.2341.

Synthesis of Benzophenone based QAC

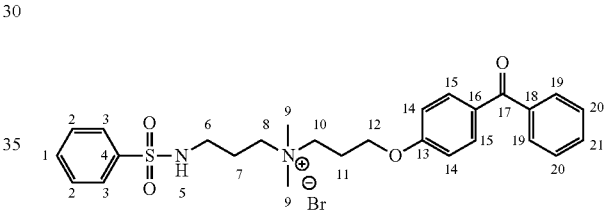

Example 24—3-(4-benzoylphenoxy)-N,N-dimethyl-N-(3-(phenylsulfonamido)propyl) propan-1-aminium bromide (1c)

This compound was synthesized using N-(3-(dimethylamino)propyl)phenylsulfonamide (0.921 g, 3.8 mmol) and 4-(3-bromopropoxy)benzophenone (1.29 g, 4.0 mmol) in ACN (10 mL) for 48 hours; yielding in viscous pale yellow solution. The product was obtained as fluffy pale yellow powder after washing with Et$_2$O (10 mL×3) and drying under $10^{-3}$ mm Hg vacuum at room temperature. Yield: 82% (1.74 g). $^1$H NMR (CDCl$_3$, 400 MHz, δ): 7.96-7.89 (m, 2H, H3), 7.86-7.77 (m, 1H, H5), 7.74-7.62 (m, 4H, H15 & H19), 7.57-7.49 (m, 1H, H21), 7.49-7.37 (m, 5H, (H1, H2, & H20)), 6.89 (d, 2H, $J_{14-15}$=8.9 Hz, H14), 4.11 (t, $J_{12-11}$=5.3 Hz, H12), 3.79-3.56 (m, 4H, H8 & H10), 3.27 (s, 6H, H9), 3.06-2.92 (m, 2H, H6), 2.36-2.19 (m, 2H, H11), 2.19-1.97 (m, 2H, H7) ppm. $^{13}$C {$^1$H} NMR (CDCl$_3$, 100 MHz, δ): 195.58 (C17), 161.80 (C13), 139.64 (C1), 137.99 (C4), 132.71 (C18), 132.51 (C15), 132.19 (C21), 130.60 (C16), 139.75 (C2), 129.32 (C19), 128.35 (C20), 127.22 (C3), 114.31 (C14), 64.68 (C12), 62.44 (C8), 62.06 (C10), 39.98 (C6), 23.08 (C11), 22.75 (C7) ppm. HRMS-ESI-TOF (m/z): [M$^+$–Br$^-$] calculated for C$_{27}$H$_{33}$N$_2$O$_4$S, 481.2156; found 481.2155.

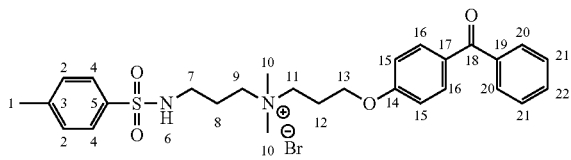 [SMILES: Cc1ccc(S(=O)(=O)NCCC[N+](C)(C)CCCOc2ccc(C(=O)c3ccccc3)cc2)cc1 ; [Br-]]

MHz, δ): 195.63 (C19), 161.81 (C15), 142.40 (C5), 139.24 (C2), 138.15 (20), 133.41 (C6), 132.66 (C17), 132.22 (C23), 132.18 (C3), 130.91 (C18), 129.90 (C21), 128.39 (C22), 64.72 (C14), 62.68 (C10), 62.29 (C12), 51.77 (C11), 39.36 (C8), 23.42 (C4), 23.27 (C13), 23.05 (C9), 21.03 (C1) ppm. HRMS-ESI-TOF (m/z): [M$^+$–Br$^-$] calculated for C$_{30}$H$_{39}$N$_2$O$_4$S, 523.2625; found 523.2636.

Example 25—3-(4-benzoylphenoxy)-N,N-dimethyl-N-(3-(4-methylphenylsulfonamido) propyl)propan-1-aminium bromide (2c)

This compound was synthesized using N-(3-(dimethylamino)propyl)-4-methylphenyl)sulfonamide (1.05 g, 4.1 mmol) and 4-(3-bromopropoxy)benzophenone (1.417 g, 4.44 mmol) in ACN (10 mL) for 48 hours; yielding in viscous pale yellow solution. The product was obtained as fluffy pale yellow powder after washing with Et$_2$O (10 mL×3) and drying under 10$^{-3}$ mm Hg vacuum at room temperature. Yield: 80% (1.88 g). $^1$H NMR (CDCl$_3$, 400 MHz, δ): 7.80 (d, 2H, J$_{4-2}$=8.2 Hz, H4), 7.73-7.65 (m, 4H, H16 & H20), 7.56-7.59 (m, 1H, H22), 7.42 (t, J$_{4-2}$=7.2 Hz 2H, H22), 7.21 (d, 2H, J$_{2-4}$=8.2 Hz, H2), 6.89 (d, 2H, J$_{15-16}$=8.8 Hz, H15), 4.12 (t, 2H, J$_{13-12}$=5.4 Hz, H13), 3.79-3.59 (m, 4H, H9 & H11), 3.29 (s, 6H, H10), 3.07-2.90 (m, 2H, H7), 2.35-2.23 (m, 5H, H1 & H12), 2.19-2.03 (m, 2H, H8) ppm. $^{13}$C {$^1$H} NMR (CDCl$_3$, 100 MHz, δ): 195.57 (C18), 161.82 (C14), 143.50 (C3), 138.05 (C5), 136.53 (C19), 132.54 (C16), 132.19 (C22), 130.69 (C17), 129.90 (C20), 129.80 (C2), 128.36 (C21), 127.34 (C4), 114.32 (C15), 64.71 (C13), 62.53 (C9), 62.11 (C11), 51.62 (C10), 40.01 (C7), 23.15 (C12), 22.75 (C8), 21.57 (C1) ppm. HRMS-ESI-TOF (m/z): [M$^+$–Br$^-$] calculated for C$_{28}$H$_{35}$N$_2$O$_4$S, 495.2312; found 495.2319.

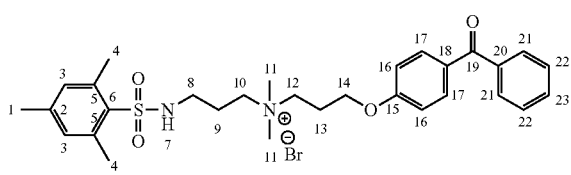 [SMILES: Cc1cc(C)c(S(=O)(=O)NCCC[N+](C)(C)CCCOc2ccc(C(=O)c3ccccc3)cc2)c(C)c1 ; [Br-]]

Example 26—3-(4-benzoylphenoxy)-N,N-dimethyl-N-(3-(2,4,6-trimethylphenylsulfonamido) propyl)propan-1-aminium bromide (3c)

This compound was synthesized using N-(3-(dimethylamino)propyl)-2,4,6-trimethylphenyl)sulfonamide (0.853 g, 3.0 mmol) and 4-(3-bromopropoxy)benzophenone (1.0 g, 3.13 mmol) in ACN (10 mL) for 48 hours; yielding in viscous pale yellow solution. The product was obtained as fluffy white powder after washing with Et$_2$O (10 mL×3) and drying under 10-mm Hg vacuum at room temperature. Yield: 67% (1.20 g). $^1$H NMR (CDCl$_3$, 400 MHz, δ): 7.76 (d, 2H, J$_{17-16}$=8.7 Hz, H17), 7.72 (d, 2H, J$_{21-22}$=7.2 Hz, H21), 7.56 (t, 2H, J$_{23-22}$=7.4 Hz, H23), 7.49-7.41 (m, 2H, H22), 7.22 (t, 1H, J$_{4-2}$=6.2 Hz, H7), 6.94 (t, 2H, J$_{16-17}$=6.0 Hz, H16), 6.90 (s, 2H, H3), 4.21 (t, 2H, J$_{14-13}$=5.4 Hz, H14), 3.90-3.80 (m, 2H, H10), 3.80-3.68 (m, 2H, H12), 3.37 (s, 6H, H11), 3.04 (dd, 2H, J$_{8-7}$=11.4 Hz, J$_{8-9}$=5.7 Hz, H8), 2.63 (s, 6H, H4), 2.43-2.32 (m, 2H, H13), 2.25 (s, 3H, H1), 2.23-2.13 (m, 2H, H9) ppm. $^{13}$C {$^1$H} NMR (CDCl$_3$, 100 MHz, δ): 195.63 (C19), 161.81 (C15), 142.40 (C5), 139.24 (C2), 138.15 (20), 133.41 (C6), 132.66 (C17), 132.22 (C23), 132.18 (C3), 130.91 (C18), 129.90 (C21), 128.39 (C22), 64.72 (C14), 62.68 (C10), 62.29 (C12), 51.77 (C11), 39.36 (C8), 23.42 (C4), 23.27 (C13), 23.05 (C9), 21.03 (C1) ppm. HRMS-ESI-TOF (m/z): [M$^+$–Br$^-$] calculated for C$_{30}$H$_{39}$N$_2$O$_4$S, 523.2625; found 523.2636.

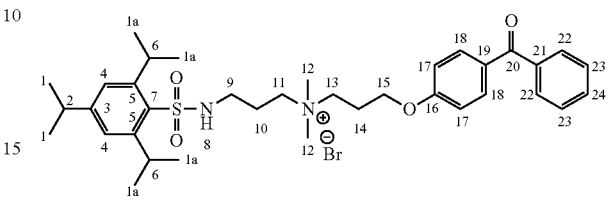

Example 27—3-(4-benzoylphenoxy)-N,N-dimethyl-N-(3-(2,4,6-triisopropylphenylsulfon amido)propyl) propan-1-aminium bromide (4c)

This compound was synthesized using N-(3-(dimethylamino)propyl)-2,4,6-triisopropylbenzenesulfonamide (0.379 g, 1.03 mmol) and 4-(3-bromopropoxy)benzophenone (0.329 g, 1.03 mmol) in ACN (10 mL) for 48 hours; yielding in viscous pale yellow solution. The product was obtained as fluffy pale white powder after washing with Et$_2$O (10 mL×3) and drying under 10$^{-3}$ mm Hg vacuum at room temperature. Yield: 92% (0.65 g). $^1$H NMR (CDCl$_3$, 400 MHz, δ): 7.78-765 (m, 4H, H18 & H22), 7.57-7.49 (m, 1H, H24), 7.43 (t, 2H, J$_{23-22}$=7.5 Hz, H23), 7.12 (s, 2H, H4), 7.06 (t, 1H, J$_{8-9}$=6.1 Hz, H8), 6.93 (d, 2H, J$_{17-18}$=8.9 Hz, H17), 4.20 (t, 2H, J$_{15-14}$=5.5 Hz, H15), 4.16-4.05 (m, 2H, H6), 3.90-3.81 (m, 2H, H11), 3.80-3.69 (m, 2H, H13), 3.39 (s, 6H, H12), 3.10 (dd, 1H, J$_{9-8}$=11.3 Hz, J$_{9-10}$=5.7 Hz, H9), 2.91-2.79 (m, 2H, H2), 2.45-2.31 (m, 2H, H14), 2.28-2.14 (m, 2H, H10), 1.21 (dd, 18H, J$_{1-2}$=6.8 Hz, J$_{1a-6}$=2.3 Hz, H1 & H1a) ppm. $^{13}$C {$^1$H} NMR (CDCl$_3$, 100 MHz, δ): 195.55 (C20), 161.75 (C16), 152.76 (C3), 150.33 (C7), 138.01 (C21), 132.50 (C18), 132.06 (C24), 131.96 (C5), 130.66 (C19), 129.74 (C22), 128.24 (C23), 123.88 (C4), 114.22 (C17), 64.67 (C15), 62.49 (C11), 62.03 (C13), 51.66 (C12), 39.47 (C9), 34.10 (C2), 29.54 (C6), 25.12 (C1), 23.14 (C14), 23.07 (C10) ppm. HRMS-ESI-TOF (m/z): [M$^+$–Br$^-$] calculated for C$_{36}$H$_{51}$N$_2$O$_4$S, 607.3564; found 607.3555.

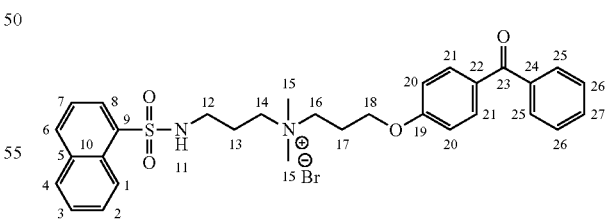

Example 28—3-(4-benzoylphenoxy)-N,N-dimethyl-N-(3-(naphthalene-1-sulfonamido) propyl)propan-1-aminium bromide (5c)

This compound was synthesized using N-(3-(dimethylamino)propyl)naphthalene-1-sulfonamide (0.584 g, 2.0 mmol) and 4-(3-bromopropoxy)benzophenone (0.702 g, 2.2 mmol) in ACN (10 mL) for 48 hours; yielding in viscous pale yellow solution. The product was obtained as fluffy white powder after washing with Et$_2$O (10 mL×3) and drying under 10$^{-3}$ mm Hg vacuum at room temperature. Yield: 82% (1.0 g). $^1$H NMR (CDCl$_3$, 400 MHz, δ): 8.80 (d, 1H, $J_{1-2}$=8.7 Hz, H1), 8.15 (d, 1H, $J_{8-7}$=7.3 Hz, H8), 7.96 (s, 1H, H11), 7.91 (d, 1H, $J_{8-7}$=8.3 Hz, H6), 7.78 (d, 1H, $J_{4-3}$=8.2 Hz, H4), 7.70-7.55 (m, 4H, (H2, H25, & H21)), 7.51 (t, 2H, $J_{27-26}$=7.4 Hz, H27), 7.46-7.34 (m, 4H, (H3, H26, & H7), 6.77 (d, 2H, $J_{20-21}$=8.7 Hz, H20), 4.00-3.85 (m, 2H, H18), 3.59-3.37 (m, 4H, H14 & H16), 3.19-2.91 (m, 8H, H15 & H12), 2.17-1.99 (m, 2H, H17), 1.97-1.76 (m, 2H, H13) ppm. $^{13}$C {$^1$H} NMR (CDCl$_3$, 100 MHz, δ): 195.59 (C23), 161.77 (C19), 138.04 (C24), 134.85 (C9), 134.21 (C6), 132.50 (C25), 132.20 (C27), 130.56 (C10), 129.80 (C2), 129.36 (C8), 129.05 (C4), 128.76 (C21), 128.37 (C7), 128.00 (C22), 127.18 (C3), 125.20 (C1), 124.52 (C26), 114.25 (C20), 64.59 (C18), 62.42 (C14), 62.10 (C16), 51.42 (15), 39.83 (C12), 22.92 (C17 & C13) ppm. HRMS-ESI-TOF (m/z): [M$^+$−Br$^-$] calculated for C$_{31}$H$_{35}$N$_2$O$_4$S, 531.2312; found 531.2328.

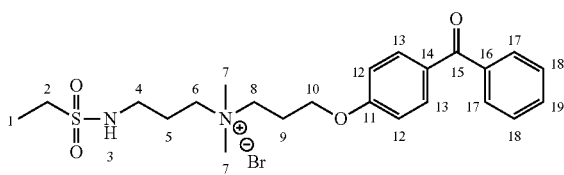 [SMILES: CCS(=O)(=O)NCCC[N+](C)(C)CCCOc1ccc(C(=O)c2ccccc2)cc1 ; [Br-]]

Example 29—3-(4-benzoylphenoxy)-N-(3-(ethylsulfonamido)propyl)-N,N-dimethylpropan-1-aminium bromide (7c)

This compound was synthesized using N-(3-(dimethylamino)propyl)ethanesulfonamide (0.250 g, 1.29 mmol) and 4-(3-bromopropoxy)benzophenone (0.411 g, 1.29 mmol) in ACN (10 mL) for 48 hours; yielding in viscous pale yellow solution. The product was obtained as fluffy pale yellow powder after washing with Et$_2$O (10 mL×3) and drying under 10$^{-3}$ mm Hg vacuum at room temperature. Yield: 77% (0.52 g). $^1$H NMR (CDCl$_3$, 400 MHz, δ): 7.78 (d, 2H, $J_{13-12}$=8.7 Hz, H13), 7.72 (d, 2H, $J_{17-18}$=7.4 Hz, H17), 7.56 (t, 2H, $J_{19-18}$=7.4 Hz, H19), 7.50-7.40 (m, 2H, H18), 7.12 (t, 1H, $J_{3,4}$=6.0 Hz, H3), 6.98 (d, 2H, $J_{12-13}$=8.8 Hz, H12), 4.21 (t, 2H, $J_{10-9}$=5.3 Hz, H10), 3.86-3.75 (m, 2H, H6), 3.75-3.65 (m, 2H, H8), 3.35 (s, 6H, H7), 3.31-3.22 (m, 2H, H4), 3.07 (q, 2H, $J_{2-3}$=7.3 Hz, H2), 2.43-2.29 (m, 2H, H9), 2.27-2.13 (m, 2H, H5), 1.34 (t, 3H, $J_{2-3}$=7.4 Hz, H1) ppm. $^{13}$C {$^1$H} NMR(CDCl$_3$, 100 MHz, δ): 195.55 (C15), 161.66 (C11), 137.94 (C16), 132.55 (C13), 132.16 (C19), 130.83 (C14), 129.78 (C17), 128.29 (C18), 114.22 (C12), 64.57 (C10), 62.46 (C6), 62.17 (C5), 51.61 (C7), 46.44 (C2), 39.95 (C4), 23.64 (C5), 23.11 (C9), 8.27 (C1) ppm. HRMS-ESI-TOF (m/z): [M$^+$−Br$^-$] calculated for C$_{23}$H$_{33}$N$_2$O$_4$S, 433.2156; found 433.2153.

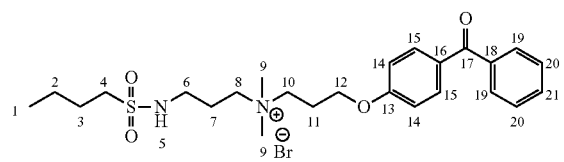 [SMILES: CCCCS(=O)(=O)NCCC[N+](C)(C)CCCOc1ccc(C(=O)c2ccccc2)cc1 ; [Br-]]

Example 30—3-(4-benzoylphenoxy)-N-(3-(butylsulfonamido)propyl)-N,N-dimethylpropan-1-aminium bromide (8c)

This compound was synthesized using N-(3-(dimethylamino)propyl)butane-1-sulfonamide (0.324 g, 1.46 mmol) and 4-(3-bromopropoxy)benzophenone (0.466 g, 1.46 mmol) in ACN (10 mL) for 48 hours; yielding in viscous pale yellow solution. The product was obtained as fluffy pale yellow powder after washing with Et$_2$O (10 mL×3) and drying under 10$^{-3}$ mm Hg vacuum at room temperature. Yield: 73% (0.58 g). $^1$H NMR (CDCl$_3$, 400 MHz, δ): 7.74 (d, 2H, $J_{15-14}$=8.7 Hz, H15), 7.69 (d, 2H, $J_{19-20}$=7.1 Hz, H19), 7.54 (t, 1H, $J_{21-20}$=7.4 Hz, H21), 7.47-7.38 (m, 2H, H20), 7.10 (t, 1H, $J_{5-6}$=5.6 Hz, H5), 6.96 (d, 2H, $J_{14-15}$=8.8 Hz, H14), 4.18 (t, 1H, $J_{12-11}$=5.2 Hz, H12), 3.79-3.61 (m, 2H, H8 & H10), 3.33 (s, 6H, H9), 3.27-3.20 (m, 2H, H6), 3.10-2.96 (m, 2H, H4), 2.42-2.25 (m, 2H, H11), 2.25-2.07 (m, 2H, H7), 1.80-1.65 (m, 2H, H3), 1.38 (dq, 2H, $J_{2-3}$=14.6 Hz, $J_{2-1}$=7.4 Hz, H2), 0.87 (t, 3H, $J_{1-2}$=7.3 Hz, H1) ppm. $^{13}$C {$^1$H} NMR (CDCl$_3$, 100 MHz, δ): 195.56 (C17), 161.17 (C13), 137.89 (C18), 132.50 (C15), 132.16 (C21), 130.62 (C16), 129.71 (C19), 128.29 (C20), 114.27 (C14), 64.67 (C12), 62.30 (C8), 61.96 (C10), 51.79 (C4), 51.56 (C9), 25.37 (C3), 23.55 (C7), 23.05 (C11), 21.51 (C2), 13.64 (C1) ppm. HRMS-ESI-TOF (m/z): [M$^+$−Br$^-$] calculated for C$_{25}$H$_{37}$N$_2$O$_4$S, 461.2469; found 461.2458.

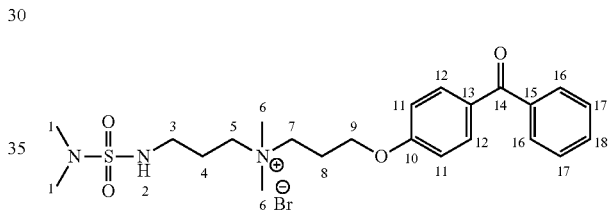

Example 31—3-(4-benzoylphenoxy)-N-(3-((N,N-dimethylsulfamoyl)amino)propyl)-N,N-dimethylpropan-1-aminium bromide (9c)

This compound was synthesized using N-(2-(dimethylamino)propyl)-N,N-Dimethyl-sulfamide (0.232 g, 1.11 mmol) and 4-(3-bromopropoxy)benzophenone (0.354 g, 1.11 mmol) in ACN (10 mL) for 48 hours; yielding in viscous pale yellow solution. The product was obtained as fluffy pale yellow powder after washing with Et$_2$O (10 mL×3) and drying under 10$^{-3}$ mm Hg vacuum at room temperature. Yield: 60% (0.36 g). $^1$H NMR (CDCl$_3$, 400 MHz, δ): 7.70 (d, 2H, $J_{12-11}$=8.7 Hz, H12), 7.65 (d, 2H, $J_{16-17}$=7.2 Hz, H16), 7.51 (t, 1H, $J_{18-17}$=7.4 Hz, H18), 7.44-7.36 (m, 2H, H17), 7.03-6.87 (m, 3H, H11 & H2), 4.15 (t, 2H, $J_{9-8}$=4.7 Hz, H9), 3.71-3.53 (m, 4H, H5 & H7), 3.28 (s, 6H, H6), 3.20-3.12 (m, 2H, H3), 2.72 (s, 6H, H1), 2.37-2.22 (m, 2H, H8), 2.19-2.02 (m, 2H, H4) ppm. $^{13}$C {$^1$H} NMR (CDCl$_3$, 100 MHz, δ): 195.62 (C14), 161.88 (C9), 137.87 (C15), 132.50 (C12), 132.17 (C18), 130.49 (C13), 129.73 (C16), 128.30 (C17), 114.35 (C11), 64.82 (C9), 62.24 (C5), 61.76 (C7), 51.62 (C6), 40.18 (C3), 38.15 (C1), 23.06 (C4), 22.97 (C8) ppm. HRMS-ESI-TOF (m/z): [M$^+$−Br$^-$] calculated for C$_{23}$H$_{34}$N$_3$O$_4$S, 448.2265; found 448.2262.

Example 31A—N-(3-(4-benzoylphenoxy)propyl)-3-((7,7-dimethyl-2-oxobicyclo[2.2.1]heptan-1-yl)methylsulfonamido)-N,N-dimethylpropan-1-ide-1-aminium, bromide salt

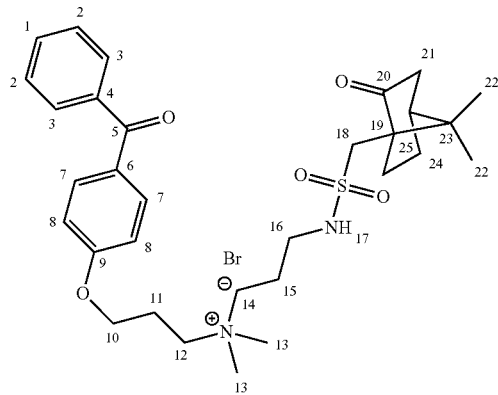

This compound was synthesized using 1-(7,7-dimethyl-2-oxobicyclo[2.2.1]heptan-1-yl)-N-(3-(dimethylamino)propyl)methanesulfonamide (1.32 g, 4.187 mmol) and 4-(3-bromopropoxy)benzophenone (1.403 g, 4.39 mmol, 1.05 eq.) in refluxing EtOAc (10 mL) for 3 hours; yielding a viscous pale yellow oil. The product was obtained as fluffy white powder after purification. Yield: 58% (1.535 g), Mp=33-34° C. $^1$H NMR (CDCl$_3$, 400 MHz, δ): δ 7.80-7.73 (m, 2H, H3), 7.73-7.58 (m, 2H, H7), 7.48 (s, 1H, H1), 7.43-7.37 (m, 2H, H2), 7.09-6.95 (m, 2H, H8), 4.04-4.00 (m, 2H, H10), 3.69 (s, 1H, H18), 3.54-3.39 (m, 5H, H18, H12, H14), 3.36-3.32 (m, 6H, H13), 2.76 (d, J=7.4 Hz, 2H, H16), 2.36 (s, 1H), 2.22-2.18 (m, 2H, H11), 2.11 (s, 1H), 2.03 (dd, J=19.1, 0.6 Hz, 4H), 1.83 (s, 1H, H25), 1.59 (s, 1H, H24), 1.34 (s, 1H, H24), 1.11 (s, 3H, H22), 1.08 (m, 3H, H22) ppm.

Figure 1:
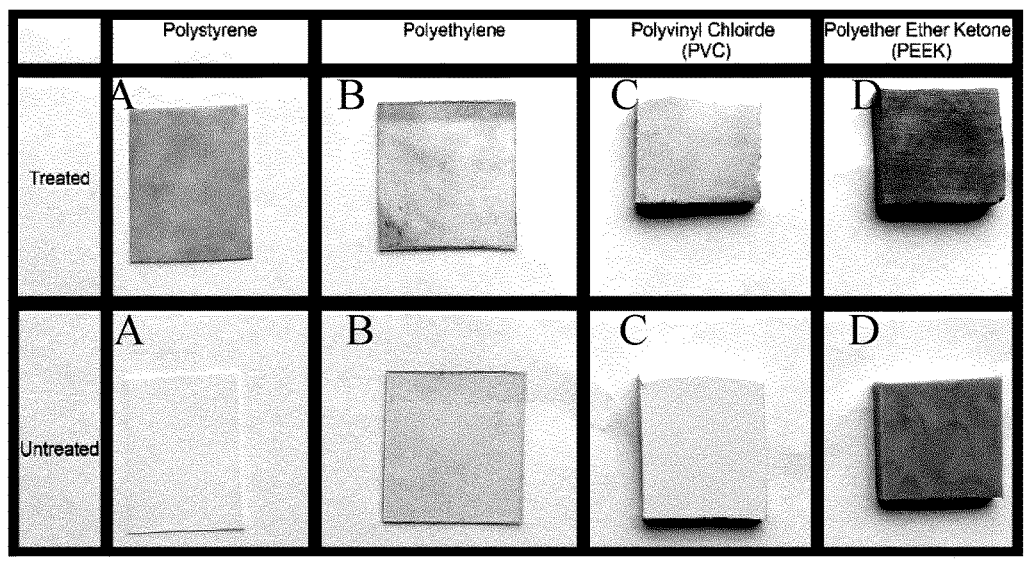
FIG. 1 shows an image of polymer samples before (light coloured) and after (dark coloured) treatment with benzophenone-anchored sulfonamide quat antimicrobial compound.

Example 32—Application and Curing of Benzophenone-Anchored Antimicrobials to Test Surfaces 1% (w/v) solutions of the benzophenone-anchored sulfonamide quaternary ammonium cation (QUAT) antimicrobials were prepared by dissolving the desired antimicrobial compound within a range of ethanol:water mixture between 10:90 to 40:60, depending on the solubility of the antimicrobial compound. An emphasis was made to reduce ethanol content where applicable. Coating of the test samples, which consisted of 25 mm (±5 mm)×25 mm (±5 mm)×1 mm coupons of each plastic material, was performed via an ESS AD-LG electrospray apparatus set to 150 kPa that applied the compound uniformly over the test surfaces. After application, the coated surfaces were allowed to air-dry before proceeding to a UV curing step which involved exposing the surfaces to 5000 mW intensity UV light for 1 minute. This coating and curing sequence was repeated a second time to ensure adequate coverage of the compound, as confirmed with bromophenol blue staining which allowed for visualization of the surface-bound sulfonamide QUAT compound. Stock polystyrene and polyethylene material was supplied by VWR International, polyvinyl chloride was sourced from Home Depot and polyether ether ketone was sourced from Drake Plastics. FIG. 1 shows the treated versus untreated samples.

Example 33—Application and Curing of Silicone-Anchored Antimicrobials to Test Surfaces 1% (w/v) solutions of the silane-anchored sulfonamide QUAT antimicrobials were prepared in a range of methanol:water mixtures between 30:70 to 70:30, depending on the solubility of the antimicrobial compound. An emphasis was made to reduce methanol content where applicable. Coating of the test samples was performed via gently heating and agitating cotton samples at 40° C. within the coating solution for 5 minutes. After application, the coated surfaces were allowed to air-dry before rinsing with water. Coating quality of the treated cotton samples was confirmed with bromophenol blue staining, which allowed for visualization of the surface-bound sulfonamide QUAT compound. Stock cotton fabric was supplied by META Labware. FIG. 2 shows the treated versus untreated cotton samples.

Example 34—Testing Antimicrobial Efficacy at Solid-Air Interfaces

Large-droplet inoculation method (Ronan E. et al, *Biofouling* 2013, 29, 1087-1096) Many pathogens are able to remain viable during extended periods of desiccation on inanimate surfaces. Long-term survival of pathogens in the inanimate environment pose a significant risk for infection transmission and contamination in high-risk environments such as hospital rooms or food-processing plants. The large-droplet inoculation method was developed to simulate the deposition of bacterial species onto exposed surfaces and to determine the ability of these cells to survive desiccation.

For these tests, small surface coupons were first coated with the antimicrobial using the method described above. Bacterial test species were grown overnight in a shaking incubator and cultures were washed twice to replace the growth media with sterile water. 100 μL aliquots of the prepared culture were then inoculated onto multiple coated surfaces and allowed to air-dry within a biological safety cabinet. Drying typically occurred 2-3 hours after inoculation, and surviving cells were enumerated immediately and 24 hours after drying. For enumeration, inoculated coupons were sacrificed in triplicate and placed inside separate tubes containing 5 mL of a 0.9% saline collection liquid. Each coupon was agitated vigorously for 1 minute with a bench-top vortex to transfer cells from the test surface to the collection liquid. Plate counts were then performed on serial dilutions of the collection liquid, and colony counts from triplicate treated surfaces were averaged and compared to colony counts from tests of untreated control surfaces carried out in parallel.

A range of bacterial species were used in these tests. *Arthrobacter* spp., a gram-positive lab strain originally isolated from indoor air was used in the bulk of the testing, as it is known to be highly resistant to desiccation and therefore was used as a model for desiccation-tolerant pathogens. Efficacy tests were also carried out against, for example, gram-negative *Escherichia coli* (*E. coli*) and gram-positive *Staphylococcus aureus* (*S. aureus*), since they all contain pathogenic strains and have been implicated in major nosocomial outbreaks. FIG. 3 shows that 3-(4-benzoylphenoxy)-N,N-dimethyl-N-(3-(2,4,6-trimethylphenylsulfonamido)propyl) propan-1-aminium bromide treated polystyrene and N,N-dimethyl-3-(4-methylphenyl sulfonamido)-N-(3-

(trimethoxysilyl)propyl)propan-1-aminium chloride treated cotton demonstrated within three hours excellent activity against *Arthrobacter* spp. The following are the tabulated bacterial reduction data:

|  | A (cfu) | B (cfu) | C (cfu) | Average | Deviation |
|---|---|---|---|---|---|
| Polystyrene Control |  |  |  |  |  |
| 0 hours (Load) | 1.28E+08 | 1.28E+08 | 1.28E+08 | 1.28E+08 | 0.00E+00 |
| 3 hours | 9.75E+06 | 7.65E+06 | 8.60E+06 | 8.67E+06 | 1.05E+06 |
| 24 hours | 7.75E+03 | 9.10E+03 | 2.50E+02 | 5.70E+03 | 4.77E+03 |
| Polystyrene Mesityl |  |  |  |  |  |
| 0 hours (Load) | 1.28E+08 | 1.28E+08 | 1.28E+08 | 1.28E+08 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |
| Cotton Control |  |  |  |  |  |
| 0 hours (Load) | 1.28E+08 | 1.28E+08 | 1.28E+08 | 1.28E+08 | 0.00E+00 |
| 3 hours | 2.20E+06 | 1.65E+06 | 2.75E+06 | 2.20E+06 | 5.50E+05 |
| 24 hours | 5.60E+05 | 2.65E+05 | 3.10E+05 | 3.78E+05 | 1.59E+05 |
| Cotton Tosyl |  |  |  |  |  |
| 0 hours (Load) | 1.28E+08 | 1.28E+08 | 1.28E+08 | 1.28E+08 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |

FIG. 4 shows that N,N-dimethyl-3-(phenylsulfonamido)-N-(3-(trimethoxysilyl)propyl)propan-1-aminium chloride, N,N-dimethyl-3-(4-methylphenylsulfonamido)-N-(3-(trimethoxysilyl) propyl)propan-1-aminium chloride, N,N-dimethyl-3-(trimethoxysilyl)-N-(3-(2,4,6-trimethyl phenylsulfonamido)propyl)propan-1-aminium chloride and N,N-dimethyl-3-(naphthalene-1-sulfonamido)-N-(3-(trimethoxysilyl)propyl)propan-1-aminium chloride treated cotton demonstrated within three hours excellent activity against *Arthrobacter* spp. The following are tabulated bacteria reduction data:

|  | A (cfu) | B (cfu) | C (cfu) | Average | Deviation |
|---|---|---|---|---|---|
| Cotton Control |  |  |  |  |  |
| 0 hours (Load) | 4.04E+07 | 4.04E+07 | 4.04E+07 | 4.04E+07 | 0.00E+00 |
| 3 hours | 1.76E+03 | 1.92E+04 | 7.60E+03 | 9.50E+03 | 8.85E+03 |
| 24 hours | 1.20E+02 | 0.00E+00 | 0.00E+00 | 4.00E+01 | 6.92E+01 |
| Cotton Mesityl |  |  |  |  |  |
| 0 hours (Load) | 4.04E+07 | 4.04E+07 | 4.04E+07 | 4.04E+07 | 0.00E-1-00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |
| Cotton Tosyl |  |  |  |  |  |
| 0 hours (Load) | 4.04E+07 | 4.04E+07 | 4.04E+07 | 4.04E+07 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |
| Cotton Control |  |  |  |  |  |
| 0 hours (Load) | 6.10E+07 | 6.10E+07 | 6.10E+07 | 6.10E+07 | 0.00E+00 |
| 3 hours | 8.75E+04 | 2.70E+05 | 3.15E+05 | 2.24E+05 | 1.20E+05 |
| 24 hours | 6.95E+04 | 5.85E+04 | 7.15E+04 | 6.65E+04 | 7.00E+03 |
| Cotton Benzyl |  |  |  |  |  |
| 0 hours (Load) | 6.10E+07 | 6.10E+07 | 6.10E+07 | 6.10E+07 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |
| Cotton Naphthyl |  |  |  |  |  |
| 0 hours (Load) | 6.10E+07 | 6.10E+07 | 6.10E+07 | 6.10E+07 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |

FIG. 5 shows that 3-(4-benzoylphenoxy)-N,N-dimethyl-N-(3-(naphthalene-1-sulfonamido) propyl)propan-1-aminium bromide and 3-(4-benzoylphenoxy)-N,N-dimethyl-N-(3-(phenyl sulfonamido)propyl)propan-1-aminium bromide treated polyethylene demonstrated within three hours excellent activity against *Arthrobacter* spp. The following are tabulated bacteria reduction data:

|  | A (cfu) | B (cfu) | C (cfu) | Average | Deviation |
|---|---|---|---|---|---|
| Polyethylene Control |  |  |  |  |  |
| 0 hours (Load) | 2.70E+07 | 2.70E+07 | 2.70E+07 | 2.70E+07 | 0.00E+00 |
| 3 hours | 1.80E+04 | 7.00E+06 | 9.00E+05 | 2.64E+06 | 3.80E+06 |
| 24 hours | 4.00E+02 | 7.00E+02 | 5.00E+02 | 5.33E+02 | 1.53E+02 |
| Polyethylene Naphthyl |  |  |  |  |  |
| 0 hours (Load) | 2.70E+07 | 2.70E+07 | 2.70E+07 | 2.70E+07 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |
| Polyethylene Control |  |  |  |  |  |
| 0 hours (Load) | 2.70E+07 | 2.70E+07 | 2.70E+07 | 2.70E+07 | 0.00E+00 |
| 3 hours | 1.80E+04 | 7.00E+06 | 9.00E+05 | 2.64E+06 | 3.80E+06 |
| 24 hours | 4.00E+02 | 7.00E+02 | 5.00E+02 | 5.33E+02 | 1.53E+02 |
| Polyethylene Phenyl |  |  |  |  |  |
| 0 hours (Load) | 2.70E+07 | 2.70E+07 | 2.70E+07 | 2.70E+07 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |

FIG. 6 shows that 3-(4-benzoylphenoxy)-N,N-dimethyl-N-(3-(2,4,6-trimethylphenyl sulfonamido)propyl)propan-1-aminium bromide treated polyethylene demonstrated within three hours excellent activity against *E. coli* and *S. aureus*. The following are tabulated bacteria reduction data:

|  | A (cfu) | B (cfu) | C (cfu) | Average | Deviation |
|---|---|---|---|---|---|
| *E. coli* Control |  |  |  |  |  |
| 0 hours (Load) | 5.05E+07 | 5.05E+07 | 5.05E+07 | 5.05E+07 | 0.00E+00 |
| 3 hours | 5.00E+02 | 2.50E+02 | 4.50E+02 | 4.00E+02 | 1.32E+02 |
| 24 hours | 0.00E+00 | 0.00E+00 | 0.00E+00 | 0.00E+00 | 0.00E+00 |
| *E. coil* Mesityl |  |  |  |  |  |
| 0 hours | 5.05E+07 | 5.05E+07 | 5.05E+07 | 5.05E+07 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |
| *S. aureus* |  |  |  |  |  |

-continued

|  | A (cfu) | B (cfu) | C (cfu) | Average | Deviation |
|---|---|---|---|---|---|
| Control |  |  |  |  |  |
| 0 hours (Load) | 8.30E+05 | 8.30E+05 | 8.30E+05 | 8.30E+05 | 0.00E+00 |
| 3 hours | 1.10E+04 | 7.50E+03 | 8.00E+03 | 8.83E+03 | 1.89E+03 |
| 24 hours | 1.14E+04 | 3.20E+03 | 1.95E+03 | 5.52E+03 | 5.13E+03 |
| *S. aureus* Mesityl |  |  |  |  |  |
| 0 hours (Load) | 8.30E+05 | 8.30E+05 | 8.30E+05 | 8.30E+05 | 0.00E+00 |
| 3 hours | 0.00E+00 | 0.00E+00 | 0.00E+00 | 0.00E+00 | 0.00E+00 |
| 24 hours | 0.00E+00 | 0.00E+00 | 0.00E+00 | 0.00E+00 | 0.00E+00 |

FIG. 7 shows the inclusion of a trace amount (0.05% w/v) of a fluorophore demonstrated that a polyethylene sample was coated with 3-(4-benzoylphenoxy)-N,N-dimethyl-N-(3-(2,4,6-trimethylphenylsulfonamido)propyl)propan-1-aminium bromide. FIG. 8 shows that 3-(4-benzoylphenoxy)-N,N-dimethyl-N-(3-(2,4,6-trimethylphenylsulfonamido)propyl)propan-1-aminium bromide containing 0.05% w/v fluorophore demonstrated within three hours excellent activity against *Arthrobacter* spp. The following are tabulated bacteria reduction data:

|  | A (cfu) | B (cfu) | C (cfu) | Average | Deviation |
|---|---|---|---|---|---|
| Polyethylene Control |  |  |  |  |  |
| 0 hours (Load) | 4.63E+08 | 4.63E+08 | 4.63E+08 | 4.63E+08 | 0 |
| 3 hours | 4.20E+06 | 8.55E+06 | 9.10E+06 | 7.28E+06 | 2.68E+06 |
| Polyethylene Treated |  |  |  |  |  |
| 0 hours (Load) | 4.63E+08 | 4.63E+08 | 4.63E+08 | 4.63E+08 | 0 |
| 3 hours | 0.00E+00 | 0.00E+00 | 0.00E+00 | 0.00E+00 | 0 |

Example 34—Testing Antimicrobial Efficacy at Static Solid-Liquid Interfaces

Static Biofilm Tests

The interior of polyethylene test tubes was coated with the sulfonamide QUAT antimicrobial similarly as in Example 32. Tubes were filled with 2.7 mL of growth media (3 g/L TSB) into which 300 μL of *Arthrobacter* spp. bacterial culture was inoculated. Planktonic cells were sampled after 48 hours of incubation and agitation by removing 100 μL aliquots from each tube. After 48 hours, the liquid in each tube was removed completely so that biofilm attachment to the interior of the tubes could be assessed. To test for biofilm attachment the tubes were first gently rinsed in a saline solution to remove any loosely attached or residual planktonic cells. Next, 1 mL of saline solution was added to each tube before the tubes were vortexed vigorously for 1 minute to transfer biofilm cells to the collection liquid. Plate counts were then performed on serial dilutions of this collection liquid. Planktonic and biofilm colony counts from triplicate coated tubes were averaged and compared to colony counts from tests of uncoated control tubes carried out in parallel.

After 14 days of exposure to ambient air, the tubes used in the above test were subjected to a second static biofilm test as described above, without reapplying the antimicrobial. This test was performed to determine whether the antimicrobial effects of the coating persisted following repeated exposures.

FIG. 9 shows that 3-(4-benzoylphenoxy)-N,N-dimethyl-N-(3-(2,4,6-trimethylphenyl sulfonamido)propyl)propan-1-aminium bromide treated polyethylene test tubes inoculated with *Arthrobacter* spp. demonstrated within 48 hours excellent activity against planktonic cells. The following are tabulated bacteria reduction data:

|  | A (cfu) | B (cfu) | C (cfu) | Average | Deviation |
|---|---|---|---|---|---|
| Initial Planktonic Control |  |  |  |  |  |
| 0 hours (Load) | 7.75E+08 | 7.75E+08 | 7.75E+08 | 7.75E+08 | 0.00E+00 |
| 48 hours | 1.48E+08 | 1.58E+08 | 1.59E+08 | 1.55E+08 | 6.08E+06 |
| Initial Planktonic Treated |  |  |  |  |  |
| 0 hours (Load) | 7.75E+08 | 7.75E+08 | 7.75E+08 | 7.75E+08 | 0.00E+00 |
| 48 hours | 0.00E+00 | 0.00E+00 | 0.00E+00 | 0.00E+00 | 0.00E+00 |
| Rechallenge Planktonic Control |  |  |  |  |  |
| 0 hours (Load) | 8.00E+08 | 8.00E+08 | 8.00E+08 | 8.00E+08 | 0.00E+00 |
| 48 hours | 2.88E+08 | 1.61E+09 | 2.93E+09 | 1.61E+09 | 1.32E+09 |
| Rechallenge Planktonic Treated |  |  |  |  |  |
| 0 hours (Load) | 8.00E+08 | 8.00E+08 | 8.00E+08 | 8.00E+08 | 0.00E+00 |
| 48 hours | 0.00E+00 | 0.00E+00 | 0.00E+00 | 0.00E+00 | 0.00E+00 |

FIG. 10 shows that 3-(4-benzoylphenoxy)-N,N-dimethyl-N-(3-(2,4,6-trimethylphenyl sulfonamido)propyl)propan-1-aminium bromide treated polyethylene test tubes inoculated with *Arthrobacter* spp. demonstrated within excellent activity against biofilm development. The following are tabulated bacteria reduction data:

|  | A (cfu) | B (cfu) | C (cfu) | Average | Deviation |
|---|---|---|---|---|---|
| Initial Biofilm Control |  |  |  |  |  |
| 0 hours (Load) | 7.75E+08 | 7.75E+08 | 7.75E+08 | 7.75E+08 | 0.00E+00 |
| 48 hours | 9.00E+04 | 1.10E+05 | 6.20E+05 | 2.73E+05 | 3.00E+05 |
| Iniitial Biofilm Treated |  |  |  |  |  |
| 0 hours (Load) | 7.75E+08 | 7.75E+08 | 7.75E+08 | 7.75E+08 | 0.00E+00 |
| 48 hours | 0.00E+00 | 0.00E+00 | 0.00E+00 | 0.00E+00 | 0.00E+00 |
| Rechallenge Biofilm Control |  |  |  |  |  |
| 0 hours (Load) | 8.00E+08 | 8.00E+08 | 8.00E+08 | 8.00E+08 | 0.00E+00 |
| 48 hours | 8.90E+06 | 7.20E+06 | 6.70E+06 | 7.60E+06 | 1.15E+06 |
| Rechallenge Biofilm Treated |  |  |  |  |  |
| 0 hours (Load) | 8.00E+08 | 8.00E+08 | 8.00E+08 | 8.00E+08 | 0.00E+00 |
| 48 hours | 0.00E+00 | 0.00E+00 | 0.00E+00 | 0.00E+00 | 0.00E+00 |

As many changes can be made to the preferred embodiment of the above without departing from the scope thereof, it is intended that all matter contained herein be considered illustrative and not in a limiting sense.

We claim:

1. A quaternary ammonium sulfonamide compound of formula (I):

(I)

wherein

R = (phenyl, p-tolyl, mesityl, 2,4,6-triisopropylphenyl, naphthyl, NR₃R₄ structures)

$C_1$-$C_3$ linear or branched alkyl, $R_1$ and $R_2$ are the same or different and selected from $C_1$ to $C_{18}$ linear or branched alkyl, $R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide, l is 1, 2, 3, 4, 5, 6, 7 or 8, m is 2, 3, 4, 5, 6, 7, 8, 9, 10, 11, 12, 13, 14, 15, 16 or 17, n is 0, 1, 2, 3, 4, 5, 6, 7, 8, 9, 10, 11, 12, 13, 14, 15, 16, 17 or 18, X=halogen, and Y = (silyl ether structure with $OR_6$, $R_7O$, $OR_8$), (phosphate structure with $R_9O$, $OR_{10}$) or (benzophenone-oxy structure)

wherein $R_6$, $R_7$, $R_8$, $R_9$ and $R_{10}$ are the same or different and selected from $C_1$ to $C_6$ linear or branched alkyl, and wherein when Y = (benzophenone-oxy structure), Y may be substituted or unsubstituted, and the aryl group of R is unsubstituted.

2. The compound of claim 1 wherein the X is Br.

3. The compound of claim 1 wherein the X is Cl.

4. The compound of claim 1 wherein l is 1, m is 2 and n is 0.

5. The compound of claim 1 wherein $R_1$ and $R_2$ are the same and methyl.

6. The compound of claim 1 wherein

Y = MeO—Si(OMe)(OMe)—.

7. The compound of claim 1 wherein

Y = (benzophenone-oxy structure).

8. The compound of any one of claims 1 to 5 wherein

Y = (diisopropyl phosphate structure).

9. The use of the compound of claim 1 for reducing bacterial growth on a solid/air interface comprising introducing said compound to said solid/air interface.

10. A process for preparing a quaternary ammonium sulfonamide of formula (I):

(I)

comprising reacting a compound of formula (II)

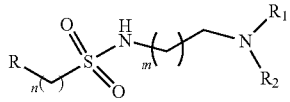

with an alkyl halide of formula (III)

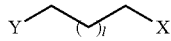

wherein

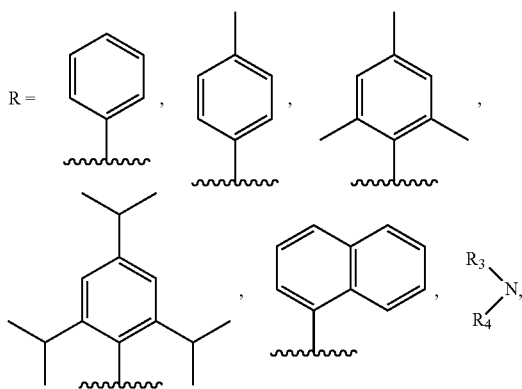

$C_1$-$C_3$ linear or branched alkyl,
$R_1$ and $R_2$ are the same or different and selected from $C_1$ to $C_{18}$ linear or branched alkyl,
$R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18,
X=halogen, and

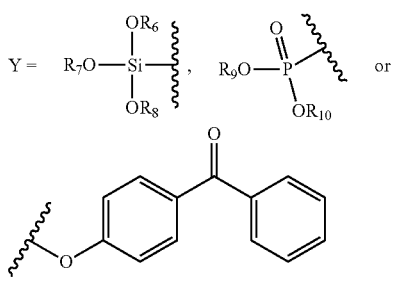

wherein $R_6$, $R_7$, $R_8$, $R_9$ and $R_{10}$ are the same or different and selected from $C_1$ to $C_6$ linear or branched alkyl.

11. An antimicrobial substrate treating composition comprising a compound of formula (I)

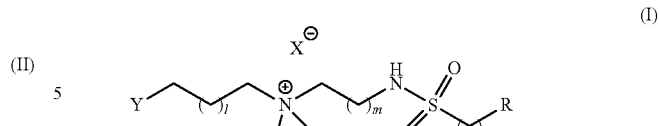

wherein

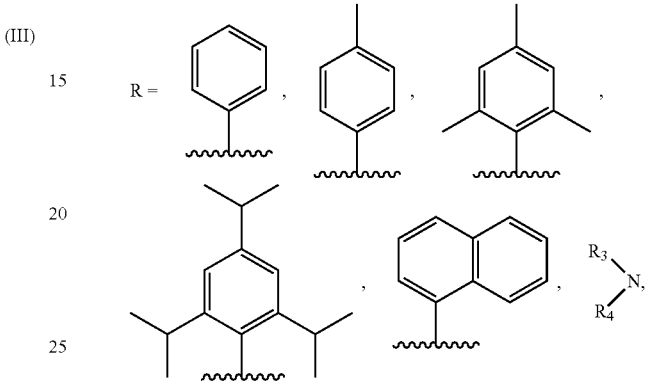

$C_1$-$C_3$ linear or branched alkyl,
$R_1$ and $R_2$ are the same or different and selected from $C_1$ to $C_{18}$ linear or branched alkyl,
$R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18,
X=halogen, and

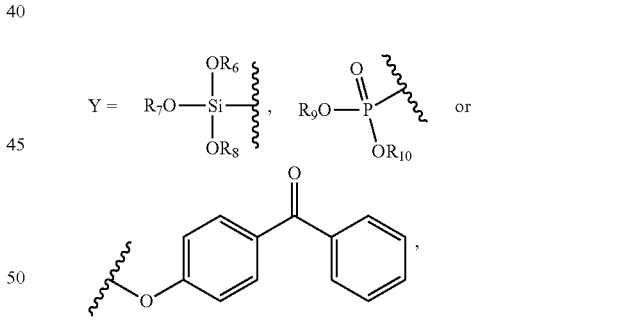

wherein $R_6$, $R_7$, $R_8$, $R_9$ and $R_{10}$ are the same or different and selected from $C_1$ to $C_6$ linear or branched alkyl, and an environmentally friendly carrier selected from the group consisting of water and at least one alkanol.

12. The composition of claim 11 wherein said environmentally friendly carrier is a mixture of water and at least one alkanol.

13. The composition of claim 12 wherein said water is distilled water and said at least one alkanol is selected from the group consisting of methanol, ethanol, isopropanol and combinations thereof.

14. A method of reducing growth of at least one microbe on a substrate comprising treating said substrate with an antimicrobial composition of claim 11.

15. A method of reducing growth of at least one microbe on a substrate comprising treating said substrate with an antimicrobial composition comprising 3-(4-benzoylphenoxy)-N,N-dimethyl-N-(3-(2,4,6-trimethylphenylsulfonamido)propyl)propan-1- aminium bromide.

16. A method of reducing growth of at least one microbe on a substrate comprising treating said substrate with an antimicrobial composition comprising 3-(4-benzoylphenoxy)-N,N-dimethyl-N-(3-(4-methylphenylsulfonamido)propyl)propan- 1-aminium bromide.

17. A method of reducing growth of at least one microbe on a substrate comprising treating said substrate with an antimicrobial composition comprising 3-(4-benzoylphenoxy)-N,N-dimethyl-N-(3-(phenylsulfonamido)propyl)propan-1- aminium bromide.

18. A method of reducing growth of at least one microbe on a substrate comprising treating said substrate with an antimicrobial composition comprising 3-(4-benzoylphenoxy)-N,N-dimethyl-N-(3-(naphthalene-1- sulfonamido)propyl)propan-1-aminium bromide.

19. A method of reducing growth of at least one microbe on a substrate comprising treating said substrate with an antimicrobial composition comprising N,N-dimethyl-3-(trimethoxysilyl)-N-(3-(2,4,6-trimethylphenylsulfonamido)propyl)propan-1-aminium chloride.

20. A method of reducing growth of at least one microbe on a substrate comprising treating said substrate with an antimicrobial composition comprising N,N-dimethyl-3-(4-methylphenylsulfonamido)-N-(3-(trimethoxysilyl)propyl)propan-1-aminium chloride.

21. A method of reducing growth of at least one microbe on a substrate comprising treating said substrate with an antimicrobial composition comprising N,N-dimethyl-3-(phenylsulfonamido)-N-(3-(trimethoxy silyl)propyl)propan-1-aminium chloride.

22. A method of reducing growth of at least one microbe on a substrate comprising treating said substrate with an antimicrobial composition comprising N,N-dimethyl-3-(naphthalene-1-sulfonamido)-N-(3-(trimethoxysilyl)propyl)propan-1-aminium chloride.

23. The method of any one of claims 14 to 22 wherein the at least one microbe is selected from the group consisting of *Listeria monocytogenes, Arthrobacter, Staphylococcus aureus, Pseudomonas aeruginosa Escherichia coli* and combinations thereof.

24. A process for treating a substrate with an antimicrobial, said process comprising the steps of:
   i) contacting the substrate with an antimicrobial composition comprising at least one compound of formula (I)

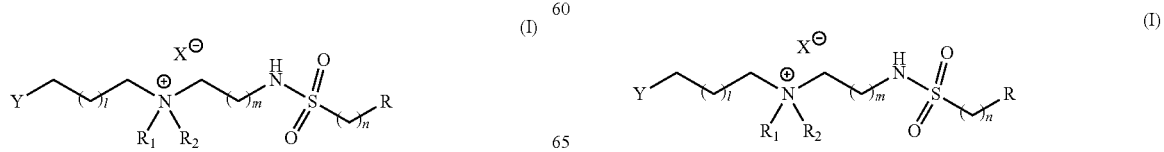

(I)

wherein

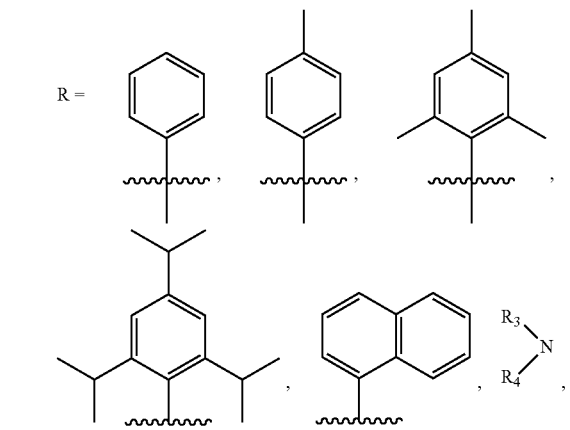

$C_1$-$C_3$ linear or branched alkyl,
$R_1$ and $R_2$ are the same or different and selected from $C_1$ to $C_{18}$ linear or branched alkyl,
$R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18,
X=halogen, and

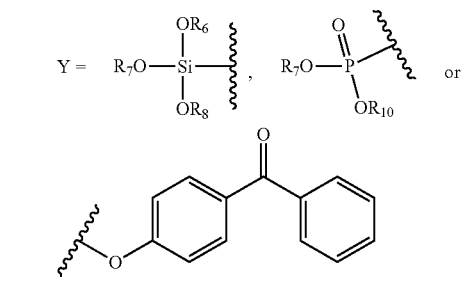

wherein $R_6$, $R_7$, $R_8$, $R_9$ and $R_{10}$ are the same or different and selected from $C_1$ to $C_6$ linear or branched alkyl, and an environmentally friendly carrier,
   (ii) drying the treated substrate passively or actively, and
   (iii) optionally irradiating the treated substrate
   wherein said environmentally friendly carrier is selected from the group consisting of water and at least one alkanol.

25. A process for treating a substrate with an antimicrobial, said process comprising the steps of:
   (i) contacting the substrate with an antimicrobial composition comprising a compound of formula (I)

(I)

wherein

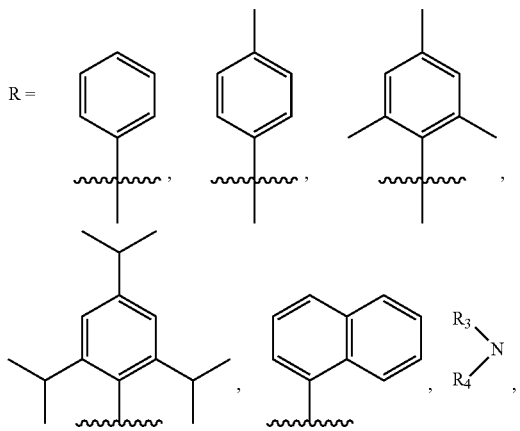

C$_1$-C$_3$ linear or branched alkyl,
R$_1$ and R$_2$ are the same or different and selected from C$_1$ to C$_{18}$ linear or branched alkyl,
R$_3$ and R$_4$ are the same or different and selected from C$_1$ to C$_4$ linear or branched alkyl, CF$_3$, OR$_5$ where R$_5$ is C$_1$ to C$_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18,
X=halogen, and

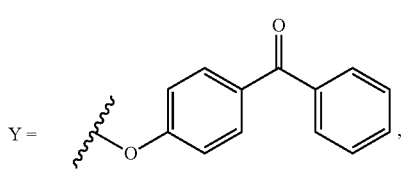

and an environmentally friendly carrier,
(ii) drying the coated substrate passively or actively, and
(iii) irradiating the coated substrate,
wherein said environmentally friendly carrier is selected from the group consisting of water and at least one alkanol.

26. The process of claim 24 or 25, wherein said environmentally friendly carrier is a mixture of water and at least one alkanol.

27. The process of claim 26, wherein said water is distilled water and said at least one alkanol is selected from the group consisting of methanol, ethanol, isopropanol and combinations thereof.

28. A process for treating a substrate with an antimicrobial, said process comprising the steps of:
i) contacting the substrate with an antimicrobial composition comprising a compound of formula (I)

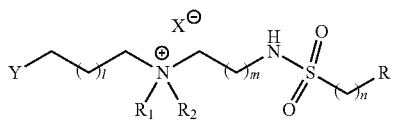

wherein

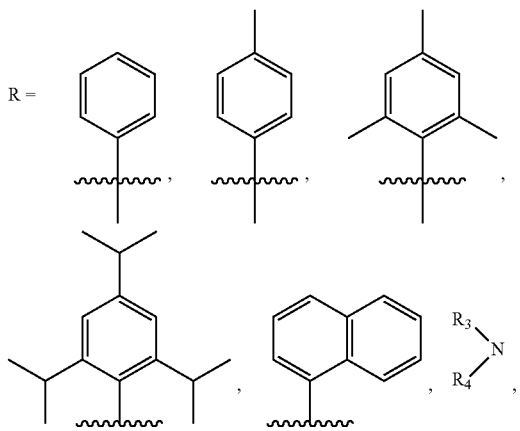

C$_1$-C$_3$ linear or branched alkyl,
R$_1$ and R$_2$ are the same or different and selected from C$_1$ to C$_{18}$ linear or branched alkyl,
R$_3$ and R$_4$ are the same or different and selected from C$_1$ to C$_4$ linear or branched alkyl, CF$_3$, OR$_5$ where R$_5$ is C$_1$ to C$_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18,
X=halogen, and

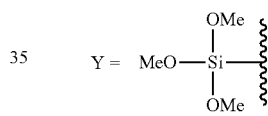

ii) drying the substrate; and
iii) washing the treated substrate.

29. The process of claim 28, further comprising stirring and heating the substrate.

30. A process for treating a substrate with an antimicrobial coating, said process comprising the steps of:
i) contacting a heated substrate with a composition comprising a compound of formula (I)

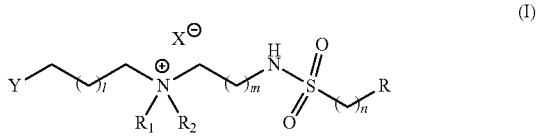

wherein

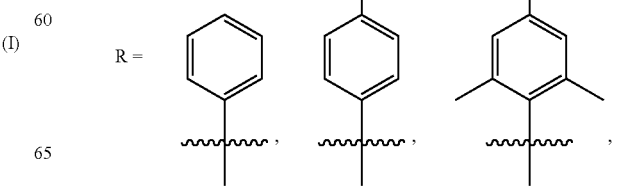

-continued

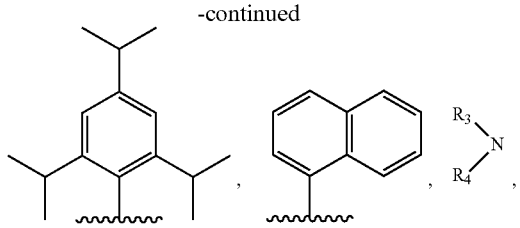

$C_1$-$C_3$ linear or branched alkyl,
$R_1$ and $R_2$ are the same or different and selected from $C_1$ to $C_{18}$ linear or branched alkyl,
$R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18,
X=halogen, and Y = 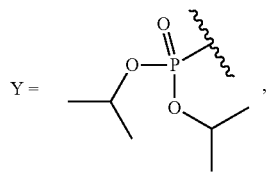 [SMILES: *P(=O)(OC(C)C)OC(C)C], and
  ii) drying the substrate.

31. Use of an antimicrobial composition comprising a compound of formula (I):

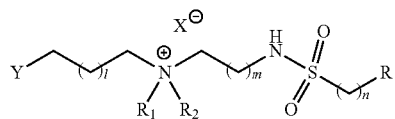

(I)

wherein

R = 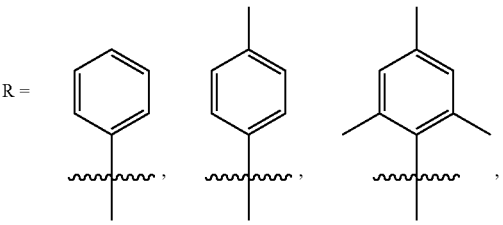

$C_1$-$C_3$ linear or branched alkyl,
$R_1$ and $R_2$ are the same or different and selected from $C_1$ to $C_{18}$ linear or branched alkyl,
$R_3$ and $R_4$ are the same or different and selected from $C_1$ to $C_4$ linear or branched alkyl, $CF_3$, $OR_5$ where $R_5$ is $C_1$ to $C_8$ linear or branched alkyl or polyethylene oxide,
l is 1, 2, 3, 4, 5, 6, 7 or 8,
m is 2, 3, 4, 5, 6, 7, 8, 9, 10, 11, 12, 13, 14, 15, 16 or 17,
n is 0, 1, 2, 3, 4, 5, 6, 7, 8, 9, 10, 11, 12, 13, 14, 15, 16, 17 or 18, wherein the aryl groups of R may be substituted or unsubstituted,
X=halogen, and Y = 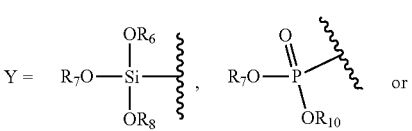 or

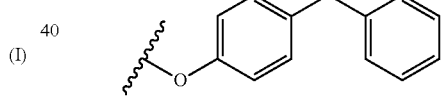

to protect a substrate from a bio-fouling comprising treating said substrate with said antimicrobial composition.

* * * * *